US012661492B2

(12) United States Patent　　(10) Patent No.:　US 12,661,492 B2
Fangrow　　(45) Date of Patent:　Jun. 23, 2026

(54) SANITIZING CAPS FOR MEDICAL CONNECTORS

(71) Applicant: ICU Medical, Inc., San Clemente, CA (US)

(72) Inventor: Thomas F. Fangrow, Mission Viejo, CA (US)

(73) Assignee: ICU Medical, Inc., San Clemente, CA (US)

( * ) Notice: Subject to any disclaimer, the term of this patent is extended or adjusted under 35 U.S.C. 154(b) by 857 days.

(21) Appl. No.: 17/021,226

(22) Filed: Sep. 15, 2020

(65) Prior Publication Data

US 2020/0406020 A1　　Dec. 31, 2020

Related U.S. Application Data

(63) Continuation of application No. PCT/US2019/022610, filed on Mar. 15, 2019.

(60) Provisional application No. 62/643,873, filed on Mar. 16, 2018.

(51) Int. Cl.
*A61M 39/16*　　(2006.01)
*A61M 39/02*　　(2006.01)
*A61M 39/20*　　(2006.01)

(52) U.S. Cl.
CPC ........ *A61M 39/16* (2013.01); *A61M 39/0247* (2013.01); *A61M 39/20* (2013.01); *A61M 2039/0285* (2013.01); *A61M 2205/0205* (2013.01)

(58) Field of Classification Search
CPC .. A61M 39/16; A61M 39/0247; A61M 39/20; A61M 2039/0285; A61M 2205/0205; A61M 25/0017; A61M 2025/0056; A61M 2209/06; A61M 39/165; A61M 39/162
See application file for complete search history.

(56) References Cited

U.S. PATENT DOCUMENTS

| 382,297 A | 5/1888 | Fry |
|---|---|---|
| 559,697 A | 5/1896 | Tiugti et al. |
| 877,946 A | 2/1908 | Overton |
| 975,939 A | 11/1910 | William et al. |
| 1,445,642 A | 2/1923 | O'Neill |
| 1,793,068 A | 2/1931 | Dickinson |
| 2,098,340 A | 11/1937 | Henahan |
| 2,436,297 A | 2/1948 | Guarnaschelli |

(Continued)

FOREIGN PATENT DOCUMENTS

| AU | 2014 216 480 | 8/2015 |
|---|---|---|
| AU | 2013 3224680 | 9/2016 |

(Continued)

OTHER PUBLICATIONS

Baxter Minicap: Photographs of the Baxter Minicap (Sep. 1, 1998) (4 pages).

(Continued)

*Primary Examiner* — James D Ponton
(74) *Attorney, Agent, or Firm* — Knobbe, Martens, Olson & Bear, LLP

(57)　　ABSTRACT

Antiseptic caps that can be used to disinfect and/or protect medical connectors are disclosed herein. In some embodiments, the antiseptic cap can include a first chamber configured to be removably attached to the medical connector.

21 Claims, 16 Drawing Sheets

(56) References Cited

U.S. PATENT DOCUMENTS

| | | |
|---|---|---|
| 2,457,052 A | 12/1948 | Le Clair |
| 2,771,644 A | 11/1956 | Martin |
| 2,842,382 A | 7/1958 | Franck |
| 2,968,497 A | 1/1961 | Treleman |
| 3,127,892 A | 4/1964 | Bellamy, Jr. et al. |
| 3,262,448 A | 7/1966 | Ring et al. |
| 3,270,743 A | 9/1966 | Gingras |
| 3,301,392 A | 1/1967 | Eddingfield |
| 3,304,047 A | 2/1967 | Martin |
| 3,334,860 A | 8/1967 | Bolton, Jr. |
| 3,411,665 A | 11/1968 | Blum |
| 3,484,121 A | 12/1969 | Quinton |
| 3,485,416 A | 12/1969 | Fohrman |
| 3,538,950 A | 11/1970 | Porteners |
| 3,595,241 A | 7/1971 | Sheridan |
| 3,604,582 A | 9/1971 | Boudin |
| 3,707,972 A | 1/1973 | Villari et al. |
| 3,729,031 A | 4/1973 | Baldwin |
| 3,882,858 A | 5/1975 | Klemm |
| 3,977,401 A | 8/1976 | Pike |
| 3,977,517 A | 8/1976 | Kadlecik et al. |
| 3,987,930 A | 10/1976 | Fuson |
| 3,993,066 A | 11/1976 | Virag |
| 4,041,934 A | 8/1977 | Genese |
| 4,046,889 A | 9/1977 | Ondetti et al. |
| 4,052,511 A | 10/1977 | Cushman et al. |
| 4,053,052 A | 10/1977 | Jasper |
| 4,053,651 A | 10/1977 | Ondetti et al. |
| 4,066,067 A | 1/1978 | Micheli |
| 4,076,285 A | 2/1978 | Martinez |
| 4,078,686 A | 3/1978 | Karesh et al. |
| 4,079,738 A | 3/1978 | Dunn et al. |
| 4,095,810 A | 6/1978 | Kulle |
| 4,113,751 A | 9/1978 | Arnold |
| 4,121,585 A | 10/1978 | Becker, Jr. |
| 4,129,571 A | 12/1978 | Ondetti et al. |
| 4,133,441 A | 1/1979 | Mittleman et al. |
| 4,143,853 A | 3/1979 | Abramson |
| 4,150,845 A | 4/1979 | Kopacz et al. |
| 4,154,840 A | 5/1979 | Ondetti et al. |
| 4,154,960 A | 5/1979 | Ondetti et al. |
| 4,192,443 A | 3/1980 | McLaren |
| 4,194,509 A | 3/1980 | Pickering et al. |
| 4,195,632 A | 4/1980 | Parker et al. |
| 4,233,982 A | 11/1980 | Bauer et al. |
| 4,243,035 A | 1/1981 | Barrett |
| 4,245,635 A | 1/1981 | Kontos |
| 4,264,664 A | 4/1981 | Kunz |
| 4,280,632 A | 7/1981 | Yuhara |
| 4,294,370 A | 10/1981 | Toeppen |
| 4,317,446 A | 3/1982 | Ambrosio et al. |
| 4,324,239 A | 4/1982 | Gordon et al. |
| 4,325,368 A | 4/1982 | Kaemmerer |
| 4,331,783 A | 5/1982 | Stoy |
| 4,334,551 A | 6/1982 | Pfister |
| 4,335,756 A | 6/1982 | Sharp et al. |
| 4,337,327 A | 6/1982 | Stoy |
| 4,340,049 A | 7/1982 | Munsch |
| 4,340,052 A | 7/1982 | Dennehey et al. |
| 4,354,490 A | 10/1982 | Rogers |
| 4,369,294 A | 1/1983 | Stoy |
| 4,370,451 A | 1/1983 | Stoy |
| 4,379,458 A | 4/1983 | Bauer et al. |
| 4,379,874 A | 4/1983 | Stoy |
| 4,384,589 A | 5/1983 | Morris |
| 4,387,879 A | 6/1983 | Tauschinski |
| 4,390,016 A | 6/1983 | Riess |
| 4,397,442 A | 8/1983 | Larkin |
| 4,402,691 A | 9/1983 | Rosenthal et al. |
| 4,405,312 A | 9/1983 | Gross et al. |
| 4,417,890 A | 11/1983 | Dennehey et al. |
| 4,420,589 A | 12/1983 | Stoy |
| 4,427,126 A | 1/1984 | Ostrowsky |
| 4,430,073 A | 2/1984 | Bemis et al. |
| 4,432,764 A | 2/1984 | Lopez |
| 4,432,766 A | 2/1984 | Bellotti et al. |
| 4,436,125 A | 3/1984 | Blenkush |
| 4,439,179 A | 3/1984 | Lueders et al. |
| 4,439,184 A | 3/1984 | Wheeler |
| 4,440,207 A | 4/1984 | Genatempo et al. |
| 4,444,310 A | 4/1984 | Odell |
| 4,446,967 A | 5/1984 | Halkyard |
| 4,447,419 A | 5/1984 | Quadro |
| 4,457,749 A | 7/1984 | Bellotti et al. |
| 4,461,368 A | 7/1984 | Plourde |
| 4,461,896 A | 7/1984 | Portlock |
| 4,480,940 A | 11/1984 | Woodruff |
| 4,507,111 A | 3/1985 | Gordon et al. |
| 4,511,359 A | 4/1985 | Vaillancourt |
| 4,534,764 A | 8/1985 | Mittleman et al. |
| 4,538,836 A | 9/1985 | Kruetten |
| 4,559,043 A | 12/1985 | Whitehouse |
| 4,568,675 A | 2/1986 | Bush et al. |
| 4,585,758 A | 4/1986 | Huang et al. |
| 4,602,042 A | 7/1986 | Chantler et al. |
| 4,610,469 A | 9/1986 | Wolff-Mooij |
| 4,619,640 A | 10/1986 | Potolsky et al. |
| 4,623,332 A | 11/1986 | Lindmayer et al. |
| 4,624,664 A | 11/1986 | Peluso et al. |
| 4,626,545 A | 12/1986 | Taub |
| 4,629,159 A | 12/1986 | Wellenstam |
| 4,631,188 A | 12/1986 | Stoy |
| 4,642,091 A | 2/1987 | Richmond |
| 4,660,803 A | 4/1987 | Johnston et al. |
| 4,662,878 A | 5/1987 | Lindmayer |
| 4,666,057 A | 5/1987 | Come et al. |
| 4,666,427 A | 5/1987 | Larsson et al. |
| 4,671,306 A | 6/1987 | Spector |
| 4,671,412 A | 6/1987 | Gatten |
| 4,681,886 A | 7/1987 | Haugwitz et al. |
| 4,692,458 A | 9/1987 | Ryan et al. |
| 4,692,459 A | 9/1987 | Ryan et al. |
| 4,700,744 A | 10/1987 | Rutter et al. |
| 4,703,762 A | 11/1987 | Rathbone et al. |
| 4,705,790 A | 11/1987 | Hubele et al. |
| 4,723,603 A | 2/1988 | Plummer |
| 4,728,075 A | 3/1988 | Paradis |
| 4,728,321 A | 3/1988 | Chen |
| 4,738,668 A | 4/1988 | Bellotti et al. |
| 4,745,950 A | 5/1988 | Mathieu |
| 4,747,502 A | 5/1988 | Luenser |
| 4,748,160 A | 5/1988 | Bennion et al. |
| 4,752,983 A | 6/1988 | Grieshaber |
| 4,769,013 A | 9/1988 | Lorenz et al. |
| 4,774,964 A | 10/1988 | Bonaldo |
| 4,774,965 A | 10/1988 | Rodriguez et al. |
| 4,778,447 A | 10/1988 | Velde et al. |
| 4,781,702 A | 11/1988 | Herrli |
| 4,799,926 A | 1/1989 | Haber |
| 4,804,015 A | 2/1989 | Albinsson |
| 4,808,158 A | 2/1989 | Kreuzer et al. |
| 4,810,241 A | 3/1989 | Rogers |
| 4,811,847 A | 3/1989 | Reif et al. |
| 4,813,933 A | 3/1989 | Turner |
| 4,816,024 A | 3/1989 | Sitar et al. |
| 4,834,271 A | 5/1989 | Litwin |
| 4,862,913 A | 9/1989 | Wildfang |
| 4,874,366 A | 10/1989 | Zdeb et al. |
| 4,883,483 A | 11/1989 | Lindmayer |
| 4,889,255 A | 12/1989 | Schiemann et al. |
| 4,894,056 A | 1/1990 | Bommarito |
| 4,898,580 A | 2/1990 | Crowley |
| 4,915,687 A | 4/1990 | Sivert |
| 4,917,669 A | 4/1990 | Bonaldo |
| 4,919,658 A | 4/1990 | Badia |
| 4,927,019 A | 5/1990 | Haber et al. |
| 4,935,010 A | 6/1990 | Cox et al. |
| 4,941,873 A | 7/1990 | Fischer |
| 4,950,260 A | 8/1990 | Bonaldo |
| 4,957,637 A | 9/1990 | Cornell |
| 4,963,132 A | 10/1990 | Gibson |
| D313,277 S | 12/1990 | Haining |
| D314,050 S | 1/1991 | Sone |
| 4,983,161 A | 1/1991 | Dadson et al. |

(56)                  References Cited

U.S. PATENT DOCUMENTS

| | | | |
|---|---|---|---|
| 4,985,017 | A | 1/1991 | Theeuwes |
| 4,989,733 | A | 2/1991 | Patry |
| 4,991,629 | A | 2/1991 | Ernesto et al. |
| 4,997,371 | A | 3/1991 | Fischer |
| 4,999,210 | A | 3/1991 | Solomon et al. |
| 5,002,964 | A | 3/1991 | Loscalzo |
| 5,006,114 | A | 4/1991 | Rogers et al. |
| 5,015,238 | A | 5/1991 | Solomon et al. |
| 5,019,096 | A | 5/1991 | Fox, Jr. et al. |
| 5,021,059 | A | 6/1991 | Kensey et al. |
| 5,024,657 | A | 6/1991 | Needham et al. |
| 5,025,001 | A | 6/1991 | Loscalzo et al. |
| 5,026,359 | A | 6/1991 | Burroughs |
| 5,031,622 | A | 7/1991 | LaHaye |
| 5,033,961 | A | 7/1991 | Kandler et al. |
| 5,047,021 | A | 9/1991 | Utterberg |
| 5,049,139 | A | 9/1991 | Gilchrist |
| 5,059,186 | A | 10/1991 | Yamamoto et al. |
| 5,065,783 | A | 11/1991 | Ogle, II |
| 5,070,885 | A | 12/1991 | Bonaldo |
| 5,071,411 | A | 12/1991 | Hillstead |
| 5,071,413 | A | 12/1991 | Utterberg |
| 5,098,385 | A | 3/1992 | Walsh |
| 5,108,376 | A | 4/1992 | Bonaldo |
| 5,122,123 | A | 6/1992 | Vaillancourt |
| 5,127,626 | A | 7/1992 | Hilal et al. |
| 5,129,824 | A | 7/1992 | Keller |
| 5,139,483 | A | 8/1992 | Ryan |
| 5,143,104 | A | 9/1992 | Iba et al. |
| 5,147,333 | A | 9/1992 | Raines |
| 5,154,703 | A | 10/1992 | Bonaldo |
| 5,154,920 | A | 10/1992 | Flesher et al. |
| 5,184,742 | A | 2/1993 | DeCaprio et al. |
| 5,190,534 | A | 3/1993 | Kendell |
| 5,195,957 | A | 3/1993 | Tollini |
| RE34,223 | E | 4/1993 | Bonaldo |
| 5,199,948 | A | 4/1993 | McPhee |
| 5,201,725 | A | 4/1993 | Kling |
| 5,203,775 | A | 4/1993 | Frank et al. |
| 5,205,820 | A | 4/1993 | Kriesel |
| 5,205,821 | A | 4/1993 | Kruger et al. |
| 5,207,706 | A | 5/1993 | Menaker |
| 5,211,634 | A | 5/1993 | Vaillancourt |
| 5,212,204 | A | 5/1993 | Keefer et al. |
| 5,215,537 | A | 6/1993 | Lynn et al. |
| 5,240,675 | A | 8/1993 | Wilk et al. |
| 5,242,421 | A | 9/1993 | Chan |
| 5,242,425 | A | 9/1993 | White et al. |
| 5,246,011 | A | 9/1993 | Caillouette |
| 5,250,550 | A | 10/1993 | Keefer et al. |
| 5,251,873 | A | 10/1993 | Atkinson et al. |
| D342,134 | S | 12/1993 | Mongeon |
| 5,269,771 | A | 12/1993 | Thomas et al. |
| 5,278,192 | A | 1/1994 | Fung et al. |
| 5,281,206 | A | 1/1994 | Lopez |
| 5,284,475 | A | 2/1994 | Mackal |
| 5,295,657 | A | 3/1994 | Atkinson |
| 5,297,310 | A | 3/1994 | Cox et al. |
| 5,301,686 | A | 4/1994 | Newman |
| 5,304,130 | A | 4/1994 | Button |
| 5,306,243 | A | 4/1994 | Bonaldo |
| 5,312,377 | A | 5/1994 | Dalton |
| 5,324,270 | A | 6/1994 | Kayan et al. |
| 5,324,647 | A | 6/1994 | Rubens et al. |
| 5,330,426 | A | 7/1994 | Kriesel et al. |
| 5,330,450 | A | 7/1994 | Lopez |
| 5,330,899 | A | 7/1994 | Devaughn et al. |
| 5,337,730 | A | 8/1994 | Maguire |
| 5,344,414 | A | 9/1994 | Lopez et al. |
| 5,352,410 | A | 10/1994 | Hansen et al. |
| 5,354,267 | A | 10/1994 | Niermann et al. |
| 5,356,396 | A | 10/1994 | Wyatt et al. |
| 5,360,413 | A | 11/1994 | Leason et al. |
| 5,366,505 | A | 11/1994 | Farber |
| 5,366,997 | A | 11/1994 | Keefer et al. |
| 5,370,614 | A | 12/1994 | Amundson et al. |
| 5,370,636 | A | 12/1994 | Von Witzleben |
| 5,370,640 | A | 12/1994 | Kolff |
| 5,375,589 | A | 12/1994 | Bhatta |
| 5,380,306 | A | 1/1995 | Brinon |
| 5,380,758 | A | 1/1995 | Stamler et al. |
| 5,391,150 | A | 2/1995 | Richmond |
| 5,402,826 | A | 4/1995 | Molnar et al. |
| 5,405,331 | A | 4/1995 | Behnke et al. |
| 5,405,333 | A | 4/1995 | Richmond |
| 5,405,919 | A | 4/1995 | Keefer et al. |
| 5,407,807 | A | 4/1995 | Markus |
| 5,409,012 | A | 4/1995 | Sahatjian |
| 5,411,499 | A | 5/1995 | Dudar et al. |
| 5,417,673 | A | 5/1995 | Gordon |
| 5,425,465 | A | 6/1995 | Healy |
| 5,428,070 | A | 6/1995 | Cooke et al. |
| 5,433,330 | A | 7/1995 | Yatsko et al. |
| 5,433,705 | A | 7/1995 | Giebel et al. |
| 5,439,451 | A | 8/1995 | Collinson et al. |
| 5,441,487 | A | 8/1995 | Vedder |
| 5,445,623 | A | 8/1995 | Richmond |
| 5,456,668 | A | 10/1995 | Ogle, II |
| 5,456,675 | A | 10/1995 | Wolbring et al. |
| 5,464,399 | A | 11/1995 | Boettger |
| 5,470,307 | A | 11/1995 | Lindall |
| 5,470,327 | A | 11/1995 | Helgren et al. |
| 5,471,706 | A | 12/1995 | Wallock et al. |
| 5,474,536 | A | 12/1995 | Bonaldo |
| 5,480,393 | A | 1/1996 | Bommarito |
| 5,485,827 | A | 1/1996 | Zapol et al. |
| 5,492,147 | A | 2/1996 | Challender et al. |
| 5,496,288 | A | 3/1996 | Sweeney |
| 5,501,426 | A | 3/1996 | Atkinson et al. |
| 5,507,733 | A | 4/1996 | Larkin et al. |
| 5,507,744 | A | 4/1996 | Tay et al. |
| 5,514,177 | A | 5/1996 | Kurz et al. |
| 5,518,026 | A | 5/1996 | Benjey |
| 5,520,665 | A | 5/1996 | Fleetwood |
| 5,520,666 | A | 5/1996 | Choudhury et al. |
| 5,525,357 | A | 6/1996 | Keefer et al. |
| 5,531,695 | A | 7/1996 | Swisher |
| 5,533,708 | A | 7/1996 | Atkinson et al. |
| 5,533,983 | A | 7/1996 | Haining |
| 5,535,785 | A | 7/1996 | Werge et al. |
| 5,536,241 | A | 7/1996 | Zapol |
| 5,536,258 | A | 7/1996 | Folden |
| 5,540,661 | A | 7/1996 | Tomisaka et al. |
| 5,545,614 | A | 8/1996 | Stamler et al. |
| 5,549,566 | A | 8/1996 | Elias et al. |
| 5,549,651 | A | 8/1996 | Lynn |
| 5,552,115 | A | 9/1996 | Malchesky |
| 5,552,118 | A | 9/1996 | Mayer |
| 5,554,127 | A | 9/1996 | Crouther et al. |
| 5,554,135 | A | 9/1996 | Menyhay |
| 5,555,908 | A | 9/1996 | Edwards et al. |
| 5,569,235 | A | 10/1996 | Ross et al. |
| 5,573,516 | A | 11/1996 | Tyner |
| 5,575,769 | A | 11/1996 | Vaillancourt |
| 5,578,059 | A | 11/1996 | Patzer |
| 5,580,530 | A | 12/1996 | Kowatsch et al. |
| 5,584,819 | A | 12/1996 | Kopfer |
| 5,591,137 | A | 1/1997 | Stevens |
| 5,591,143 | A | 1/1997 | Trombley, III et al. |
| 5,597,536 | A | 1/1997 | Mayer |
| 5,599,352 | A | 2/1997 | Dinh et al. |
| 5,605,696 | A | 2/1997 | Eury et al. |
| 5,607,072 | A | 3/1997 | Rigney et al. |
| 5,613,615 | A | 3/1997 | Zeyfang et al. |
| 5,616,130 | A | 4/1997 | Mayer |
| 5,620,088 | A | 4/1997 | Martin et al. |
| 5,620,427 | A | 4/1997 | Werschmidt et al. |
| 5,624,402 | A | 4/1997 | Imbert |
| 5,628,733 | A | 5/1997 | Zinreich et al. |
| RE35,539 | E | 6/1997 | Bonaldo |
| 5,645,538 | A | 7/1997 | Richmond |
| 5,665,077 | A | 9/1997 | Resen et al. |
| 5,674,206 | A | 10/1997 | Allton et al. |
| 5,676,346 | A | 10/1997 | Leinsing |

(56)          References Cited

U.S. PATENT DOCUMENTS

| | | | |
|---|---|---|---|
| 5,685,835 A | 11/1997 | Brugger | |
| 5,685,866 A | 11/1997 | Lopez | |
| 5,685,868 A | 11/1997 | Lundquist | |
| 5,688,253 A | 11/1997 | Lundquist | |
| 5,694,978 A | 12/1997 | Heilmann et al. | |
| 5,699,821 A | 12/1997 | Paradis | |
| 5,700,248 A | 12/1997 | Lopez | |
| 5,702,017 A | 12/1997 | Goncalves | |
| 5,716,339 A | 2/1998 | Tanaka et al. | |
| 5,722,537 A | 3/1998 | Sigler | |
| 5,735,826 A | 4/1998 | Richmond | |
| 5,738,144 A | 4/1998 | Rogers | |
| 5,743,892 A | 4/1998 | Loh et al. | |
| 5,749,861 A | 5/1998 | Guala et al. | |
| 5,763,409 A | 6/1998 | Bayol et al. | |
| 5,770,645 A | 6/1998 | Stamler et al. | |
| 5,776,116 A | 7/1998 | Lopez | |
| 5,782,808 A | 7/1998 | Folden | |
| 5,782,816 A | 7/1998 | Werschmidt et al. | |
| 5,785,693 A | 7/1998 | Haining | |
| 5,792,120 A | 8/1998 | Menyhay | |
| 5,797,887 A | 8/1998 | Rosen et al. | |
| 5,806,831 A | 9/1998 | Paradis | |
| 5,810,792 A | 9/1998 | Fangrow, Jr. et al. | |
| 5,814,024 A | 9/1998 | Thompson et al. | |
| 5,814,666 A | 9/1998 | Green et al. | |
| 5,820,601 A | 10/1998 | Mayer | |
| 5,820,604 A | 10/1998 | Fox et al. | |
| 5,827,244 A | 10/1998 | Boettger | |
| 5,839,715 A | 11/1998 | Leinsing | |
| 5,848,994 A | 12/1998 | Richmond | |
| 5,902,631 A | 5/1999 | Wang et al. | |
| 5,941,857 A | 8/1999 | Nguyen et al. | |
| 5,947,296 A * | 9/1999 | Castora .............. | A61M 25/002 |
| | | | 206/466 |
| 5,947,954 A | 9/1999 | Bonaldo | |
| 5,951,519 A | 9/1999 | Utterberg | |
| 5,954,957 A | 9/1999 | Chin-Loy et al. | |
| 5,971,972 A | 10/1999 | Rosenbaum | |
| D416,086 S | 11/1999 | Parris et al. | |
| 5,989,229 A | 11/1999 | Chiappetta | |
| 5,994,444 A | 11/1999 | Trescony | |
| 5,996,779 A | 12/1999 | Klardie et al. | |
| 6,029,946 A | 2/2000 | Doyle | |
| 6,036,171 A | 3/2000 | Weinheimer et al. | |
| 6,041,805 A | 3/2000 | Gydesen et al. | |
| 6,045,539 A | 4/2000 | Menyhay | |
| 6,045,623 A | 4/2000 | Cannon | |
| 6,050,978 A | 4/2000 | Orr et al. | |
| 6,059,107 A | 5/2000 | Nosted et al. | |
| 6,063,062 A | 5/2000 | Paradis | |
| 6,068,011 A | 5/2000 | Paradis | |
| 6,068,475 A | 5/2000 | Stoyka, Jr. et al. | |
| 6,068,617 A | 5/2000 | Richmond | |
| 6,071,413 A | 6/2000 | Dyke | |
| 6,079,432 A | 6/2000 | Paradis | |
| 6,087,479 A | 7/2000 | Stamler et al. | |
| 6,093,743 A | 7/2000 | Lai et al. | |
| 6,095,356 A | 8/2000 | Rits | |
| 6,099,519 A | 8/2000 | Olsen et al. | |
| 6,105,812 A | 8/2000 | Riordan | |
| 6,106,502 A | 8/2000 | Richmond | |
| 6,113,068 A | 9/2000 | Ryan | |
| 6,113,572 A | 9/2000 | Gailey et al. | |
| 6,116,468 A | 9/2000 | Nilson | |
| 6,117,114 A | 9/2000 | Paradis | |
| 6,126,640 A | 10/2000 | Tucker | |
| 6,142,446 A | 11/2000 | Leinsing | |
| 6,143,318 A | 11/2000 | Gilchrist et al. | |
| 6,146,363 A | 11/2000 | Giebel et al. | |
| 6,152,913 A | 11/2000 | Feith et al. | |
| 6,158,614 A | 12/2000 | Haines et al. | |
| 6,162,487 A | 12/2000 | Darouiche | |
| 6,170,522 B1 | 1/2001 | Tanida | |
| 6,171,287 B1 | 1/2001 | Lynn et al. | |
| 6,174,539 B1 | 1/2001 | Stamler et al. | |
| 6,179,141 B1 | 1/2001 | Nakamura | |
| 6,183,450 B1 | 2/2001 | Lois | |
| 6,202,870 B1 | 3/2001 | Pearce | |
| 6,202,901 B1 | 3/2001 | Gerber et al. | |
| 6,206,134 B1 | 3/2001 | Stark et al. | |
| 6,206,860 B1 | 3/2001 | Richmond | |
| 6,207,855 B1 | 3/2001 | Toone et al. | |
| 6,217,564 B1 | 4/2001 | Peters et al. | |
| 6,227,391 B1 | 5/2001 | King | |
| 6,232,406 B1 | 5/2001 | Stoy | |
| 6,232,434 B1 | 5/2001 | Stamler et al. | |
| 6,237,800 B1 | 5/2001 | Barrett et al. | |
| 6,242,393 B1 | 6/2001 | Ishida et al. | |
| 6,245,048 B1 | 6/2001 | Fangrow et al. | |
| 6,245,056 B1 | 6/2001 | Walker et al. | |
| 6,248,380 B1 | 6/2001 | Kocher et al. | |
| 6,250,315 B1 | 6/2001 | Ernster | |
| 6,255,277 B1 | 7/2001 | Stamler et al. | |
| 6,267,754 B1 | 7/2001 | Peters | |
| 6,299,132 B1 | 10/2001 | Weinheimer et al. | |
| 6,315,113 B1 | 11/2001 | Britton et al. | |
| 6,315,761 B1 | 11/2001 | Shcherbina et al. | |
| 6,359,167 B2 | 3/2002 | Toone et al. | |
| 6,359,182 B1 | 3/2002 | Stamler et al. | |
| 6,375,231 B1 | 4/2002 | Picha et al. | |
| 6,379,660 B1 | 4/2002 | Saavedra et al. | |
| 6,379,691 B1 | 4/2002 | Tedeschi et al. | |
| 6,394,983 B1 | 5/2002 | Mayoral et al. | |
| 6,402,207 B1 | 6/2002 | Segal et al. | |
| 6,403,759 B2 | 6/2002 | Stamler et al. | |
| 6,409,716 B1 | 6/2002 | Sahatjian et al. | |
| 6,428,520 B1 | 8/2002 | Lopez | |
| 6,431,219 B1 | 8/2002 | Redler et al. | |
| 6,444,318 B1 | 9/2002 | Guire et al. | |
| 6,468,259 B1 | 10/2002 | Djokic et al. | |
| 6,471,978 B1 | 10/2002 | Stamler et al. | |
| 6,488,951 B2 | 12/2002 | Toone et al. | |
| 6,491,965 B1 | 12/2002 | Berry et al. | |
| 6,499,719 B1 | 12/2002 | Clancy et al. | |
| 6,508,792 B2 | 1/2003 | Szames et al. | |
| 6,508,807 B1 | 1/2003 | Peters | |
| 6,538,116 B2 | 3/2003 | Stamler et al. | |
| 6,541,802 B2 | 4/2003 | Doyle | |
| 6,543,745 B1 | 4/2003 | Enerson | |
| 6,550,493 B2 | 4/2003 | Williamson et al. | |
| 6,555,504 B1 | 4/2003 | Ayai et al. | |
| 6,562,781 B1 | 5/2003 | Berry et al. | |
| 6,581,906 B2 | 6/2003 | Pott et al. | |
| 6,583,311 B2 | 6/2003 | Toone et al. | |
| 6,585,691 B1 | 7/2003 | Vitello | |
| 6,595,964 B2 | 7/2003 | Finley et al. | |
| 6,595,981 B2 | 7/2003 | Huet | |
| 6,605,294 B2 | 8/2003 | Sawhney | |
| 6,605,751 B1 | 8/2003 | Gibbins et al. | |
| 6,609,696 B2 | 8/2003 | Enerson | |
| 6,632,199 B1 | 10/2003 | Tucker et al. | |
| 6,634,498 B2 | 10/2003 | Kayerod et al. | |
| 6,656,217 B1 | 12/2003 | Herzog, Jr. et al. | |
| 6,666,852 B2 | 12/2003 | Niedospial, Jr. | |
| 6,673,891 B2 | 1/2004 | Stamler et al. | |
| 6,679,395 B1 | 1/2004 | Pfefferkorn et al. | |
| 6,679,870 B1 | 1/2004 | Finch et al. | |
| 6,681,803 B2 | 1/2004 | Taneya et al. | |
| 6,685,694 B2 | 2/2004 | Finch et al. | |
| 6,692,468 B1 | 2/2004 | Waldenburg | |
| 6,695,817 B1 | 2/2004 | Fangrow | |
| 6,716,396 B1 | 4/2004 | Anderson | |
| 6,722,705 B2 | 4/2004 | Korkor | |
| 6,725,492 B2 | 4/2004 | Moore et al. | |
| 6,745,998 B2 | 6/2004 | Doyle | |
| 6,786,884 B1 | 9/2004 | DeCant, Jr. et al. | |
| 6,808,510 B1 | 10/2004 | DiFiore | |
| 6,827,766 B2 | 12/2004 | Carnes et al. | |
| 6,840,501 B2 | 1/2005 | Doyle | |
| 6,871,087 B1 | 3/2005 | Hughes et al. | |
| 6,875,205 B2 | 4/2005 | Leinsing | |
| 6,875,840 B2 | 4/2005 | Stamler et al. | |
| 6,880,706 B2 | 4/2005 | Braconnot et al. | |

(56) References Cited

U.S. PATENT DOCUMENTS

| | | | |
|---|---|---|---|
| 6,887,994 | B2 | 5/2005 | Stamler et al. |
| 6,899,315 | B2 | 5/2005 | Mailville et al. |
| 6,911,025 | B2 | 6/2005 | Miyahar |
| 6,916,051 | B2 | 7/2005 | Fisher |
| 6,929,005 | B2 | 8/2005 | Sullivan et al. |
| 6,943,035 | B1 | 9/2005 | Davies et al. |
| 6,955,669 | B2 | 10/2005 | Curutcharry |
| 6,964,406 | B2 | 11/2005 | Doyle |
| 7,004,934 | B2 | 2/2006 | Vaillancourt |
| 7,015,347 | B2 | 3/2006 | Toone et al. |
| 7,030,238 | B2 | 4/2006 | Stamler et al. |
| 7,037,302 | B2 | 5/2006 | Vaillancourt |
| 7,040,598 | B2 | 5/2006 | Raybuck |
| 7,044,441 | B2 | 5/2006 | Doyle |
| 7,045,585 | B2 | 5/2006 | Berry et al. |
| 7,049,308 | B2 | 5/2006 | Stamler et al. |
| 7,052,711 | B2 | 5/2006 | West et al. |
| 7,056,308 | B2 | 6/2006 | Utterberg |
| 7,067,659 | B2 | 6/2006 | Stamler et al. |
| 7,081,109 | B2 | 7/2006 | Tighe |
| 7,083,605 | B2 | 8/2006 | Miyahara |
| 7,087,709 | B2 | 8/2006 | Stamler et al. |
| 7,097,850 | B2 | 8/2006 | Chappa et al. |
| 7,100,891 | B2 | 9/2006 | Doyle |
| 7,125,396 | B2 | 10/2006 | Leinsing et al. |
| 7,140,592 | B2 | 11/2006 | Phillips |
| 7,147,625 | B2 | 12/2006 | Sarangapani et al. |
| 7,160,272 | B1 | 1/2007 | Eyal et al. |
| 7,182,313 | B2 | 2/2007 | Doyle |
| 7,195,615 | B2 | 3/2007 | Tan |
| 7,198,611 | B2 | 4/2007 | Connell et al. |
| 7,244,249 | B2 | 7/2007 | Leinsing et al. |
| 7,259,250 | B2 | 8/2007 | Stamler et al. |
| 7,279,176 | B1 | 10/2007 | West et al. |
| 7,282,186 | B2 | 10/2007 | Lake, Jr. et al. |
| 7,306,197 | B2 | 12/2007 | Parrino et al. |
| 7,306,198 | B2 | 12/2007 | Doyle |
| 7,306,566 | B2 | 12/2007 | Raybuck |
| 7,309,326 | B2 | 12/2007 | Fangrow, Jr. |
| 7,316,669 | B2 | 1/2008 | Ranalletta |
| 7,347,458 | B2 | 3/2008 | Rome et al. |
| 7,347,853 | B2 | 3/2008 | DiFiore et al. |
| 7,350,764 | B2 | 4/2008 | Raybuck |
| 7,361,164 | B2 | 4/2008 | Simpson et al. |
| 7,417,109 | B2 | 8/2008 | Stamler et al. |
| 7,431,712 | B2 | 10/2008 | Kim |
| 7,442,402 | B2 | 10/2008 | Chudzik et al. |
| 7,452,349 | B2 | 11/2008 | Miyahar |
| 7,485,107 | B2 | 2/2009 | DiFiore et al. |
| 7,491,192 | B2 | 2/2009 | DiFiore |
| 7,497,484 | B2 | 3/2009 | Ziman |
| 7,516,846 | B2 | 4/2009 | Hansen |
| 7,588,563 | B2 | 9/2009 | Guala |
| 7,611,505 | B2 | 11/2009 | Ranalletta et al. |
| 7,614,426 | B2 | 11/2009 | Kitani et al. |
| 7,615,034 | B2 | 11/2009 | DiFiore |
| 7,625,907 | B2 | 12/2009 | Stamler et al. |
| 7,635,344 | B2 | 12/2009 | Tennican et al. |
| D607,325 | S | 1/2010 | Rogers et al. |
| 7,645,274 | B2 | 1/2010 | Whitley |
| 7,651,481 | B2 | 1/2010 | Raybuck |
| 7,666,170 | B2 | 2/2010 | Guala |
| 7,708,714 | B2 | 5/2010 | Connell et al. |
| 7,731,678 | B2 | 6/2010 | Tennican et al. |
| 7,731,679 | B2 | 6/2010 | Tennican et al. |
| 7,749,189 | B2 | 7/2010 | Tennican et al. |
| 7,753,891 | B2 | 7/2010 | Tennican et al. |
| 7,758,530 | B2 | 7/2010 | DiFiore et al. |
| 7,758,566 | B2 | 7/2010 | Simpson et al. |
| 7,762,524 | B2 | 7/2010 | Cawthon et al. |
| 7,763,006 | B2 | 7/2010 | Tennican |
| 7,766,182 | B2 | 8/2010 | Trent et al. |
| 7,766,897 | B2 | 8/2010 | Ramsey et al. |
| 7,776,011 | B2 | 8/2010 | Tennican et al. |
| 7,780,794 | B2 | 8/2010 | Rogers et al. |
| 7,785,616 | B2 | 8/2010 | Stamler et al. |
| 7,794,675 | B2 | 9/2010 | Lynn |
| 7,799,010 | B2 | 9/2010 | Tennican |
| 7,803,139 | B2 | 9/2010 | Fangrow, Jr. |
| 7,803,140 | B2 | 9/2010 | Fangrow, Jr. |
| 7,815,614 | B2 | 10/2010 | Fangrow, Jr. |
| 7,857,793 | B2 | 12/2010 | Raulerson et al. |
| 7,922,701 | B2 | 4/2011 | Buchman |
| 7,922,711 | B2 | 4/2011 | Ranalletta et al. |
| 7,928,079 | B2 | 4/2011 | Hrabie et al. |
| 7,938,795 | B2 | 5/2011 | DiFiore et al. |
| 7,956,062 | B2 | 6/2011 | Stamler et al. |
| 7,959,026 | B2 | 6/2011 | Bertani |
| 7,963,565 | B2 | 6/2011 | Suter |
| 7,972,137 | B2 | 7/2011 | Rosen |
| 7,972,322 | B2 | 7/2011 | Tennican |
| 7,981,090 | B2 | 7/2011 | Plishka et al. |
| 7,985,302 | B2 | 7/2011 | Rogers et al. |
| 7,993,309 | B2 | 8/2011 | Schweikert |
| 7,998,134 | B2 | 8/2011 | Fangrow et al. |
| 8,034,454 | B2 | 10/2011 | Terry |
| 8,065,773 | B2 | 11/2011 | Vaillancourt et al. |
| 8,066,670 | B2 | 11/2011 | Cluff et al. |
| 8,069,523 | B2 | 12/2011 | Vaillancourt et al. |
| 8,113,837 | B2 | 2/2012 | Zegarelli |
| 8,146,757 | B2 | 4/2012 | Abreu et al. |
| 8,162,899 | B2 | 4/2012 | Tennican |
| 8,167,847 | B2 | 5/2012 | Anderson et al. |
| 8,172,825 | B2 | 5/2012 | Solomon et al. |
| 8,177,761 | B2 | 5/2012 | Howlett et al. |
| 8,177,772 | B2 | 5/2012 | Christensen et al. |
| 8,197,749 | B2 | 6/2012 | Howlett et al. |
| 8,206,514 | B2 | 6/2012 | Rogers et al. |
| 8,231,587 | B2 | 7/2012 | Solomon et al. |
| 8,231,602 | B2 | 7/2012 | Anderson et al. |
| 8,252,247 | B2 | 8/2012 | Ferlic |
| 8,262,628 | B2 | 9/2012 | Fangrow, Jr. |
| 8,262,643 | B2 | 9/2012 | Tennican |
| 8,273,303 | B2 | 9/2012 | Ferlic et al. |
| 8,281,824 | B2 | 10/2012 | Molema et al. |
| 8,328,767 | B2 | 12/2012 | Solomon et al. |
| 8,336,152 | B2 | 12/2012 | Kerr et al. |
| 8,343,112 | B2 | 1/2013 | Solomon et al. |
| 8,361,408 | B2 | 1/2013 | Lynn |
| 8,372,045 | B2 | 2/2013 | Needle et al. |
| 8,377,040 | B2 | 2/2013 | Burkholz et al. |
| 8,414,547 | B2 | 4/2013 | DiFiore et al. |
| 8,419,713 | B1 | 4/2013 | Solomon et al. |
| 8,454,579 | B2 | 6/2013 | Fangrow, Jr. |
| 8,480,968 | B2 | 7/2013 | Lynn |
| 8,491,546 | B2 | 7/2013 | Hoang et al. |
| 8,500,717 | B2 | 8/2013 | Becker |
| 8,506,527 | B2 | 8/2013 | Carlyon |
| 8,506,538 | B2 | 8/2013 | Chelak |
| 8,523,798 | B2 | 9/2013 | DiFiore |
| 8,523,830 | B2 | 9/2013 | Solomon et al. |
| 8,523,831 | B2 | 9/2013 | Solomon et al. |
| 8,533,887 | B2 | 9/2013 | Hirst |
| 8,545,479 | B2 | 10/2013 | Kitani et al. |
| 8,568,371 | B2 | 10/2013 | Siopes et al. |
| 8,622,995 | B2 | 1/2014 | Ziebol et al. |
| 8,622,996 | B2 | 1/2014 | Ziebol et al. |
| 8,641,681 | B2 | 2/2014 | Solomon et al. |
| 8,641,684 | B2 | 2/2014 | Utterberg et al. |
| 8,647,308 | B2 | 2/2014 | Solomon et al. |
| 8,647,326 | B2 | 2/2014 | Solomon et al. |
| 8,651,271 | B1 | 2/2014 | Shen |
| 8,671,496 | B2 | 3/2014 | Kerr et al. |
| 8,740,864 | B2 | 6/2014 | Hoang et al. |
| 8,777,504 | B2 | 7/2014 | Shaw et al. |
| 8,791,073 | B2 | 7/2014 | West et al. |
| 8,845,593 | B2 | 9/2014 | Anderson et al. |
| 8,877,231 | B2 | 11/2014 | Rosen |
| 8,910,919 | B2 | 12/2014 | Bonnal et al. |
| 8,920,404 | B2 | 12/2014 | DiFiore et al. |
| 8,968,268 | B2 | 3/2015 | Anderson et al. |
| 8,981,139 | B2 | 3/2015 | Schoenfisch et al. |
| 8,999,073 | B2 | 4/2015 | Rogers et al. |
| 9,022,984 | B2 | 5/2015 | Ziebol et al. |

(56) References Cited

U.S. PATENT DOCUMENTS

| | | | |
|---|---|---|---|
| 9,072,296 B2 | 7/2015 | Mills et al. | |
| 9,072,868 B2 | 7/2015 | Ziebol et al. | |
| 9,078,992 B2 | 7/2015 | Ziebol et al. | |
| 9,089,680 B2 | 7/2015 | Ueda et al. | |
| 9,095,500 B2 | 8/2015 | Brandenburger et al. | |
| 9,095,667 B2 | 8/2015 | Von Schuckmann | |
| 9,101,685 B2 | 8/2015 | Li et al. | |
| 9,101,750 B2 | 8/2015 | Solomon et al. | |
| 9,114,915 B2 | 8/2015 | Solomon et al. | |
| 9,125,600 B2 | 9/2015 | Steube et al. | |
| 9,149,624 B2 | 10/2015 | Lewis | |
| 9,180,252 B2 | 11/2015 | Gelblum et al. | |
| 9,192,449 B2 | 11/2015 | Kerr et al. | |
| 9,205,248 B2 | 12/2015 | Wu et al. | |
| 9,216,440 B2 | 12/2015 | Ma et al. | |
| 9,233,208 B2 | 1/2016 | Tekeste | |
| 9,242,084 B2 | 1/2016 | Solomon et al. | |
| 9,248,093 B2 | 2/2016 | Kelley, III et al. | |
| 9,248,229 B2 | 2/2016 | Devouassoux et al. | |
| 9,259,284 B2 | 2/2016 | Rogers et al. | |
| 9,259,535 B2 | 2/2016 | Anderson et al. | |
| 9,283,367 B2 | 3/2016 | Hoang et al. | |
| 9,283,368 B2 | 3/2016 | Hoang et al. | |
| 9,283,369 B2 | 3/2016 | Ma et al. | |
| 9,289,588 B2 | 3/2016 | Chen | |
| 9,296,525 B2 | 3/2016 | Murphy et al. | |
| 9,302,049 B2 | 4/2016 | Tekeste | |
| 9,320,858 B2 | 4/2016 | Grimm et al. | |
| 9,320,859 B2 | 4/2016 | Grimm et al. | |
| 9,320,860 B2 | 4/2016 | Grimm et al. | |
| 9,352,080 B2 | 5/2016 | Goodall et al. | |
| 9,352,140 B2 | 5/2016 | Kerr et al. | |
| 9,352,141 B2 | 5/2016 | Wong | |
| 9,352,142 B2 | 5/2016 | Ziebol et al. | |
| 9,381,339 B2 | 7/2016 | Wu et al. | |
| 9,399,125 B2 | 7/2016 | Burkholz | |
| 9,408,971 B2 | 8/2016 | Carlyon | |
| 9,527,660 B2 | 12/2016 | Tennican | |
| 9,592,375 B2 | 3/2017 | Tennican | |
| 9,700,676 B2 | 7/2017 | Anderson et al. | |
| 9,700,677 B2 | 7/2017 | Anderson et al. | |
| 9,700,710 B2 | 7/2017 | Anderson et al. | |
| 9,707,348 B2 | 7/2017 | Anderson et al. | |
| 9,707,349 B2 | 7/2017 | Anderson et al. | |
| 9,707,350 B2 | 7/2017 | Anderson et al. | |
| 9,809,355 B2 | 11/2017 | Solomon et al. | |
| 9,849,276 B2 | 12/2017 | Ziebol et al. | |
| 9,867,975 B2 | 1/2018 | Gardner et al. | |
| 9,907,617 B2 | 3/2018 | Rogers | |
| 9,933,094 B2 | 4/2018 | Fangrow | |
| 9,999,471 B2 | 6/2018 | Rogers et al. | |
| 10,016,587 B2 | 7/2018 | Gardner et al. | |
| 10,046,156 B2 | 8/2018 | Gardner et al. | |
| 10,159,829 B2 | 12/2018 | Ziebol et al. | |
| 10,166,381 B2 | 1/2019 | Gardner et al. | |
| 10,195,000 B2 | 2/2019 | Rogers et al. | |
| 10,201,692 B2 | 2/2019 | Chang | |
| 10,328,207 B2 | 6/2019 | Anderson et al. | |
| 10,524,982 B2 | 1/2020 | Fangrow | |
| 10,525,250 B1 | 1/2020 | Ziebol et al. | |
| 10,695,550 B2 | 6/2020 | Gardner et al. | |
| 10,744,316 B2 | 8/2020 | Fangrow | |
| 10,806,919 B2 | 10/2020 | Gardner et al. | |
| 10,821,278 B2 | 11/2020 | Gardner et al. | |
| 11,160,932 B2 | 11/2021 | Anderson et al. | |
| 11,229,746 B2 | 1/2022 | Anderson et al. | |
| 11,351,353 B2 | 6/2022 | Ziebol et al. | |
| 11,389,634 B2 | 7/2022 | Ziebol et al. | |
| 11,400,195 B2 | 8/2022 | Ziebol et al. | |
| 11,433,215 B2 | 9/2022 | Ziebol et al. | |
| 11,497,904 B2 | 11/2022 | Fangrow et al. | |
| 11,517,732 B2 | 12/2022 | Ziebol et al. | |
| 11,517,733 B2 | 12/2022 | Fangrow | |
| 11,534,595 B2 | 12/2022 | Ziebol et al. | |
| 11,541,220 B2 | 1/2023 | Ziebol et al. | |
| 11,541,221 B2 | 1/2023 | Ziebol et al. | |
| 11,559,467 B2 | 1/2023 | Fangrow | |
| 11,684,720 B2 | 6/2023 | Anderson et al. | |
| 11,826,539 B2 | 11/2023 | Ziebol et al. | |
| 11,944,776 B2 | 4/2024 | Ziebol et al. | |
| 11,998,715 B2 | 6/2024 | Gardner | |
| 12,042,640 B2 | 7/2024 | Anderson et al. | |
| 12,076,521 B2 | 9/2024 | Gardner et al. | |
| 12,109,365 B2 | 10/2024 | Ziebol | |
| 12,186,520 B2 | 1/2025 | Ziebol et al. | |
| 12,201,760 B2 | 1/2025 | Ziebol et al. | |
| 12,485,263 B2 | 12/2025 | Ziebol et al. | |
| 12,485,264 B2 | 12/2025 | Gardner | |
| 2002/0077693 A1 | 6/2002 | Barclay et al. | |
| 2002/0082682 A1 | 6/2002 | Barclay et al. | |
| 2002/0098278 A1 | 7/2002 | Bates et al. | |
| 2003/0039697 A1 | 2/2003 | Zhao et al. | |
| 2003/0062376 A1 | 4/2003 | Sears et al. | |
| 2003/0072783 A1 | 4/2003 | Stamler et al. | |
| 2003/0078242 A1 | 4/2003 | Raad et al. | |
| 2003/0153865 A1 | 8/2003 | Connell et al. | |
| 2003/0199835 A1 | 10/2003 | Leinsing et al. | |
| 2003/0208165 A1 | 11/2003 | Christensen et al. | |
| 2004/0034042 A1 | 2/2004 | Tsuji et al. | |
| 2004/0034329 A1 | 2/2004 | Mankus et al. | |
| 2004/0037836 A1 | 2/2004 | Stamler et al. | |
| 2004/0048542 A1 | 3/2004 | Thomaschefsky et al. | |
| 2004/0052689 A1 | 3/2004 | Yao | |
| 2004/0052831 A1 | 3/2004 | Modak et al. | |
| 2004/0073176 A1* | 4/2004 | Utterberg | A61M 39/26 |
| | | | 604/256 |
| 2004/0156908 A1 | 8/2004 | Polaschegg et al. | |
| 2004/0210201 A1 | 10/2004 | Farnan | |
| 2004/0215148 A1 | 10/2004 | Hwang et al. | |
| 2004/0247640 A1 | 12/2004 | Zhao et al. | |
| 2004/0249337 A1 | 12/2004 | DiFiore | |
| 2004/0249338 A1 | 12/2004 | DeCant, Jr. et al. | |
| 2005/0008763 A1 | 1/2005 | Schachter | |
| 2005/0013836 A1 | 1/2005 | Raad | |
| 2005/0015075 A1 | 1/2005 | Wright et al. | |
| 2005/0065479 A1 | 3/2005 | Schiller et al. | |
| 2005/0098527 A1 | 5/2005 | Yates et al. | |
| 2005/0124942 A1 | 6/2005 | Richmond | |
| 2005/0124970 A1 | 6/2005 | Kunin et al. | |
| 2005/0147524 A1 | 7/2005 | Bousquet | |
| 2005/0147525 A1 | 7/2005 | Bousquet | |
| 2005/0148930 A1 | 7/2005 | Hseih et al. | |
| 2005/0152891 A1 | 7/2005 | Toone et al. | |
| 2005/0171493 A1 | 8/2005 | Nicholls | |
| 2005/0197634 A1 | 9/2005 | Raad et al. | |
| 2005/0214185 A1 | 9/2005 | Castaneda | |
| 2005/0220882 A1 | 10/2005 | Pritchard et al. | |
| 2005/0228362 A1 | 10/2005 | Vaillancourt | |
| 2005/0228482 A1 | 10/2005 | Herzog et al. | |
| 2005/0256461 A1 | 11/2005 | DiFiore et al. | |
| 2005/0265958 A1 | 12/2005 | West et al. | |
| 2005/0267421 A1 | 12/2005 | Wing | |
| 2005/0271711 A1 | 12/2005 | Lynch et al. | |
| 2005/0288551 A1 | 12/2005 | Callister et al. | |
| 2006/0004316 A1 | 1/2006 | DiFiore et al. | |
| 2006/0024372 A1 | 2/2006 | Utterberg et al. | |
| 2006/0058734 A1 | 3/2006 | Phillips | |
| 2006/0096348 A1 | 5/2006 | DiFiore | |
| 2006/0118122 A1 | 6/2006 | Martens et al. | |
| 2006/0129109 A1 | 6/2006 | Shaw et al. | |
| 2006/0142730 A1 | 6/2006 | Proulx et al. | |
| 2006/0149191 A1 | 7/2006 | DiFiore | |
| 2006/0161115 A1 | 7/2006 | Fangrow | |
| 2006/0195117 A1 | 8/2006 | Rucker et al. | |
| 2006/0202146 A1 | 9/2006 | Doyle | |
| 2006/0206178 A1 | 9/2006 | Kim | |
| 2006/0253084 A1 | 11/2006 | Nordgren | |
| 2006/0261076 A1 | 11/2006 | Anderson | |
| 2007/0003603 A1 | 1/2007 | Karandikar et al. | |
| 2007/0088292 A1 | 4/2007 | Fangrow | |
| 2007/0088293 A1 | 4/2007 | Fangrow | |
| 2007/0088294 A1 | 4/2007 | Fangrow | |
| 2007/0106205 A1 | 5/2007 | Connell et al. | |
| 2007/0112333 A1 | 5/2007 | Hoang et al. | |

(56) References Cited

U.S. PATENT DOCUMENTS

| | | |
|---|---|---|
| 2007/0154621 A1 | 7/2007 | Raad |
| 2007/0156118 A1 | 7/2007 | Ramsey et al. |
| 2007/0167910 A1 | 7/2007 | Tennican et al. |
| 2007/0176117 A1 | 8/2007 | Redmond et al. |
| 2007/0179453 A1 | 8/2007 | Lim et al. |
| 2007/0187353 A1 | 8/2007 | Fox et al. |
| 2007/0202177 A1 | 8/2007 | Hoang |
| 2007/0212381 A1 | 9/2007 | DiFiore et al. |
| 2007/0231315 A1 | 10/2007 | Lichte et al. |
| 2007/0248676 A1 | 10/2007 | Stamler et al. |
| 2007/0249996 A1 | 10/2007 | Tennican et al. |
| 2007/0265578 A1 | 11/2007 | Tennican et al. |
| 2007/0287989 A1 | 12/2007 | Crawford et al. |
| 2008/0014005 A1 | 1/2008 | Kitabatake |
| 2008/0027399 A1 | 1/2008 | Harding et al. |
| 2008/0027401 A1 | 1/2008 | Ou-Yang |
| 2008/0033371 A1 | 2/2008 | Updegraff et al. |
| 2008/0039803 A1 | 2/2008 | Lynn |
| 2008/0058733 A1 | 3/2008 | Vogt et al. |
| 2008/0093245 A1 | 4/2008 | Periasamy et al. |
| 2008/0095680 A1 | 4/2008 | Steffens et al. |
| 2008/0097315 A1 | 4/2008 | Miner et al. |
| 2008/0097407 A1* | 4/2008 | Plishka ................. A61M 39/26 |
| | | 604/533 |
| 2008/0103485 A1 | 5/2008 | Kruger |
| 2008/0128646 A1 | 6/2008 | Clawson |
| 2008/0132880 A1 | 6/2008 | Buchman |
| 2008/0147047 A1 | 6/2008 | Davis et al. |
| 2008/0161763 A1 | 7/2008 | Harding et al. |
| 2008/0172007 A1 | 7/2008 | Bousquet |
| 2008/0173651 A1 | 7/2008 | Ping |
| 2008/0177250 A1 | 7/2008 | Howlett et al. |
| 2008/0187460 A1 | 8/2008 | Utterberg et al. |
| 2008/0188791 A1 | 8/2008 | DiFiore et al. |
| 2008/0190485 A1 | 8/2008 | Guala |
| 2008/0193211 A1 | 8/2008 | Burton et al. |
| 2008/0235888 A1 | 10/2008 | Vaillancourt et al. |
| 2008/0262465 A1 | 10/2008 | Zinger et al. |
| 2008/0287920 A1 | 11/2008 | Fangrow et al. |
| 2008/0318333 A1 | 12/2008 | Nielsen et al. |
| 2008/0319423 A1 | 12/2008 | Tanghoj et al. |
| 2009/0008393 A1 | 1/2009 | Howlett et al. |
| 2009/0012426 A1 | 1/2009 | Tennican |
| 2009/0024096 A1 | 1/2009 | Hai et al. |
| 2009/0028750 A1 | 1/2009 | Ryan |
| 2009/0062766 A1 | 3/2009 | Howlett et al. |
| 2009/0093757 A1 | 4/2009 | Tennican |
| 2009/0099529 A1 | 4/2009 | Anderson et al. |
| 2009/0126867 A1 | 5/2009 | Decant, Jr. et al. |
| 2009/0137969 A1 | 5/2009 | Colantonio et al. |
| 2009/0149820 A1 | 6/2009 | DiFiore |
| 2009/0163876 A1 | 6/2009 | Chebator et al. |
| 2009/0205151 A1 | 8/2009 | Fisher et al. |
| 2009/0205656 A1 | 8/2009 | Nishibayashi et al. |
| 2009/0247485 A1 | 10/2009 | Ahmed et al. |
| 2009/0259194 A1 | 10/2009 | Pinedjian et al. |
| 2009/0270832 A1 | 10/2009 | Vancaillie et al. |
| 2009/0293882 A1 | 12/2009 | Terry |
| 2010/0004510 A1 | 1/2010 | Kuroshima |
| 2010/0010086 A1 | 1/2010 | Ash et al. |
| 2010/0047123 A1 | 2/2010 | Solomon et al. |
| 2010/0049170 A1 | 2/2010 | Solomon et al. |
| 2010/0050351 A1 | 3/2010 | Colantonio et al. |
| 2010/0064456 A1 | 3/2010 | Ferlic |
| 2010/0074932 A1 | 3/2010 | Talsma |
| 2010/0106102 A1 | 4/2010 | Ziebol et al. |
| 2010/0106103 A1 | 4/2010 | Ziebol et al. |
| 2010/0137472 A1 | 6/2010 | Ou-Yang |
| 2010/0143427 A1 | 6/2010 | King et al. |
| 2010/0152670 A1 | 6/2010 | Low |
| 2010/0160894 A1 | 6/2010 | Julian et al. |
| 2010/0172794 A1 | 7/2010 | Ferlic et al. |
| 2010/0242993 A1 | 9/2010 | Hoang et al. |
| 2010/0253070 A1 | 10/2010 | Cheon et al. |
| 2010/0280805 A1 | 11/2010 | DiFiore |
| 2010/0292673 A1 | 11/2010 | Korogi et al. |
| 2010/0292674 A1 | 11/2010 | Jepson et al. |
| 2010/0306938 A1 | 12/2010 | Rogers et al. |
| 2010/0318040 A1 | 12/2010 | Kelley, III et al. |
| 2011/0030726 A1 | 2/2011 | Vaillancourt et al. |
| 2011/0044850 A1 | 2/2011 | Solomon et al. |
| 2011/0046564 A1 | 2/2011 | Zhong |
| 2011/0046603 A1 | 2/2011 | Felsovalyi et al. |
| 2011/0062703 A1 | 3/2011 | Lopez |
| 2011/0064512 A1 | 3/2011 | Shaw et al. |
| 2011/0071475 A1 | 3/2011 | Horvath et al. |
| 2011/0082431 A1 | 4/2011 | Burgess et al. |
| 2011/0150958 A1 | 6/2011 | Davis et al. |
| 2011/0184338 A1 | 7/2011 | McKay |
| 2011/0184382 A1 | 7/2011 | Cady |
| 2011/0208128 A1 | 8/2011 | Wu et al. |
| 2011/0217212 A1 | 9/2011 | Solomon et al. |
| 2011/0276031 A1 | 11/2011 | Hoang et al. |
| 2011/0282302 A1 | 11/2011 | Lopez et al. |
| 2011/0311602 A1 | 12/2011 | Mills et al. |
| 2011/0314619 A1 | 12/2011 | Schweikert |
| 2012/0022469 A1 | 1/2012 | Albert et al. |
| 2012/0029483 A1 | 2/2012 | Griffith et al. |
| 2012/0031904 A1 | 2/2012 | Kuhn et al. |
| 2012/0039764 A1 | 2/2012 | Solomon et al. |
| 2012/0083730 A1 | 4/2012 | Rush et al. |
| 2012/0083750 A1 | 4/2012 | Sansoucy |
| 2012/0157965 A1 | 6/2012 | Wotton et al. |
| 2012/0191029 A1 | 7/2012 | Hopf et al. |
| 2012/0195807 A1 | 8/2012 | Ferlic |
| 2012/0216359 A1 | 8/2012 | Rogers et al. |
| 2012/0216360 A1 | 8/2012 | Rogers et al. |
| 2012/0220955 A1 | 8/2012 | Maseda et al. |
| 2012/0283696 A1 | 11/2012 | Cronenberg et al. |
| 2012/0302968 A1 | 11/2012 | Tennican |
| 2012/0302970 A1 | 11/2012 | Tennican |
| 2012/0302997 A1* | 11/2012 | Gardner ................ A61M 39/20 |
| | | 604/533 |
| 2012/0315201 A1 | 12/2012 | Ferlic et al. |
| 2013/0006194 A1 | 1/2013 | Anderson et al. |
| 2013/0023828 A1 | 1/2013 | Anderson et al. |
| 2013/0030414 A1 | 1/2013 | Gardner et al. |
| 2013/0035667 A1 | 2/2013 | Anderson et al. |
| 2013/0039953 A1 | 2/2013 | Dudnyk et al. |
| 2013/0053751 A1 | 2/2013 | Holtham |
| 2013/0072908 A1 | 3/2013 | Solomon et al. |
| 2013/0085313 A1 | 4/2013 | Fowler et al. |
| 2013/0085474 A1 | 4/2013 | Charles et al. |
| 2013/0098398 A1 | 4/2013 | Kerr et al. |
| 2013/0098938 A1 | 4/2013 | Efthimiadis |
| 2013/0102950 A1 | 4/2013 | DiFiore |
| 2013/0123754 A1 | 5/2013 | Solomon et al. |
| 2013/0134161 A1 | 5/2013 | Fogel et al. |
| 2013/0138085 A1 | 5/2013 | Tennican |
| 2013/0144258 A1 | 6/2013 | Ziebol et al. |
| 2013/0150795 A1 | 6/2013 | Snow |
| 2013/0164189 A1 | 6/2013 | Hadden |
| 2013/0171030 A1 | 7/2013 | Ferlic et al. |
| 2013/0183635 A1 | 7/2013 | Wilhoit |
| 2013/0184679 A1 | 7/2013 | Ziebol et al. |
| 2013/0204231 A1 | 8/2013 | Ziebol et al. |
| 2013/0255061 A1 | 10/2013 | Burkholz |
| 2013/0274686 A1 | 10/2013 | Ziebol et al. |
| 2014/0042116 A1 | 2/2014 | Shen et al. |
| 2014/0048079 A1 | 2/2014 | Gardner et al. |
| 2014/0052074 A1 | 2/2014 | Tekeste |
| 2014/0101876 A1 | 4/2014 | Rogers et al. |
| 2014/0155868 A1 | 6/2014 | Nelson et al. |
| 2014/0227144 A1* | 8/2014 | Liu .......................... A61L 2/16 |
| | | 422/300 |
| 2014/0228775 A1 | 8/2014 | Burkholz et al. |
| 2014/0228809 A1 | 8/2014 | Wong |
| 2014/0243797 A1 | 8/2014 | Jensen et al. |
| 2014/0261758 A1 | 9/2014 | Wlodarczyk et al. |
| 2014/0336610 A1 | 11/2014 | Michel et al. |
| 2014/0339812 A1 | 11/2014 | Carney et al. |
| 2014/0339813 A1 | 11/2014 | Cederschiöld et al. |
| 2015/0086441 A1 | 3/2015 | She et al. |
| 2015/0141934 A1 | 5/2015 | Gardner et al. |

(56) References Cited

U.S. PATENT DOCUMENTS

| | | |
|---|---|---|
| 2015/0148287 A1 | 5/2015 | Woo et al. |
| 2015/0157799 A1 | 6/2015 | Chen et al. |
| 2015/0157800 A1 | 6/2015 | Chen et al. |
| 2015/0165127 A1 | 6/2015 | Haefele et al. |
| 2015/0217106 A1 | 8/2015 | Banik et al. |
| 2015/0231380 A1 | 8/2015 | Hoang et al. |
| 2015/0237854 A1 | 8/2015 | Mills et al. |
| 2015/0238703 A1 | 8/2015 | Glocker |
| 2015/0258324 A1 | 9/2015 | Chida et al. |
| 2015/0273199 A1 | 10/2015 | Adams et al. |
| 2015/0297455 A1 | 10/2015 | Sanders et al. |
| 2015/0297881 A1 | 10/2015 | Sanders et al. |
| 2015/0298893 A1 | 10/2015 | Welp |
| 2015/0306367 A1 | 10/2015 | DiFiore |
| 2015/0306369 A1 | 10/2015 | Burkholz et al. |
| 2015/0314119 A1 | 11/2015 | Anderson et al. |
| 2015/0320926 A1 | 11/2015 | Fitzpatrick et al. |
| 2015/0320992 A1 | 11/2015 | Bonnet et al. |
| 2015/0343174 A1 | 12/2015 | Ziebol et al. |
| 2015/0374968 A1 | 12/2015 | Solomon et al. |
| 2016/0001056 A1 | 1/2016 | Nelson et al. |
| 2016/0001058 A1 | 1/2016 | Ziebol et al. |
| 2016/0015863 A1 | 1/2016 | Gupta et al. |
| 2016/0015931 A1 | 1/2016 | Ryan et al. |
| 2016/0015959 A1 | 1/2016 | Solomon et al. |
| 2016/0045629 A1 | 2/2016 | Gardner et al. |
| 2016/0067365 A1 | 3/2016 | Ma et al. |
| 2016/0067471 A1 | 3/2016 | Ingram et al. |
| 2016/0088995 A1 | 3/2016 | Ueda et al. |
| 2016/0089530 A1 | 3/2016 | Sathe |
| 2016/0101223 A1 | 4/2016 | Kelley, III et al. |
| 2016/0101276 A1 | 4/2016 | Tekeste |
| 2016/0106969 A1 | 4/2016 | Neftel |
| 2016/0121097 A1 | 5/2016 | Steele |
| 2016/0144118 A1 | 5/2016 | Solomon et al. |
| 2016/0158520 A1 | 6/2016 | Ma et al. |
| 2016/0158521 A1 | 6/2016 | Hoang et al. |
| 2016/0158522 A1 | 6/2016 | Hoang et al. |
| 2016/0184527 A1 | 6/2016 | Tekeste |
| 2016/0213912 A1 | 7/2016 | Daneluzzi |
| 2016/0220790 A1 | 8/2016 | Borowicz |
| 2016/0250420 A1 | 9/2016 | Maritan et al. |
| 2016/0354596 A1 | 12/2016 | DiFiore |
| 2017/0020911 A1 | 1/2017 | Berry et al. |
| 2017/0042636 A1 | 2/2017 | Young |
| 2017/0143447 A1* | 5/2017 | Rogers ..................... B08B 3/08 |
| 2017/0182241 A1 | 6/2017 | DiFiore |
| 2017/0203092 A1 | 7/2017 | Ryan et al. |
| 2017/0239443 A1 | 8/2017 | Abitabilo et al. |
| 2018/0028403 A1 | 2/2018 | Fangrow |
| 2018/0085568 A1 | 3/2018 | Drmanovic |
| 2018/0200500 A1 | 7/2018 | Ziebol et al. |
| 2018/0200501 A1 | 7/2018 | Her |
| 2018/0214684 A1 | 8/2018 | Avula et al. |
| 2019/0351211 A1 | 11/2019 | Dombrowski et al. |
| 2020/0139037 A1 | 5/2020 | Ziebol et al. |
| 2020/0139102 A1 | 5/2020 | Ziebol et al. |
| 2020/0139103 A1 | 5/2020 | Ziebol et al. |
| 2020/0139104 A1 | 5/2020 | Ziebol et al. |
| 2020/0324102 A1 | 10/2020 | Fangrow |
| 2020/0330741 A1 | 10/2020 | Fangrow |
| 2021/0093791 A1 | 4/2021 | Anderson |
| 2021/0106805 A1 | 4/2021 | Fangrow |
| 2021/0162194 A1 | 6/2021 | Gardner |
| 2021/0205596 A1 | 7/2021 | Ziebol et al. |
| 2021/0308442 A1 | 10/2021 | Gardner |
| 2022/0226629 A1 | 7/2022 | Ziebel |
| 2022/0288258 A1 | 9/2022 | Gardner |
| 2022/0288376 A1 | 9/2022 | Ziebol |
| 2022/0313977 A1 | 10/2022 | Gugel et al. |
| 2022/0379035 A1 | 12/2022 | Anderson |
| 2022/0387685 A1 | 12/2022 | Ziebol |
| 2022/0401652 A1 | 12/2022 | Anderson |
| 2023/0030414 A1 | 2/2023 | Charrier et al. |
| 2023/0069367 A1 | 3/2023 | Ziebol |
| 2023/0105566 A1 | 4/2023 | Fangrow |
| 2023/0121450 A1 | 4/2023 | Ziebol |
| 2023/0285735 A1 | 9/2023 | Ziebol |
| 2023/0288258 A1 | 9/2023 | Gardner |
| 2024/0050729 A1 | 2/2024 | Ziebol |
| 2024/0050730 A1 | 2/2024 | Fangrow |
| 2024/0139489 A1 | 5/2024 | Ziebol |
| 2024/0216667 A1 | 7/2024 | Ziebol |
| 2025/0025663 A1 | 1/2025 | Ziebol |
| 2025/0099686 A1 | 3/2025 | Anderson |
| 2025/0099732 A1 | 3/2025 | Gardner |
| 2025/0099733 A1 | 3/2025 | Gardner |
| 2025/0121174 A1 | 4/2025 | Ziebol |

FOREIGN PATENT DOCUMENTS

| | | |
|---|---|---|
| CA | 2 148 847 | 12/1995 |
| CA | 2825217 | 3/2007 |
| CA | 2 769 157 | 2/2011 |
| CA | 2 841 832 | 6/2019 |
| CN | 2402327 Y | 10/2000 |
| CN | 2815392 Y | 9/2006 |
| CN | 201150420 Y | 11/2008 |
| CN | 201519335 U | 7/2010 |
| CN | 102 844 073 A | 12/2012 |
| CN | 103260696 A | 8/2013 |
| CN | 106902402 | 6/2017 |
| CN | 107837428 | 3/2018 |
| DE | 3515665 | 5/1986 |
| DE | 89 06 628 U1 | 9/1989 |
| DE | 43 34 272 | 4/1995 |
| DE | 29617133 | 1/1997 |
| DE | 102007025900 | 12/2008 |
| EP | 0 063 640 | 11/1982 |
| EP | 0 088 341 | 9/1983 |
| EP | 0 108 785 | 5/1984 |
| EP | 0 174 162 | 3/1986 |
| EP | 0 227 219 | 7/1987 |
| EP | 0 237 239 | 9/1987 |
| EP | 0 245 872 | 11/1987 |
| EP | 0 257 485 | 3/1988 |
| EP | 0 639 385 | 2/1995 |
| EP | 0 734 721 | 10/1996 |
| EP | 0 769 265 | 4/1997 |
| EP | 1 061 000 | 10/2000 |
| EP | 1 331 020 | 7/2003 |
| EP | 1 471 011 | 10/2004 |
| EP | 1 442 753 | 2/2007 |
| EP | 1 813 293 | 8/2007 |
| EP | 1 977 714 | 10/2008 |
| EP | 2 444 117 | 4/2012 |
| EP | 2 606 930 | 6/2013 |
| EP | 2 671 604 | 12/2013 |
| EP | 2 731 658 | 5/2014 |
| FR | 2 493 149 A | 5/1982 |
| FR | 2 506 162 | 11/1982 |
| FR | 2 782 910 | 3/2000 |
| GB | 123221 | 2/1919 |
| GB | 2 296 182 | 6/1996 |
| GB | 2 333 097 | 7/1999 |
| GB | 2 387 772 | 10/2003 |
| JP | 57-131462 U | 8/1982 |
| JP | 04-99950 | 2/1992 |
| JP | 05-31180 A | 2/1993 |
| JP | 8-81695 A | 3/1996 |
| JP | 09-216661 A | 8/1997 |
| JP | 2000-157630 A | 6/2000 |
| JP | 2002-210011 A | 7/2002 |
| JP | 2002-234567 A | 8/2002 |
| JP | 2002-291906 | 10/2002 |
| JP | 2005-218649 | 8/2005 |
| JP | 2006-182663 A | 7/2006 |
| JP | 2006-223583 A | 8/2006 |
| JP | 2009-006148 | 1/2009 |
| JP | 2009-544450 A | 12/2009 |
| JP | 2011-036691 | 2/2011 |
| JP | 2011-528647 | 11/2011 |
| JP | 2012-020125 | 2/2012 |
| JP | 2013-520287 | 6/2013 |

(56) References Cited

FOREIGN PATENT DOCUMENTS

| | | |
|---|---|---|
| JP | 2013-530794 A | 8/2013 |
| JP | 2014-117461 | 6/2014 |
| JP | 2014-533593 A | 12/2014 |
| JP | 2015-526195 A | 9/2015 |
| JP | 2015-533614 A | 11/2015 |
| JP | 2016-506856 A | 3/2016 |
| JP | 2017-515553 A | 6/2017 |
| RU | 2 246 321 C1 | 2/2005 |
| WO | WO 1983/03975 | 11/1983 |
| WO | WO 1985/05040 | 11/1985 |
| WO | WO 93/20806 | 10/1993 |
| WO | WO 95/07691 | 3/1995 |
| WO | WO 96/35416 | 11/1996 |
| WO | WO 96/38136 | 12/1996 |
| WO | WO 97/19701 | 6/1997 |
| WO | WO 1998/12125 | 3/1998 |
| WO | WO 98/48872 | 11/1998 |
| WO | WO 99/44665 | 9/1999 |
| WO | WO 2001/70199 A1 | 9/2001 |
| WO | WO 2002/05188 | 1/2002 |
| WO | WO 2002/47581 | 6/2002 |
| WO | WO 2002/49544 | 6/2002 |
| WO | WO 2003/015677 | 2/2003 |
| WO | WO 2003/070296 | 8/2003 |
| WO | WO 2004/035129 | 4/2004 |
| WO | WO 2004/112846 | 12/2004 |
| WO | WO 2005/112954 A1 | 12/2005 |
| WO | WO 2005/112974 A2 | 12/2005 |
| WO | WO 2006/007690 | 1/2006 |
| WO | WO 2006/044236 | 4/2006 |
| WO | WO 2006/102756 | 10/2006 |
| WO | WO 2007/008511 | 1/2007 |
| WO | WO 2007/056773 | 5/2007 |
| WO | WO 2007/137056 | 11/2007 |
| WO | WO 2008/014437 | 1/2008 |
| WO | WO 2008/042285 | 4/2008 |
| WO | WO 2008/086631 | 7/2008 |
| WO | WO 2008/089196 | 7/2008 |
| WO | WO 2008/100950 | 8/2008 |
| WO | WO 2008/140807 | 11/2008 |
| WO | WO 2009/002474 | 12/2008 |
| WO | WO 2009/060322 | 5/2009 |
| WO | WO 2009/117135 | 9/2009 |
| WO | WO 2009/123709 | 10/2009 |
| WO | WO 2009/136957 | 11/2009 |
| WO | WO 2009/153224 | 12/2009 |
| WO | WO 2010/002757 | 1/2010 |
| WO | WO 2010/002808 | 1/2010 |
| WO | WO 2010/011616 | 1/2010 |
| WO | WO 2010/034470 | 4/2010 |
| WO | WO 2010/039171 | 4/2010 |
| WO | WO 2010/062589 | 6/2010 |
| WO | WO 2011/012379 | 2/2011 |
| WO | WO 2011/028722 | 3/2011 |
| WO | WO 2011/053924 | 5/2011 |
| WO | WO 2011/106374 | 9/2011 |
| WO | WO 2011/119021 | 9/2011 |
| WO | WO 2012/009456 | 1/2012 |
| WO | WO 2012/118829 | 9/2012 |
| WO | WO 2012/162006 | 11/2012 |
| WO | WO 2013/009998 | 1/2013 |
| WO | WO 2013/023146 | 2/2013 |
| WO | WO 2013/082180 | 6/2013 |
| WO | WO 2012/184716 | 12/2013 |
| WO | WO 2013/192574 | 12/2013 |
| WO | WO 2014/031628 | 2/2014 |
| WO | WO 2014/074419 | 5/2014 |
| WO | WO 2014/074929 | 5/2014 |
| WO | WO 2014/126867 | 8/2014 |
| WO | WO 2014/140949 | 9/2014 |
| WO | WO 2014/159346 | 10/2014 |
| WO | WO 2015/074087 | 5/2015 |
| WO | WO 2015/119940 | 8/2015 |
| WO | WO 2015/120336 | 8/2015 |
| WO | WO 2015/164129 | 10/2015 |
| WO | WO 2015/164134 | 10/2015 |
| WO | WO 2015/168677 | 11/2015 |
| WO | WO 2015/174953 | 11/2015 |
| WO | WO 2016/025775 | 2/2016 |
| WO | WO 2016/182822 | 11/2016 |
| WO | WO 2017/015047 | 1/2017 |
| WO | WO 2017/127364 | 7/2017 |
| WO | WO 2017/127365 | 7/2017 |
| WO | WO 2018/009653 | 1/2018 |
| WO | WO 2018/071717 | 4/2018 |
| WO | WO 2018/204206 | 11/2018 |
| WO | WO 2018/237090 | 12/2018 |
| WO | WO 2018/237122 | 12/2018 |
| WO | WO 2019/178560 | 9/2019 |
| WO | WO 2019/246472 | 12/2019 |
| WO | WO 2020/097366 | 5/2020 |
| WO | WO 2020/251947 | 12/2020 |
| WO | WO 2022/125474 | 6/2022 |

OTHER PUBLICATIONS

Baxter, "Peritoneal Dialysis Patient Connectology," Product Descriptions in 1 page, downloaded Jul. 1, 2011.

Beta Cap II Advertisement from Quinton Instrument Co. (Aug. 1981).

Catheter Connections, "Introducing DualCap," Product Brochure in 1 page, Copyright 2011.

Charney, "Baxter Healthcare InterlinkTM IV Access System" in 1 page, from Handbook of Modern Hospital Safety. Published Mar. 1999.

Conical Fittings: International Standard, "Conical fittings with 6% (Luer) Taper for Syringes, Needles and certain Other Medical Equipment—Part 2: Lock Fittings", Ref. No. ISO 594-2:1998. International Organization for Standardization (Sep. 1, 1998) 2nd ed. (16 pages).

Devine, redacted version of letter from David A. Divine, Esq. of Lee & Hayes, dated May 16, 2011 (3 pages).

Devine, redacted version of letter from David A. Divine, Esq. of Lee & Hayes, dated May 27, 2011 (3 pages).

Hospira, "You Work in Neverland," Lifeshield Product Brochure in 2 pages, Published 2009.

Hyprotek, "Port Protek," Product Brochure in 1 page, downloaded Sep. 19, 2011 from http://www.hyprotek.com/products.html.

ICU Medical Inc., "Oncology System Solutions," Product Brochure in 17 pages, Copyright 2013.

ICU Medical Inc., "Protective Cap," Photographs of Spiros Protective Cap in 2 pages, Product available 2013.

International Invitation to Pay Additional Fees, re PCT Application No. PCT/US19/22610, mailed May 30, 2019.

International Search Report and Written Opinion re PCT Application No. PCT/US19/22610, mailed Jul. 22, 2019.

International Preliminary Report on Patentability re PCT Application No. PCT/US19/22610, issued Oct. 1, 2020.

Menyhay et al., "Disinfection of Needleless Catheter Connectors and Access Ports with Alcohol May Not Prevent Microbial Entry: The Promise of a Novel Antiseptic-Barrier Cap" Infection Control Hospital and Epidemiology, vol. 27, No. 1 (Jan. 2006) (5 pages).

Photographs of the Baxter Minicap (Sep. 1, 1998) (4 pages).

"Small-bore connectors for liquids and gases in healthcare applications—Part : Connectors for intravascular or hypodermic applications," ISO 80369-7, Corrected version dated Dec. 1, 2016 (50 pages).

Antibiotic Lock Therapy Guideline, Stanford Hospital and Clinics, Pharmacy Department Policies and Procedures, issued Jun. 2011.

Otto, Mosby's Pocket Guide to Infusion Therapy. Elsevier Health Sciences, 2004. pp. 65-66. Accessed at: http://books.google.com/books?id=j8T14HwWdS4C&lpg=PP1&pg=PP1#v=onepage&f=false (Year: 2004).

Clave® Needlefree Connector, icumedical, human connections, 2 page brochure. 2012, M1-1065 Rev. 04.

Du. Y, et al. Protein adsorption on polyurethane catheters modified with a novel antithrombin-heparin covalent complex, Journal of Biomedical Materials Research Part A, 2006, 216-225.

Holmer, E. et al. The molecular-weight dependence of the rate-enhancing effect of heparin on the inhibition of thrombin, Factor Xa,

(56) References Cited

OTHER PUBLICATIONS

Factor IXa, Factor XIa, Factor XIIa and kallikrein by antithrombin, Biochem. J. (1981) 193, 395-400.

ICU Medical Antimicrobial Microclave, first sold Jan. 21, 2010, p. 1-2.

ICU Medical SwabPack, top-access bag of disinfecting caps for needlefree connectors, on sale at least as early as Jan. 2012.

Klement, P. et al. Chronic performance of polyurethane catheters covalently coated with ATH complex: A rabbit jugular vein model, Biomaterials, (2006), 27, 5107-5117.

Thread Check Inc., ISO 80369-7 replaces ISO 594-2:1998€, retrieved 2023; ISO 80369-7 published Oct. 2016, https://www.threadcheck. com/isl-80369/technicalinfo#gref (Year: 2016).

V-Link Luer Activated Device, with VitalShield Protective Coating, 2 page brochure, Baxter Dec. 2009.

U.S. Appl. No. 16/882,210, filed May 22, 2020.

Value Plastics, Inc., "Finger Snap Luer Lock Ring (FSLLR)," drawn by Frank Lombardi, May 29, 2011.

Melaiye, et al., "Silver and its application as an antimicrobial agent," Expert Opinion on Therapeutic Patents, 15:2, pp. 125-130, (Year: 2005).

* cited by examiner

900

910

925

920

922

900

910

922

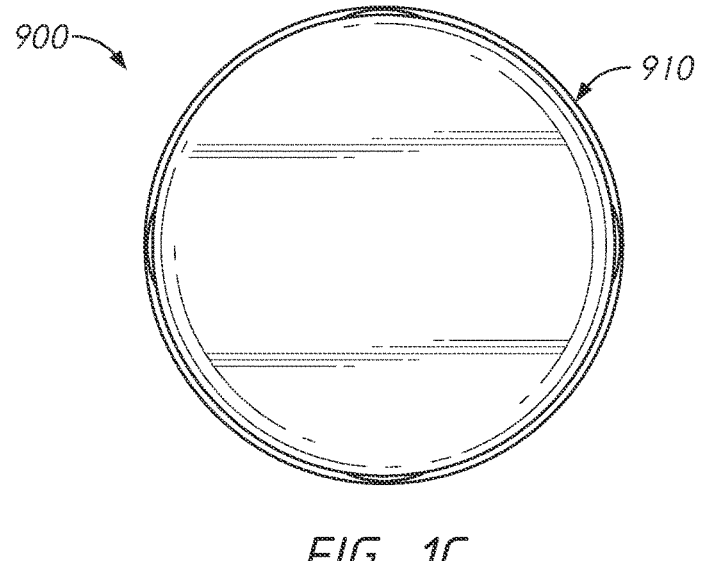
FIG. 1C
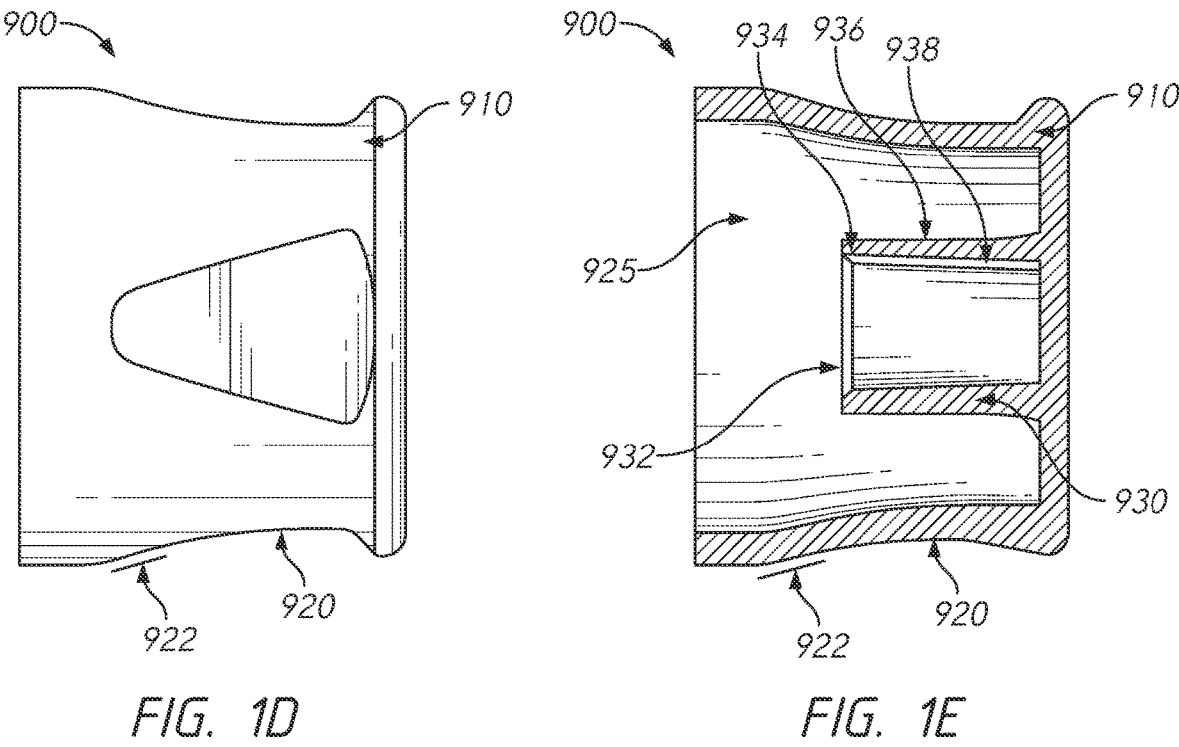
FIG. 1D                    FIG. 1E

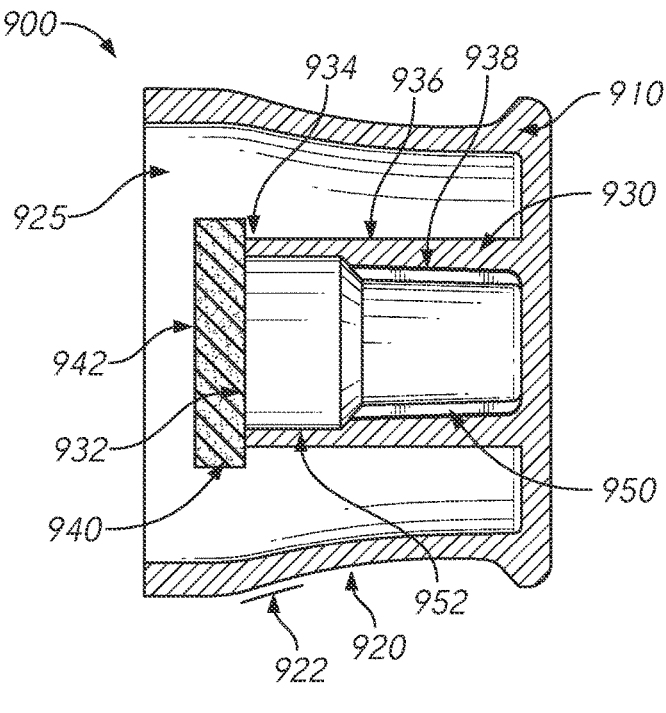
FIG. 3A
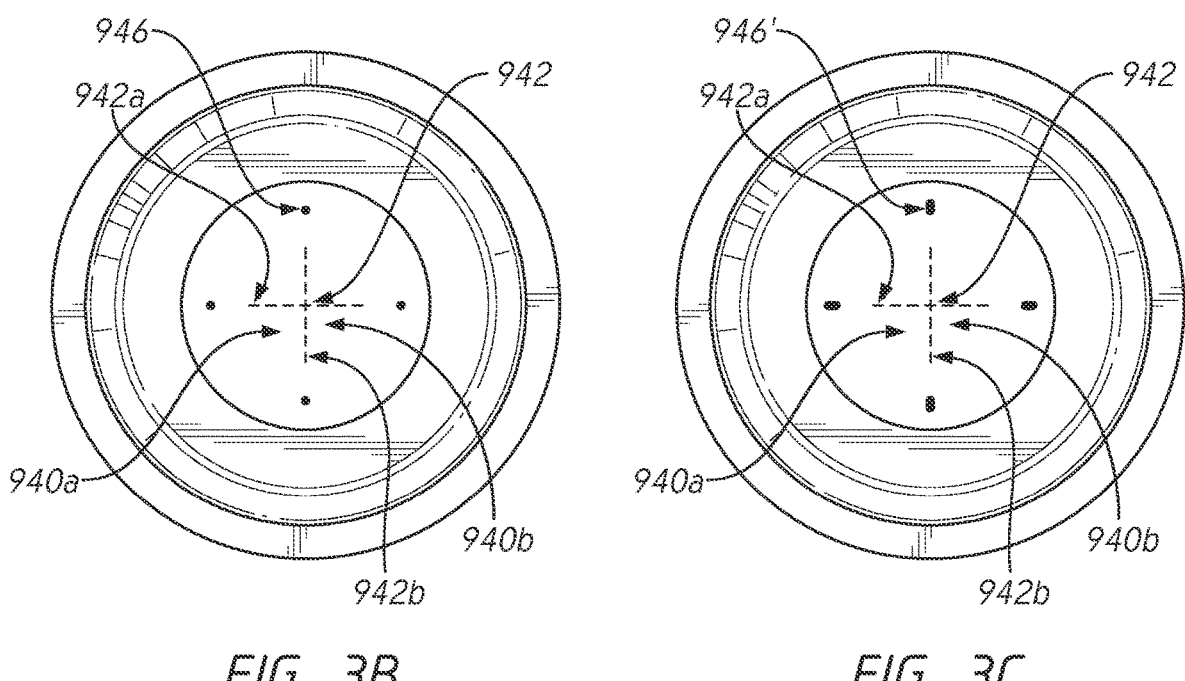
FIG. 3B                                           FIG. 3C

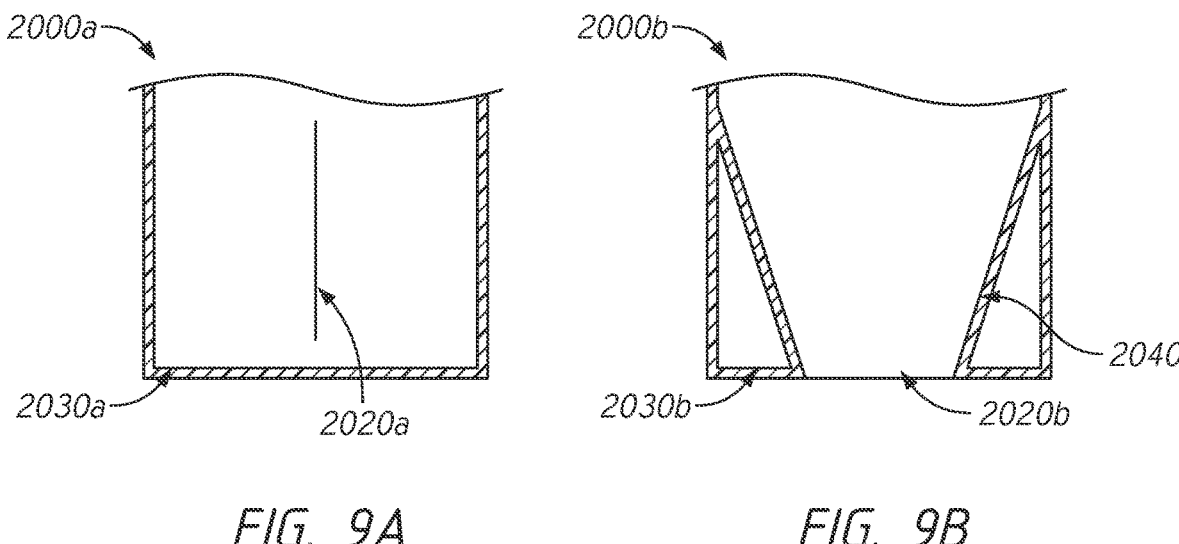
FIG. 9A
FIG. 9B
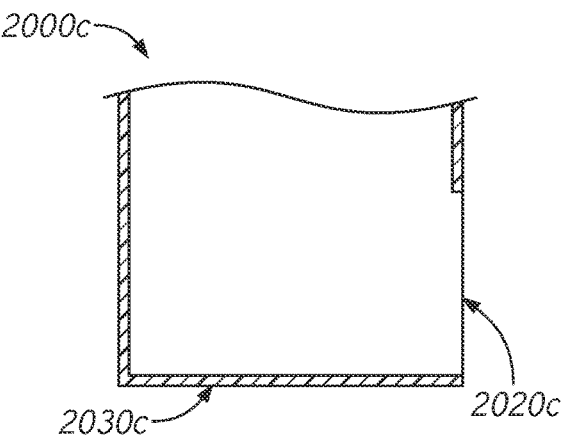
FIG. 9C

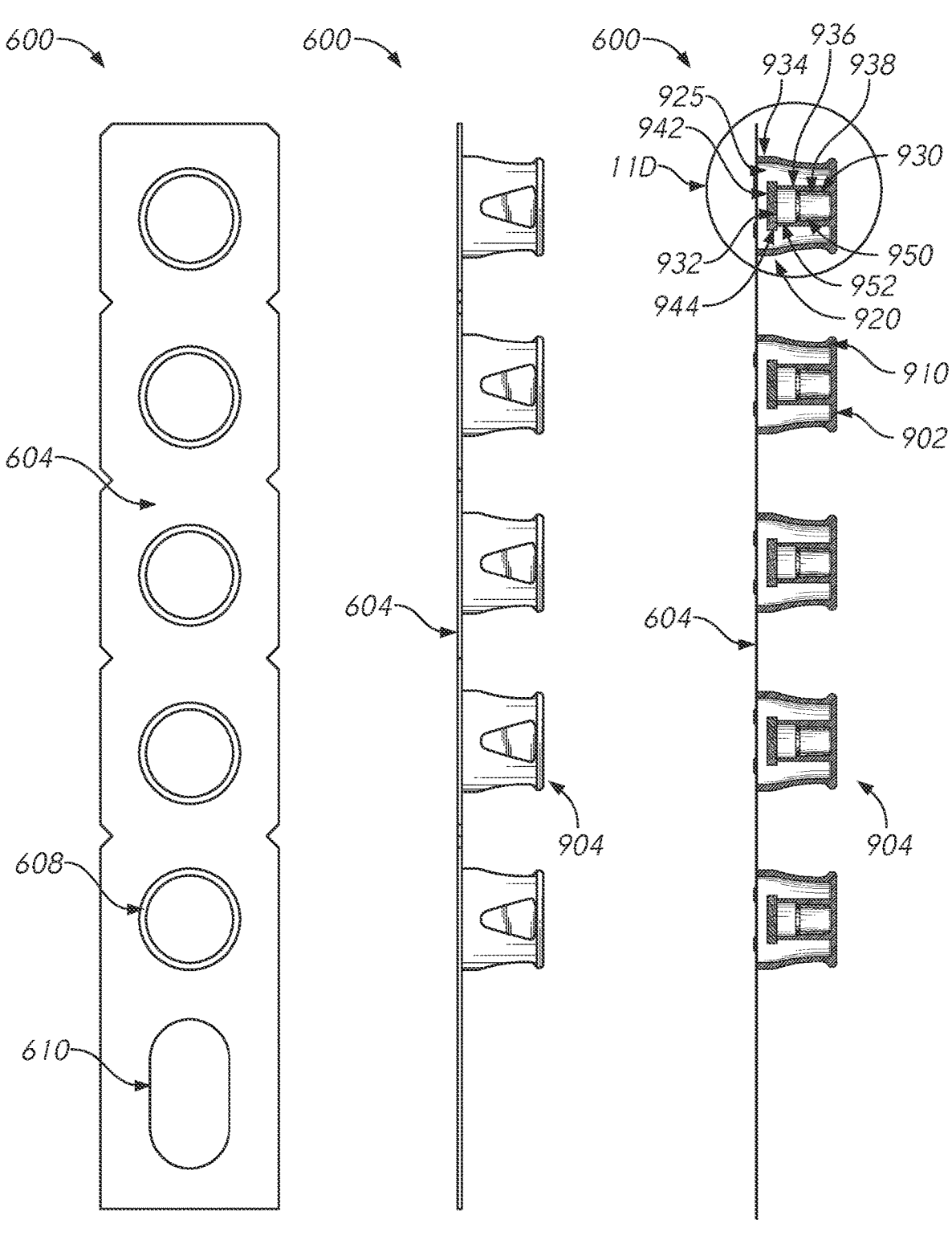
*FIG. 11A*          *FIG. 11B*          *FIG. 11C*

SANITIZING CAPS FOR MEDICAL CONNECTORS

INCORPORATION BY REFERENCE

This application is a continuation application of International Patent Application No. PCT/US2019/022610, filed on Mar. 15, 2019, which claims priority to U.S. Provisional Patent Application No. 62/643,873, filed on Mar. 16, 2018, which are hereby incorporated by reference herein in their entireties, forming part of the present disclosure. Additionally, International Patent Application No. PCT/US2017/056407, filed on Oct. 12, 2017, is hereby incorporated by reference herein in its entirety, forming part of the present disclosure. Any feature, structure, material, method, or step that is described and/or illustrated in any embodiment in the foregoing patent applications can be used with or instead of any feature, structure, material, method, or step that is described and/or illustrated in the following paragraphs of this specification or the accompanying drawings.

BACKGROUND

Field of the Invention

This invention generally relates to caps and, more particularly, to antiseptic caps for use with medical connectors.

Certain embodiments disclosed herein relate to caps for medical connectors and more specifically relate to caps that can be used to disinfect and prevent future contamination of unconnected medical connectors, such as connectors that may be used for fluid flow or for fluid delivery systems.

Description of the Related Art

Catheters are widely used to treat patients requiring a variety of medical procedures. Catheters can either be temporary for short-term use or chronic for long-term treatment. Catheters are commonly inserted into central veins (such as the vena cava) from peripheral vein sites to provide access to a patient's vascular system.

Catheter connections can include, for example, connections of catheters to dialysis machine tubing, to IV line tubing, to infusion ports and to catheter caps, which are used to seal the end of a catheter to protect the sterility of the catheter and prevent fluid loss and/or particle contamination. Catheter connections are most often made utilizing the medical industry's standardized Luer taper fittings. These fittings, which may either be male couplings or female couplings, include a tapered end of standardized dimensions. Coupling is made by the press-fit of mating parts. A threaded lock-fit or other type of securing mechanism is commonly utilized to ensure the integrity of the pressure fit of the Luer fittings. There are also other non-standard fittings that can be used to selectively couple multiple medical-fluid-conveying components together.

Catheter-related bloodstream infections (CRBSI), such as may be caused by microorganisms that enter a patient's body via intravascular catheters, are a significant cause of unnecessary illness, complications, and excess medical costs. A substantial number of such infections occur in U.S. intensive care units annually.

Providing antimicrobial agents in catheters is one approach for reducing these infections. Many of such catheters, however, do not have satisfactory results. Additionally, some microbes have developed resistance to the various antimicrobial agents used in the catheters.

It has been found that the use of antiseptic caps, such as the cap manufactured and sold by Excelsior Medical and ICU Medical, Inc. under the trademark SWABCAP®, greatly reduce the incidence of infections, resulting in, among other things, significant health benefits for patients and vast cost savings. However, there remains a need for alternative cap designs for use with a variety of medical fittings or connectors.

SUMMARY OF THE INVENTION

Disclosed herein are disinfecting caps that can resist the entry of microorganisms into the bloodstream of a patient via fluid flow or fluid delivery systems, such as, for example, medical connectors, needleless injection sites, and/or medical fluid transfer devices. In some embodiments, one or more caps can be configured for use with a medical infusion system with one or more luer connectors, such as a female or male medical connector having a luer fitting. In some embodiments, a cap has a base and a dispensing material, such as an antiseptic material, that is configured to carry a therapeutic liquid or gel, such as a liquid or gel antiseptic or antimicrobial agent (e.g., isopropyl alcohol, or chlorhexidine gluconate, or metallic ions such as silver ions or copper ions, or any other suitable agent or agents for sanitizing or removing contaminants).

In some embodiments, a sanitizing male luer cap can be configured to attach to a medical connector with a male luer having a side wall and a distal tip. The sanitizing luer cap can include a housing comprising an outer wall and a bottom wall, a first chamber enclosed by the outer wall and bottom wall of the housing.

The sanitizing male luer cap can include an inner protrusion extending upwardly from the bottom wall of the housing. The inner protrusion can include an inner and outer wall.

The sanitizing male luer cap can include a second chamber formed by the inner wall of the inner protrusion. The second chamber can be configured to tightly receive the male luer of the medical connector.

The sanitizing male luer cap can include an antiseptic material containing an antiseptic liquid attached to an upper end of the inner protrusion. The antiseptic material can be positioned outside of the second chamber before use.

The sanitizing male luer cap can include a lid configured to enclose the first chamber and resist escape of the antiseptic liquid before use.

The antiseptic material can be configured to wipe the distal tip and side wall of the male luer as the sanitizing male luer cap is advanced onto the male luer of the medical connector.

The sanitizing male luer cap of any of preceding paragraphs and/or any of antiseptic caps described below can include one or more of the following features. The sanitizing male luer cap can be combined with the medical connector. A portion of the antiseptic material can be configured to move into the second chamber as the sanitizing male luer cap is advanced onto the male luer of the medical connector. An upper diameter of the inner protrusion can be smaller than a width of the antiseptic material. A length of a perforation in the antiseptic material can be less than or equal to the largest diameter of the portion of the male luer of the medical connector that is insertable into the inner protrusion, such that the antiseptic material can be configured to form a tight fit around the male luer when the sanitizing male luer cap is attached to the medical connector.

In some embodiments, a sanitizing luer cap can be configured to attach to a medical connector with a male luer end surrounding by a shroud. The sanitizing luer cap can include a housing having a protrusion.

The protrusion can include an opening being configured to receive the male luer end of the medical connector, a distal portion comprising a first inner cross-sectional width, and a proximal portion comprising a second inner cross-sectional width.

The first inner cross-sectional width can be different than the second inner cross-sectional width.

The sanitizing male luer cap can include an antiseptic material being coupled to an outer surface of the protrusion, the antiseptic material being configured to sanitize the male luer end when the sanitizing luer cap is attached to the medical connector.

The sanitizing male luer cap of any of preceding paragraphs and/or any of antiseptic caps described below can include one or more of the following features. The first inner cross-sectional width can be greater than the second inner cross-sectional width. The first inner cross-sectional width can be sized such that the distal portion is configured to receive at least a portion of the antiseptic material and the male luer. The second inner cross-sectional width can be sized to facilitate attachment of the sanitizing luer cap to the male luer end. The antiseptic material can include a diameter greater than the first inner cross-sectional width and the second cross-sectional width. The antiseptic material can be configured to sanitize at least an end face of the mauler luer end. The antiseptic material can include one or more perforations configured to facilitate passage of at least a portion of the male luer end through the antiseptic material. The one or more perforations can include a length less than an outer width of at least the portion of the male luer end. The length of the one or more perforations can be configured to inhibit passage of fluid between the antiseptic material and the male luer end. The antiseptic material can include one or more flap portions. The one or more flap portions can be configured to be at least partially positioned within the distal portion of the protrusion when the sanitizing luer cap is attached to the male luer end. The one or more flap portions can include a compressible material to compress between the distal portion of the protrusion and at least a portion of the male luer end. The one or more flap portions can be configured to facilitate attachment of the sanitizing luer cap to the male luer end. The sanitizing luer cap can be combined with the medical connector.

In some embodiments, an antiseptic cap assembly can include one or more sanitizing male luer caps of any of preceding paragraphs and/or any of antiseptic caps described below and an elongate tubular body or sleeve configured to contain the one or more sanitizing luer caps.

In some embodiments, an antiseptic cap assembly can include one or more sanitizing male luer caps of any of preceding paragraphs and/or any of antiseptic caps described below, a cap holder configured to receive the sanitizing luer cap, and a lid.

BRIEF DESCRIPTION OF THE DRAWINGS

Embodiments will now be described with reference to the following drawings, which are provided by way of example, and not limitation. Like reference numerals indicate identical or functionally similar elements. The sizes and relative proportions of all components and features shown in the drawings form part of this disclosure but should not be interpreted to be part of a claim unless specifically included in such claim.

FIG. 1C is a rear view of the antiseptic cap of FIG. 1A.

FIG. 1D is a side view of the antiseptic cap of FIG. 1A.

FIG. 1E is a side cross-sectional view of the antiseptic cap of FIG. 1A.

FIG. 3A is a side cross-sectional view of an antiseptic cap.

FIG. 3B is a top perspective view of an embodiment of the antiseptic cap of FIG. 3A.

FIG. 3C is a top perspective view of an embodiment of the antiseptic cap of FIG. 3A.

FIG. 9A is a partial front view of an embodiment of a dispensing bag for antiseptic cap holder assemblies.

FIG. 9B is a partial front view of an embodiment of a dispensing bag for antiseptic cap holder assemblies.

FIG. 9C is a partial front view of an embodiment of a dispensing bag for antiseptic cap holder assemblies.

FIG. 11A is a top view of a dispensing device for antiseptic cap holder assemblies.

FIG. 11B is a side view of the dispensing device of FIG. 11A.

FIG. 11C is a side cross-sectional of the dispensing device of FIG. 11A.

DETAILED DESCRIPTION

Figure 1A:
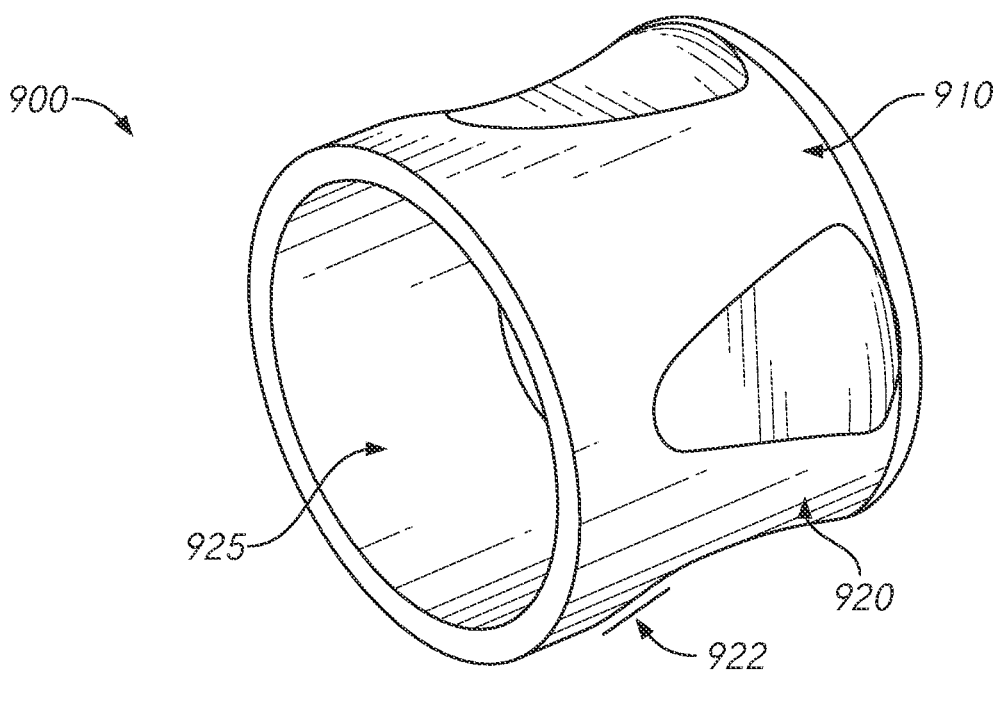
FIG. 1A is a front perspective view of an antiseptic cap.
Figure 1B:
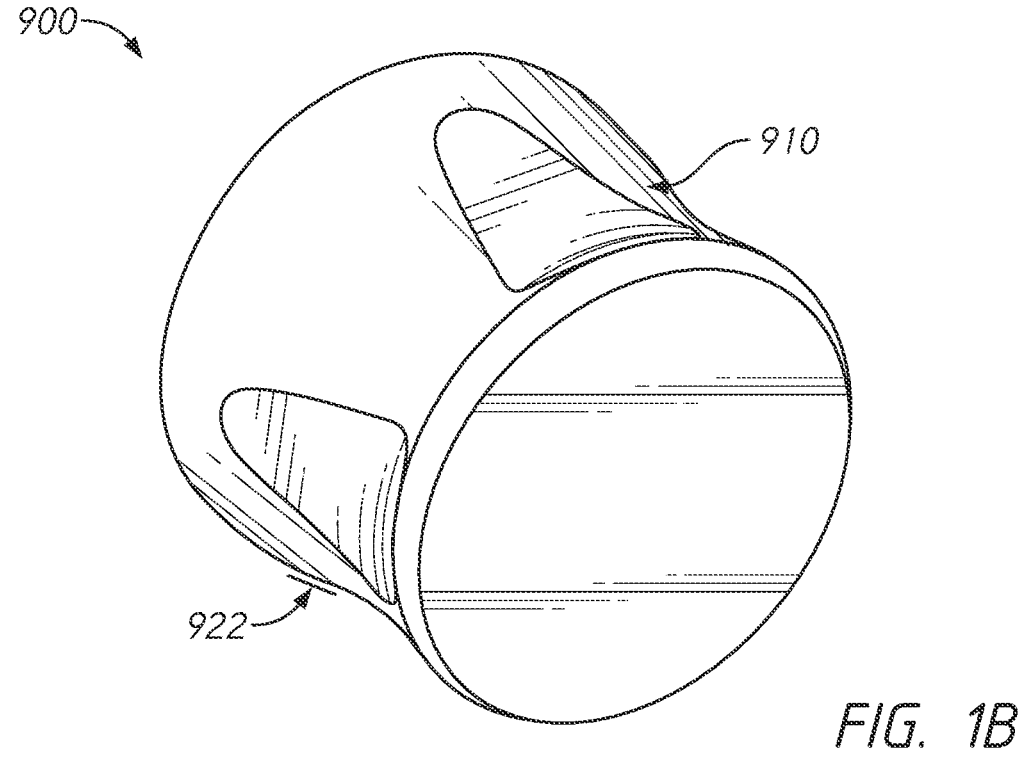
FIG. 1B is a rear perspective view of the antiseptic cap of FIG. 1A.

Various systems, methods, and components can be used in different embodiments of medical caps. Some embodiments are illustrated in the accompanying figures; however, the figures are provided for convenience of illustration only, and should not be interpreted to limit the inventions to the particular combinations of features shown. Rather, any feature, structure, material, step, or component of any embodiment described and/or illustrated in this specification can be used by itself, or with, or instead of, any other feature, structure, material, step, or component of any other embodiment described and/or illustrated in this specification. Nothing in this specification is essential or indispensable. Any of the devices or connections or features that are described and/or illustrated anywhere in this specification can be configured to attach to or protect or sanitize any medical fluid connection points or devices, such as luer connectors which are in compliance with ISO standard 594 or ISO 80369 or any other industry standard that is applicable to medical fluid connectors.

Overview

This disclosure relates to embodiments of a sanitizing cap that can be used to disinfect and/or protect medical connectors. A cap may be used with intravascular connectors associated with a fluid pathway, such as an IV line. All references to any type of connector (e.g., a male luer connector) in this application should be understood to include and disclose any type of medical implement that accomplishes or facilitates storage or transfer of medical fluid or connection of medical fluid lines (e.g., any open or resealable fluid line connector, syringe, catheter connector, vial, vial adapter, pump cartridge or disposable, pharmaceutical compounding component, female connector, blood-line connector, IV bag, catheter inserter, venting or priming cap, etc.). It is contemplated that all features and principles of the inventions disclosed in the specification can be applied to or adapted for use with both luer and non-luer connectors. Thus, all references to male luer connectors or female luer connectors in this specification should be understood also to refer to male connectors or female connectors, respectively, that are not luers.

Fluid pathways, once established, may provide direct access to a patient's blood stream and can be used intermittently to administer medications to a patient. These fluid pathways can have one or more associated medical connectors that can be connected to other medical connectors. In some embodiments, a plurality of corresponding connectors can have male or female connection regions, such as male or female luer connection regions or luer locks. The connection regions can provide a convenient way to connect and disconnect the fluid pathway at various times. When connectors with connection regions are disconnected, one or more caps (e.g., luer caps) can protect the unconnected connectors from possible contamination, such as from accumulation of microbes, debris, or other contaminants on the connecting sides, regions, or surfaces of such connection regions. It can be advantageous for the caps to carry or contain some form of an antiseptic for disinfecting a connection region (e.g., a luer connection region) before and/or while sealing the connector off from possible future contamination from the outside. Any structure, step, material, or component that is illustrated and/or described in any embodiment in this specification can be used with or instead of any other structure, step, material, or component that is illustrated and/or described in any other embodiment in this specification. No structure, step, material, or component is essential or indispensable.

Antiseptic Cap with Outer Shroud

Figure 2:
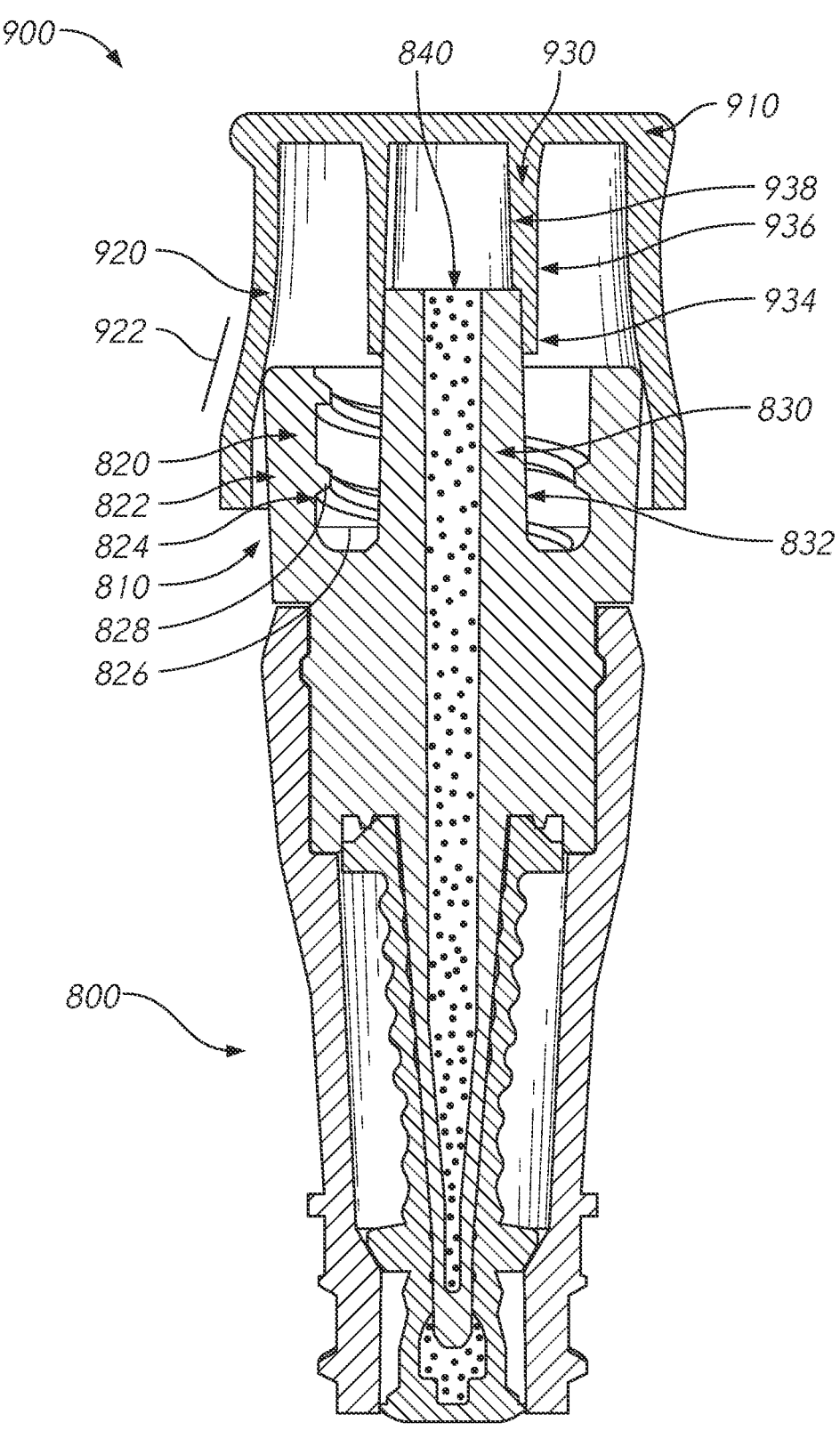
FIG. 2 is a side cross-sectional view of an antiseptic cap attached to a male luer of a medical fluid connector.

FIGS. 1A-1E are various views of an antiseptic cap 900, according to some embodiments. In particular, FIG. 1A is a front perspective view of an antiseptic cap 900, FIGS. 1B-1E are rear perspective, rear, side, and side cross-sectional views of the antiseptic cap 900 of FIG. 1A, respectively, and FIG. 2 is a side cross-sectional view of an antiseptic cap 900 coupled to a male luer connector 800. Additionally, FIGS. 3A-3C and 4 are various views of an antiseptic cap 900 including an antiseptic material 940. Unless otherwise noted, the antiseptic cap 900 as shown in FIGS. 1A-4 may include components that are the same as or generally similar to the components in the figures illustrated and discussed herein. It will be understood that the antiseptic cap 900 shown in FIGS. 1A-4 can be used with any of the embodiments described and/or contemplated herein. It will also be understood that any of the embodiments described and/or contemplated herein can be modified to be used with the antiseptic cap 900 shown in FIGS. 1A-4. As with all embodiments in this specification, any feature, structure, material, method, or step that is described and/or illustrated in the embodiment of FIGS. 1A-1E can be used with or instead of any feature, structure, material, method, or step that is described and/or illustrated in any other embodiment of this specification.

Figure 4:
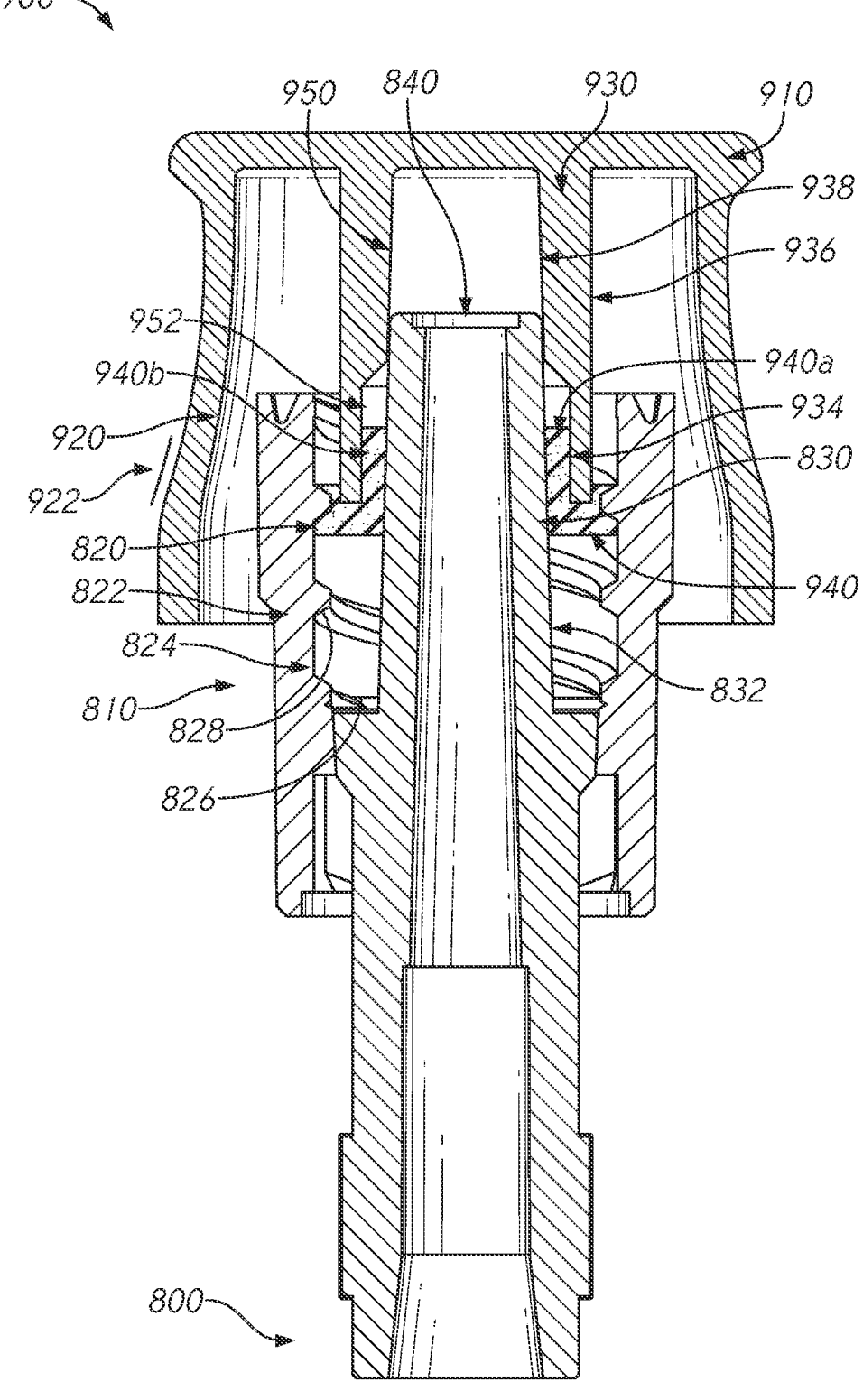
FIG. 4 is a side cross-sectional view of an antiseptic cap attached to a male luer of a medical fluid connector.

As shown in the Figures, the cap 900 comprises a housing 910 including a first chamber 925. The first chamber 925 can be configured to be removably attached to a medical connector 800, as illustrated in FIGS. 2 and 4. For example, in some embodiments, the first chamber 925 can comprise an interior surface configured to interact with a portion of a medical connector 800, such as, for example, an end region or male end of a medical connector, one or more threads of a medical connector, and/or one or more other features of a medical connector. It will be understood that any feature, structure, material, step, or component of any embodiment described and/or illustrated herein (such as the first chamber 84 of antiseptic cap 82 of FIGS. 1A-1H of International Patent Application No. PCT/US2017/056407) can be used with or instead of any other feature, structure, material, step, or component of any embodiment of antiseptic cap 900 of FIGS. 1A-4.

As shown, and in some embodiments, the housing 910 includes a skirt 920 and a protrusion 930. As illustrated, in some embodiments, the skirt 920 and the protrusion 930 can be positioned and/or oriented such that their respective central longitudinal axes are generally collinear, such as with the protrusion 930 positioned within the skirt 920. As shown, and in some embodiments, the protrusion 930 has an opening or recess 932 (see FIG. 1E) comprising a distal lip or rim 934 that can be proximally recessed within the skirt 920, such that the exterior surface of the cap 900 extends further in the distal direction than the distal-most tip of the protrusion 930. In some embodiments, the protrusion 930 can extend upwardly from the bottom wall of the housing 910 and can include an inner and outer wall.

As shown in FIGS. 1A-1E, the first chamber 925 can receive and/or house any suitable feature. For example, in some embodiments, the cap 900 comprises a fluid-delivery material, such as an antiseptic material 940 shown in FIGS. 3A-3C and 4 described in further detail herein. FIG. 2 shows a cross-sectional view of an embodiment of cap 900 without an antiseptic material 940 that is coupled to a medical connector 800.

FIG. 2 illustrates an embodiment of a cap 900 coupled to a male luer connector 800. As shown, the male luer connector 800 comprises a connector housing 810. In some embodiments, the connector housing 810 includes a shroud or collar 820 having an exterior surface 822 and an interior surface 824. The interior surface 824 can comprise a connection interface 826. The connection interface 826, in some instances, can include threading 828. The connector housing 810 may include a male luer 830 having an exterior surface 832. As shown, and in some embodiments, the male luer 830 includes a fluid passageway 840.

With further reference to FIGS. 2 and 4, when the cap 900 is coupled to the male luer connector 800 as shown, the male luer 830 is received by the opening or recess 932 of the protrusion 930. In some embodiments, during or after coupling, an inner surface 938 of the protrusion 930 is moved adjacent to or into contact with at least a portion of the exterior surface 832 of the male luer 830 such that at least a portion of the male luer 830 is positioned within and/or secured to the protrusion 930. At least a portion of the male luer 830, in some instances, is positioned within a chamber of the protrusion 930, as illustrated in FIGS. 2 and 4. For example, the chamber of the protrusion 930 can be formed by the inner wall of the protrusion 930 and is configured to tightly receive at least a portion of the male luer. In some embodiments, as illustrated, when the cap 900 is coupled to the male luer 830, the male luer 830 can be sealed, no longer in communication with the environment, which can resist vaporization of liquid contents within the male luer 830 into the environment and/or ingress of environmental contaminants into the male luer 830. As illustrated in FIG. 2, in some embodiments, the interior of the protrusion 930 is empty or devoid of a fluid-delivery material or therapeutic fluid or antiseptic and/or there is no structure or material between the male luer 830 and the proximal end and/or distal end of the interior of the protrusion 930 when the cap 900 is attached to the male luer connector 800. As illustrated, in some embodiments, no structure of the cap 900 is configured to enter into or contact the fluid passageway 840 of the connector 800 when the cap 900 is connected to the connector 800.

In some embodiments, as illustrated in FIGS. 2 and 4, the skirt 920 contacts or covers or overlays against or extends across at least a portion of the exterior surface 822 of an end region, such as an end region of the collar 820 of the connector 800. In some embodiments, the skirt 920 can include a tapered region, such as a tapered region 922 near a distal end of the cap 900. In some embodiments, the cross-sectional width of the tapered region 922 can increase in a proximal-to-distal direction. In the illustrated embodiments, the tapered region 922 facilitates coupling between the cap 900 and the male luer connector 800. The tapered region 922 can facilitate coupling between the skirt 920 and the collar 820. For example, the cross-sectional width of the skirt 920 decreases as the end of the connector 800 is inserted in a proximal direction into the distal end of the skirt 920 towards a proximal end of the skirt 920, thereby increasing the tightness of the connection or grip or attachment between cap 900 and the connector 800.

In some embodiments, the skirt 920 may not include a tapered region 822. As illustrated in FIG. 2, in some embodiments, the interior face of the exterior wall of the cap 900 frictionally contacts or attaches to the connector on an exterior surface of the connector, and/or the interior face and/or the exterior face of the exterior wall of the cap 900 does not contact or attach in any threaded region or in any region within the interior of the collar or shroud of the connector 800. As shown, the outer cross-sectional width of the distal end of the cap 900 can be larger than the outer cross-sectional width of the portion of the connector 800 to which the cap 900 is configured to attach. In some embodiments, as illustrated, the cap 900 can be attached to and/or removed from the connector 800 by axially or longitudinally pushing the cap 900 onto or pulling the cap 900 away from the connector 800 in a single distal or proximal direction, without requiring rotation or screwing of the cap 900 onto or into the connector 800. In some embodiments, as shown in FIGS. 1E and 3A, the exterior surface of the cap 900 has a curved or non-straight sidewall, which can facilitate securely grasping the cap 900 with the fingers in a slide-resistant manner. As shown in FIGS. 1A-1D, in some embodiments the exterior side surface of the cap 900 can comprise one or more generally flat regions to facility grasping the cap 900 with the fingers. In some embodiments, as illustrated, the proximal base of the cap 900 can comprise a radially outwardly extending surface that forms a lip to provide a region that resists sliding of the fingers when the cap 900 is removed from the connector 800 by axially or longitudinally pulling the cap 900 away from the connector 800. As shown in FIGS. 1E and 3A, the interior face of the exterior wall of the cap 900 can be smooth, without substantial protrusions or recesses or threads.

Antiseptic Cap with an Antiseptic Material

FIGS. 3A-3C are various views of an antiseptic cap 900 including an antiseptic material 940, according to some embodiments. In particular, FIG. 3A is a side cross-sectional view of an antiseptic cap 900, FIGS. 3B and 3C are top views of various embodiments of the antiseptic cap 900 of FIG. 3A, and FIG. 4 is a side cross-sectional view of an antiseptic cap 900 coupled to a male luer connector 800. Unless otherwise noted, the antiseptic cap 900 as shown in FIGS. 3A-4 may include components that are the same as or generally similar to the components in the figures illustrated and discussed herein. It will be understood that the antiseptic cap 900 shown in FIGS. 3A-4 can be used with any of the embodiments described and/or contemplated throughout this specification. It will also be understood that any of the embodiments described and/or contemplated herein can be modified to be used with the antiseptic cap 900 shown in FIGS. 3A-4. As with all embodiments in this specification, any feature, structure, material, method, or step that is described and/or illustrated in the embodiment of FIGS. 3A-4 can be used with or instead of any feature, structure, material, method, or step that is described and/or illustrated in any other embodiment of this specification.

Embodiments of Antiseptic Materials

As shown in FIGS. 3A-4, the cap 900 can comprises an antiseptic material 940. The antiseptic material 940 can be configured to be attached to a portion of the cap 900. In some embodiments, the antiseptic material 940 is attached partially or entirely within the first chamber 925, such as to an outer surface 936 of the protrusion 930, and/or does not attached to an inner surface 938 of the protrusion, and/or is connected to the protrusion 930 such that at least a portion of the antiseptic material 940 overhangs or extends distally beyond the lip or rim 934 of the protrusion 930. For example, as shown in FIGS. 3A and 4, a proximal face of the antiseptic material 940 may be configured to interact with and/or attach to a portion of a protrusion 930 of the cap 900, such as, for example, a distal end face of the protrusion 930. In some embodiments, the antiseptic material 940 and the protrusion 930 can be positioned and/or oriented such that their respective central longitudinal axes are generally collinear when the antiseptic material 940 is positioned on the protrusion 930. The antiseptic material 940 may be the same as or generally similar to any liquid-dispensing, fluid delivery, absorbent, and/or antiseptic material discussed and/or illustrated anywhere in International Patent Application No. PCT/US2017/056407.

A distal end face of the antiseptic material 940 may be positioned in a proximal direction from a distal end of the cap 900, such that the antiseptic material 940 is recessed proximally within the cap 900 when the cap 900 is inverted and resting on a horizontal surface, as shown in FIGS. 3B and 3C, to thereby resist contact between the antiseptic material 940 and microbes or other contaminants before use or between uses, when the cap 900 is inverted. In some embodiments, the antiseptic material 940 can be made of a deformable material such as foam, sponge, cross-linked matrix, gauze, cloth, woven or non-woven textile, etc. In some embodiments, at least a portion of the antiseptic material 940 can be stretched along an outer surface 936 of the protrusion 930.

A proximal end face of the antiseptic material 940 can be spaced distally from the interior surface of the base of the cap 900, such as to form a void between the proximal end face of the antiseptic material 940 and the interior surface of the base of the cap 900. As illustrated, the exterior surface of the base of the cap 900 can be flat and/or planar, and/or substantially flat and/or substantially planar so as to permit the cap 900 to be positioned on a horizontal surface without tipping over or rolling away.

As shown in FIGS. 3B and 3C, and in some embodiments, the antiseptic material 940 can include an access region, such as a tear point, part line, separation point, or opening 942, for facilitating antiseptic contacting and cleaning of one or more portions of a male luer connector 800 (e.g., a male luer 830). The antiseptic material 940, in some embodiments, may comprise one or more features configured to allow the user to create and/or expand the opening 942 to allow a male luer 830 of the connector 800 to gain access to an internal cavity of the protrusion 930. The antiseptic material 940 can be made of a deformable material for coupling with a connection region (e.g., the male luer 830). In some embodiments, the antiseptic material 940 may include a resting or initial configuration in which the opening 942 does not exist or in which the opening 942 can have a smaller diameter than the outer diameter of a coupling portion of a connection region (e.g. a male luer 830). For example, the opening 942, when the antiseptic material 940 is in the resting or initial configuration, is substantially closed (as illustrated in FIGS. 3B and 3C) or does not exist; and the opening 942, when the antiseptic material 940 is in an engaged or subsequent configuration, changes to permit a male luer to extend through the antiseptic material 940 (as illustrated in FIG. 4). The antiseptic material 940 can transition from the resting configuration to the engaged configuration as the cap 900 is removably attached to a medical connector 800. For example, at least a portion of the medical connector 800 (e.g., the male luer 830) may move at least a portion of the antiseptic material 940 from the resting configuration to the engaged configuration.

For example, in some embodiments, the antiseptic material 940 may comprise one or more separation-facilitating features, such as one or more part lines, notches, perforations, and/or scores 942a, 942b, that can help to form, create, and/or define the opening 942. The one or more separation-facilitating features, such as perforations 942a, 942b, may allow the male luer 830 to pass through the antiseptic material 940 as the cap 900 is applied onto the connector 800. The length of the one or more separation-facilitating features, such as perforations 942a, 942b, may be different depending upon the features desired in a particular product. For example, the length of the one or more perforations 942a, 942b may be about equal to or greater than a diameter or width of a coupling male luer 830. In this manner, the length of the one or more perforations 942a, 942b may permit the male luer 830 to couple with the cap 900 without requiring the male luer 830 to puncture or tear the antiseptic material 940 and/or expand or stretch the length of the one or more perforations 942a, 942b when coupling to the cap 900. In some instances, the length of the one or more protrusions 942a, 942b may be about equal to or greater than any diameter or width along the length of the male luer 830. The length of the one or more perforations 942a, 942b, in some instances, may be about equal to or smaller than an outer diameter or width of the male luer 830, which may cause radial or transverse stretching or expanding of the antiseptic material 940 as the male luer 830 is inserted into the protrusion 930. In this manner, the antiseptic material 940 may closely interact with the male luer 830 in substantially continuous contact axially along and/or circumferentially around the male luer 830 (e.g., in a tight and/or close-fitting interference fit with the male luer 830) as the male luer 830 passes through the one or more perforations 942a, 972b and the opening 942 to couple with the cap 900. For example, the length of the one or more perforations 942a, 942b may be less than or about equal to the largest diameter along the portion of the male luer 830 that is configured to be inserted through the antiseptic material 940. In some embodiments, providing perforations 942a, 942b with such smaller lengths can help to avoid the presence of gaps between the antiseptic material 940 and the male luer 830 as the male luer 830 couples with the cap 900. The tight circumferential fit or absence of gaps between the inserted male luer 830 and the protrusion 930 may advantageously inhibit and/or prevent an antiseptic solution and/or gas located within an interior cavity of the protrusion 930 from evaporating, venting, and/or escaping through the antiseptic material 940, and/or can prevent undesirable or harmful material, such as bacteria, viruses, or other microbes, from entering through such gaps into the interior of the protrusion 930 and hence into the medical fluid.

In some embodiments, the one or more perforations 942a, 942b extend completely through the antiseptic material 940 so that a coupling male luer 830 may couple with the cap 900 without requiring the male luer 830 to puncture the antiseptic material 940. In some embodiments, the one or more separation-facilitating features may not extend completely through the antiseptic material 940, and the male luer 830 may need to puncture, tear, and/or separate at least one portion of the antiseptic material 940 from another portion of the antiseptic material 940 in order to access the internal cavity of the protrusion. While FIGS. 3B and 3C illustrate the antiseptic material 940 as comprising two perforations, any number of separation-facilitating features capable of forming and/or defining the opening 942 of the antiseptic material 940 may be utilized. For example, the antiseptic material 940 may comprise one perforation, three perforations, four perforations, or any other number of perforations configured to form and/or define the opening 942.

As illustrated in FIGS. 3B and 3C, in some embodiments, the one or more separation-facilitating features may help to form one or more moving portions, such as one or more leaves, petals, or flap portions 940a, 940b of the antiseptic material 940. The flap portions 940a, 940b may be configured to move from a generally planar orientation as the cap 900 is applied to the connector 800 to a generally proximally extending orientation. The flap portions 940a, 940b may substantially close the opening 942, when the antiseptic material 940 is in the initial or resting configuration, and may substantially widen the opening 942, when the antiseptic material 940 is in the engaged or subsequent configuration. Upon application of the connector 800 to the cap 900, the one or more flap portions 940a, 940b may be configured to interact with and facilitate cleaning of a male luer 830 of the connector 800. While FIGS. 3B and 3C illustrate the antiseptic material 940 as comprising six flap portions, any number of flap portions may be utilized.

In some embodiments, the antiseptic material 940 can be made of a compressible, deformable, and/or resilient material such as foam or textile or cloth or gauze. However, any suitable material can be used as the antiseptic material 940. In some embodiments, the antiseptic material 940 (or any other fluid-delivery or liquid-dispensing material disclosed or illustrated elsewhere in the text or drawings of International Patent Application No. PCT/US2017/056407) is configured to carry and deliver a therapeutic liquid or gel, such as a liquid or gel antiseptic or antimicrobial agent. For example, the therapeutic liquid or gel can be isopropyl alcohol, or chlorhexidine gluconate, and/or metallic ions such as silver ions or copper ions, and/or any other suitable agent or agents for sanitizing, washing, and/or removing contaminants.

Example Methods of Attaching Embodiments of the Antiseptic Material

The antiseptic material 940 may be attached to one or more portions of the cap 900 (e.g., the protrusion 930). The antiseptic material 940 may be attached in any suitable way, such as utilizing one or more of the various methods described herein.

In some embodiments, the antiseptic material 940 may be placed in general lateral alignment with a distal face of the protrusion 930. For example, a proximal face of the antiseptic material 940 may be positioned and/or oriented on top of the protrusion 930 such that their respective central longitudinal axes are generally collinear, as illustrated in FIGS. 3A-3C and 4. In some embodiments, the antiseptic material 940 and the outer surface 936 of the protrusion 930 may be circular (as illustrated); however, the antiseptic material 940 and the outer surface 936 may comprise any shape suitable. As shown, in some embodiments, the antiseptic material 940 can be in the general shape of a circle that is about the same size as or slightly wider than a generally circular distal tip of the protrusion 930. In some embodiments, the antiseptic material 940 can be in a shape in which its longitudinal length is less than its diameter or width. For example, as illustrated, the antiseptic material 940 can be in the form of a disc, thin cylinder, or sheet. One or more edges or other regions of the antiseptic material 940 may be bonded, sealed, and/or attached to the distal face of the protrusion 930 to cover the opening 932 of the protrusion 930. FIGS. 3B and 3C each show various embodiments of the antiseptic material 940 having one or more attachment portions 946, 946' located proximate to an opening 942. The one or more attachment portions 946, 946' may be configured to facilitate attachment of the antiseptic material 940 to the protrusion 930. While FIGS. 3B and 3C illustrate the antiseptic material 940 as comprising four attachment portions 946, 946', any number of attachment portions 946, 946' capable of facilitating the attachment of the antiseptic material 940 to the protrusion 930 may be utilized.

Any suitable method may be used to bond, seal, and/or attach the antiseptic material 940 to the protrusion 930 via the one or more attachment portions 946, 946'. For example, in some embodiments, heat staking and/or thermal bonding may be used to bond, melt, and/or seal at least the one or more attachment portions 946, 946' to and/or around a portion (e.g., an edge) of a perimeter of the protrusion 930. Thermal bonding may be performed using standard heat bonding or sealing technology, such as impulse, induction, conduction, radiant, or other heat bonding or sealing techniques. Additionally or alternatively, the one or more attachment portions 946, 946' may be sealed by utilizing sonic welding, an adhesive bond, or by any suitable mechanical or friction connection, such as a snap-fit. In some embodiments, an attachment agent, such as glue or solvent or adhesive, or any other suitable agent may be used.

With reference to FIG. 3B, for example, the one or more attachment portions 946 may comprise a substantially circular and/or dot shape. The antiseptic material 940 may be placed on top of a distal face of the protrusion 930 to be attached. The dot-shaped attachment portions 946 may be made or incorporated along an outer perimeter of the protrusion 930. Additionally or alternatively, with reference to FIG. 3C, the one or more attachment portions 946' may comprise a generally elongated shape to facilitate attachment of the antiseptic material 940 to the protrusion 930 by requiring less precision in the locating of the antiseptic material 940 on the protrusion 930 and/or less precision in the forming of the attachment portions 946 attaching the antiseptic material 940 to the protrusion 930. The generally elongated shape of attachment portion 946', in some instances, can provide a larger attachment surface area, relative to the dot-shaped attachment portion 946, to increase the chances of ensuring that the one or more attachment portions 946' engages with and/or attaches to the distal face of the protrusion 930. For example, the generally elongated shape of the one or more attachment portions 946' may increase the efficiency of attaching the antiseptic material 940 to the protrusion 930, for example, even in an instance where the antiseptic material 940 is slightly off-center from the protrusion 930. In some embodiments, the antiseptic material 940 may incorporate a combination of the dot-shaped attachment portions 946 and the generally elongated attachment portions 946'.

Embodiments of Caps with Varying Inner Cross-Sectional Widths of the Protrusion

As illustrated in FIGS. 3A and 4, the protrusion 930 can be configured to receive and/or engage at least a portion of the male luer 830 of the connector 800. In some embodiments, the inner surface 938 of the protrusion 930 can include a tapered region. For example, a cross-sectional width of the inner surface 938 of the protrusion 930 can change (e.g., increase or decrease) in a distal-to-proximal direction. The tapered region may facilitate coupling between the cap 900 and male luer 830 of the male luer connector 800. The tapered region, in some instances, may comprise a gradual change in cross-sectional width of the inner surface 938.

Additionally or alternatively, the inner surface 938 may comprise one or more portions with varying inner cross-sectional widths, as shown in FIGS. 3A and 4. For example, as illustrated, the protrusion 930 may comprise a proximal portion 950 that comprises a narrower inner cross-sectional width than a distal portion 952 of the protrusion 930. The distal portion 952 may be spaced distally from the proximal portion 950.

In some embodiments, as illustrated in FIG. 4, the varying diameters of the wider distal portion 952 and the narrower proximal portion 950 may be sized and configured to facilitate coupling between the protrusion 930 and the male luer 830 when the cap 900 is attached to a medical connector 800. The inner cross-sectional width of the distal portion 952 of the protrusion 930 can be larger than the outer cross-sectional width of the exterior surface 832 of the male luer 830 to which the cap 900 is configured to attach. For example, the cross-sectional width of the inner surface 938 may decrease as an end of the male luer 830 is inserted in a proximal direction from the distal portion 952 towards the proximal portion 950, thereby increasing the tightness of the connection, grip, and/or attachment between the protrusion 930 and the male luer 830. In some instances, the distal portion 952 may be sized and configured to receive the male luer 830 and one or more moving portions, such as one or more flap portions 940a, 940b, of the antiseptic material 940 in the generally proximally extending orientation (e.g., as shown in FIG. 4) when the cap 900 is attached to the connector 800.

In some embodiments, as illustrated in FIGS. 3A-4, the varying diameters of the wider distal portion 952 and the narrower proximal portion 950 may be sized and configured to facilitate coupling between the protrusion 930 and the antiseptic material 940. The inner cross-sectional width of the distal portion 952 of the protrusion 930 can be smaller than the outer cross-sectional width of the antiseptic material 940 to which the protrusion 930 is configured to attach, thereby facilitating attachment of the antiseptic material 940 to the protrusion 930 as discussed herein.

Example Methods of Applying Embodiments of the Cap

The cap 900 can be attached to and/or removed from the connector 800 by axially or longitudinally pushing the cap 900 onto or pulling the cap 900 away from the connector 800. With reference to FIG. 4, when the cap 900 is coupled to the male luer connector 800, as shown, the male luer 830 is received by the opening 942 of the antiseptic material 940 (e.g., into an opening 942 of fixed size or into an opening 942 with a size that increases upon insertion of the male luer 830, and/or into an opening 942 that is created by the pressure of the male luer 830 against the antiseptic material 940 which forms the opening 942). As the male luer is received into the opening 942, the antiseptic material 940 can be configured to contact, clean, wipe, and/or sanitize an exterior surface of the male luer 830. For example, when the cap 900 is coupled to the male luer 830, an end face of the male luer 830 can be pressed against and placed in fluid communication with the antiseptic material 940 to facilitate cleaning and sanitization of the end face of the male luer 830 (e.g., the fluid passageway 840) by the antiseptic material 940. The antiseptic material 940, in some instances, can be configured to wipe a distal tip and/or side wall of the male luer 830 as the cap 900 is advanced onto the male luer 830. As illustrated in FIG. 4, when the male luer 830 is inserted into the protrusion 930 and the one or more moving portions (e.g., flap portions 940a, 940b) move into the generally proximally extending orientation, the one or more moving portions of the antiseptic material 940 can be sufficiently thick to essentially completely or generally fill a void between an exterior surface of the male luer 830 and an inner surface 938 of the distal portion 952 of the protrusion 930. In some embodiments, the one or more flap portions 940a, 940b can be configured to compress between these surfaces, exerting a generally constant and generally consistent force against the exterior wall of the male luer 830 that is inserted into the protrusion 930.

The distal portion 952 may be sized and configured to receive one or more flap portions 940a, 940b of the antiseptic material 940 when the male luer 830 of the connector 800 is attached to the cap 900. As shown in FIG. 4, the one or more flap portions 940a, 940b of the antiseptic material 940 can frictionally contact or engage the connector 800 on an exterior surface of the male luer 830 and/or the interior surface 938 of the distal portion 952 of the protrusion 930 to more tightly grip the male luer 830. For example, as the male luer 830 is inserted into the cap 900, one or more flap portions 940a, 940b of the antiseptic material 940 can contact the male luer 830. During and/or after coupling, advancing the male luer 830 into the protrusion 930 may move the one or more portions 940a, 940b adjacent to or into contact with at least a portion of the inner surface 938 of the distal portion 952 such that at least a portion of the one or more flap portions 940a, 940b is positioned within and/or secured between the inner surface 938 of the distal portion 952 and the male luer 830. In some embodiments, the one or more portions 940a, 940b may be configured to fold into the distal portion 952 of the protrusion 930. The distal portion 952 can be sized and configured to receive the one or more portion 940a, 940b and permit the cap 900 to more tightly grip the male luer of the connector 800 when attached, as the connector 800 is advanced into the protrusion 930. In some embodiments, at least a portion of the antiseptic material 940 is configured to move into a chamber of the protrusion 930 as the cap 900 is advanced onto the male luer 830.

During and/or after coupling, an inner surface 938 of the proximal portion 950 of the protrusion 930 can be moved adjacent to or can come into contact with at least a portion of the male luer 830 such that at least a portion of the male luer 830 is positioned within and/or secured to the proximal portion 950. As illustrated in FIG. 4, in some embodiments, the proximal portion 950 of the protrusion 930 is empty or devoid of a fluid-delivery material or therapeutic fluid or antiseptic and/or there is no structure or material between the male luer 830 and the proximal portion 950 of the protrusion 930 when the cap 900 is attached to the male luer connector 800. In some embodiments, by securing the protrusion 930 or the positioning of the male luer 830 within the proximal portion 950 and away from the antiseptic material 940, the therapeutic liquid or gel that is carried by the antiseptic material 940 or otherwise present in the cap 900 is not forced to enter into the fluid passageway 840 of the male luer 830.

In some embodiments, as shown in FIG. 4, when the cap 900 is coupled to the connector 800, the antiseptic material 940 of the cap 900 is positioned in direct contact with at least a portion of the collar 820 of the male luer connector 800. In some embodiments, the antiseptic material 940 is in direct contact with the threading 828 of the collar 820. In some embodiments, the antiseptic material 940 is in direct contact with the exterior surface 832 of the male luer 830. In some embodiments, the antiseptic material 940 is spaced away from the male luer connector 800 and/or the connection interface 826. In some embodiments, when the antiseptic material 940 comes into direct contact with the collar 820 of the male luer connector 800, the antiseptic material 940 contacts, cleans, wipes, and/or sanitizes the collar 820. In some embodiments, the antiseptic material 940 contacts, cleans, wipes, and/or sanitizes the threading 828 of the collar 820. In some embodiments, when the antiseptic material 940 comes into direct contact with the exterior surface 832 of the male luer 830, the antiseptic material 940 contacts, cleans, wipes, and/or sanitizes the male luer 830.

Cleaning or wiping, as utilized herein, can include killing and/or removing one or more substances or organisms from a surface of a medical connector in an amount or to a degree that provides a clinically significant therapeutic effect, such as killing and/or removing one or more substances or organisms in an amount configured to avoid or to resist an adverse medical consequence in a patient, such as a disease or an infection or some other undesirable medical outcome.

Any or all of the steps of cleaning and/or sanitizing can include wiping along a surface to be cleaned and/or sanitized during connection. In some embodiments, as shown in FIG. 4, the antiseptic material can simultaneously clean and/or sanitize the exterior surface of the male luer 830 and the interior surface of the shroud or collar 820, such as by simultaneously contacting and/or wiping the exterior surface of the male luer 830 and the interior surface of the shroud or collar 820. As illustrated in FIG. 4, the antiseptic material 940 can be sufficiently thick to fill a void between an exterior surface of the male luer 830 and an interior surface of the shroud or collar on the distal end of the male connector 800. The fluid-delivery or antiseptic material 940 can compress between these surfaces. As shown in FIGS. 3A-3C and 4, a space can be provided between an exterior surface of the fluid-delivery or antiseptic material 940 and an interior surface of the exterior wall or skirt 920 of the cap 900, such that the exterior surface of the fluid-delivery or antiseptic material 940 does not contact the interior surface of the exterior wall or skirt 920 of the cap 900. As shown in FIG. 4, in some embodiments, at least a portion of the space can be generally equal to, and/or smaller than, the thickness of the wall of the shroud or collar on the distal end of the connector 800, and at least a portion of the space can be smaller than the thickness of the wall of the shroud or collar on the distal end of the connector 800.

Delivery Systems

The present application includes a number of embodiments of delivery systems (e.g. syringes, dispensing surfaces, holders, containers, sleeves, etc.) for an antiseptic cap. Though one or more Figures may show a delivery system with a particular embodiment of a cap, it shall be understood that any other caps or other medical devices disclosed herein can be used in and/or with any of the delivery systems in addition to or instead of the illustrated cap. For example, any one of the embodiments of the caps described herein with reference to one or more of FIGS. 1A-4 of the present application can be provided or used in connection with any delivery system whether or not illustrated in such delivery system. It will be understood that any of the delivery systems described herein can be used or modified to be used with the various embodiments of a cap described and/or contemplated within the present application.

Antiseptic Cap Holder Assembly

Figure 5A:
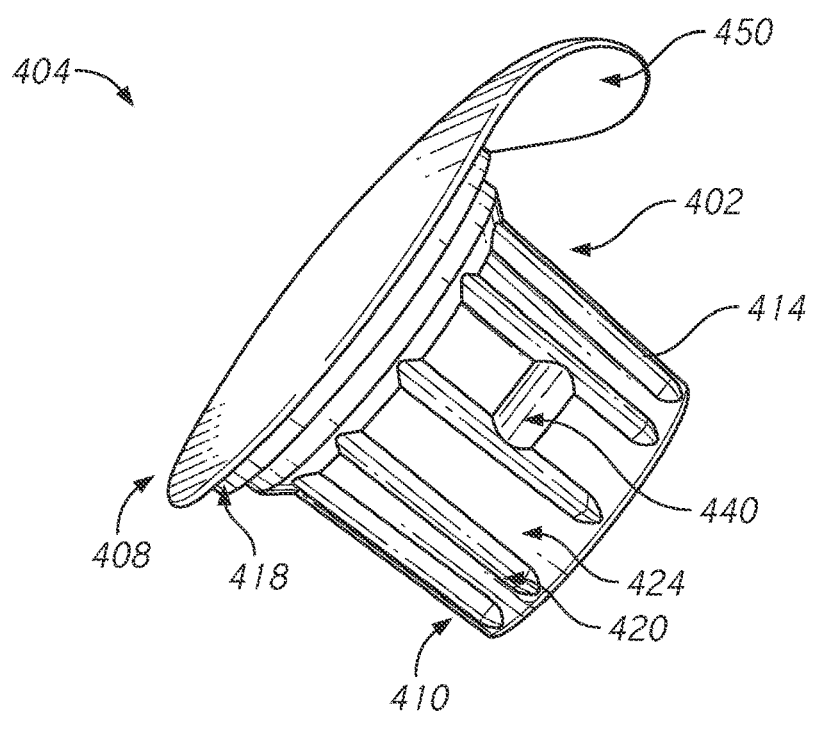
FIG. 5A is a front perspective view of an embodiment of an antiseptic cap holder assembly.
Figure 5B:
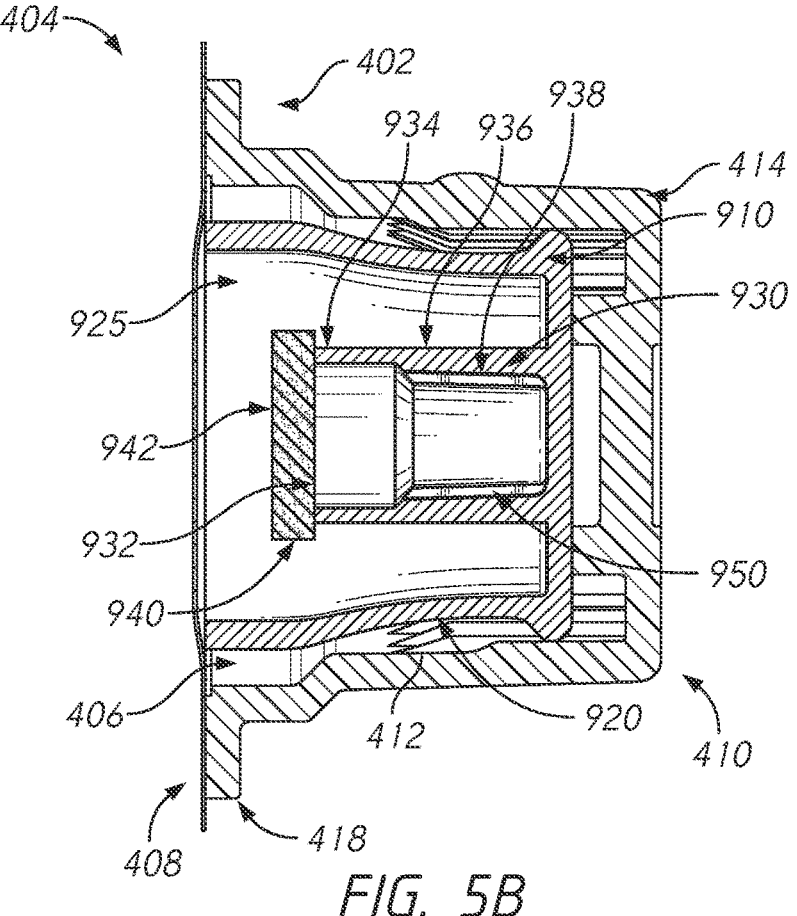
FIG. 5B is a side cross-sectional view of the antiseptic cap holder assembly of FIG. 5A.

FIGS. 5A and 5B are various views of an antiseptic cap holder assembly 404, according to some embodiments. In particular, FIG. 5A is a front perspective view of an antiseptic cap holder assembly 404, and FIG. 5B is a side cross-sectional view of the antiseptic cap holder assembly 404 of FIG. 5A. Unless otherwise noted, reference numerals in FIGS. 5A and 5B refer to components that are the same as or generally similar to the components in the remaining figures discussed herein. While the antiseptic cap 900 shown in FIGS. 5A and 5B are similar to antiseptic cap 900 shown in FIGS. 3A-4, it will be understood that the features described with reference to the antiseptic cap holder assembly 404 shown in FIGS. 5A and 5B can be used with any antiseptic cap and/or cap assembly embodiments described and/or contemplated herein. For example, any one of the antiseptic cap 900 of FIG. 1 and/or any additional caps disclosed herein can be modified to function with the antiseptic cap holder assembly 404, as shown and described with reference to FIGS. 5A and 5B.

FIGS. 5A and 5B show an antiseptic cap holder assembly 404 having an antiseptic cap holder 402 and an antiseptic cap 900 positioned within the cap holder 402. The cap holder 402 includes a proximal end 408, a distal end 410, an inner wall surface 412, and an outer wall surface 414 defining a chamber 406. The cap holder 402, in some embodiments, can include an opening 416 into the chamber 406 and a radially outwardly extending flange 418 circumjacent the opening 416. As shown in FIG. 5A, the flange 418 may extend from the proximal end 408 of the cap holder 402. The cap holder 402 may include an optional bottom wall 419.

The cap holder 402, in some embodiments, prevents contamination of an antiseptic cap 900 within the cap holder 402. For example, a user may handle the antiseptic cap holder assembly 404 via one or more portions of the cap holder 402, such as the flange 418 extending out from the cap holder 402. The cap holder 402 may act as a guard against contact of the antiseptic cap 900 by a user.

The cap holder 402 can comprise any suitable material (e.g., rigid or semi-rigid material). In some embodiments, the cap holder 402 can comprise any suitable polymer. In some embodiments, the polymer may include a thermoplastic polymer, such as an aliphatic polymer or thermoplastic elastomer. For example, the cap holder 402 may comprise at least one of polypropylene and polyethylene (such as low, medium, or high density polyethylene). A semi-rigid material of the cap holder 402 can have any suitable durometer. For example, in some embodiments, the cap holder 402 can have a Shore A durometer in the range of approximately 60 to approximately 1050, although any suitable durometer can be used, such as, for example, about 50, about 55, about 60, about 65, about 70, about 75, about 80, about 85, about 90, about 95, about 100, among others (e.g., any durometer between about 50 and about 100). However, it will be understood that the cap holder 402 can have any durometer sufficient to house an antiseptic cap 900.

As shown in FIGS. 5A and 5B, the antiseptic cap holder assembly 404 may be sealed with a foil material or lid 450, in some embodiments. The lid 450 may permit each antiseptic cap 900 within an antiseptic cap holder 402 to remain sterile. The lid 450 may be configured to attach to one or more portions of the antiseptic cap holder 402 and/or directly to the antiseptic cap 900. In some embodiments, the lid 450 can be sealed to the antiseptic cap holder 402. For example, the lid 450 may be attached to the flange 418 by any suitable method such as by one or more adhesives or by one or more conductive or inductive heat sealing techniques.

Additionally or alternatively, the lid 450 may be sealed to at least a portion of the antiseptic cap 900. Attachment directly to the antiseptic cap 900 permits the lid 450 to seal the first chamber 925 and prevent the removal of any antiseptic material 940 and/or antiseptic fluid within the antiseptic cap 900. In some embodiments, the lid 450 may form a double seal when the lid 450 is sealed against both the antiseptic cap holder 402 and the antiseptic cap 900 within the antiseptic cap holder 402. For example, a double seal may provide an extra barrier to prevent contamination of an antiseptic cap 900 and/or prevent an antiseptic material from escaping from the antiseptic cap 900. Providing a double seal may advantageously improve shelf life.

In some instances, the lid 450 may be sealed to the antiseptic cap 900 without the inclusion of an antiseptic cap holder 402. For example, an antiseptic cap assembly 2004, as shown in FIGS. 6-10 and described in further detail herein, may be formed when a lid 450 is attached directly to an antiseptic cap 900 without the use of an antiseptic cap holder 402. Attachment directly to the antiseptic cap 900 without the presence of the holder 402 may maintain the sterility of the antiseptic cap 900 prior to use while minimizing the materials, size, waste, and manufacturing and shipping costs associate with providing antiseptic cap assemblies. As described herein, attachment of the lid 450 to the antiseptic cap 900 seals the first chamber 925 and prevents or resists the removal of any antiseptic material 940 and/or antiseptic fluid within the antiseptic cap 900.

In some embodiments, the lid 450 may be thermally bonded to one or more of the antiseptic cap holder 402 and the antiseptic cap 900. Thermal bonding may occur using standard heat sealing technology, such as impulse, induction, conduction, radiant, or other heat sealing techniques. In some embodiments, the lid 450 could be attached to the antiseptic cap holder 402 and/or the antiseptic cap 900 by utilizing an adhesive bond or by a suitable mechanical or friction connection, such as a snap-fit.

The lid 450 could be made of any suitable material, such as foil, plastic, a laminate, etc. In one aspect, the lid 450 could be made of a foil material having a thickness of approximately 1 to 2 mil.

The antiseptic cap holder 402 and/or the antiseptic cap 900, in some instances, can comprise a structure, element or the like that prevents the relative rotation of the antiseptic cap holder 402 and the antiseptic cap 900. In some embodiments, the structure or element may facilitate attaching the antiseptic cap to a medical connector by engaging the antiseptic cap 900 and locking the antiseptic cap 900 in place to prevent rotation of the antiseptic cap 900 when positioned inside the antiseptic cap holder 402. For example, in some embodiments, the inner wall surface 412 of the antiseptic cap holder 402 may comprise internal ribs and/or internal slots. The internal ribs and/or internal slots may be configured to interact with an outer surface of the skirt 920 of the antiseptic cap 900. In some embodiments, the antiseptic cap 900 may comprise a plurality of ribs and/or a plurality of slots that are configured to interact the internal ribs and/or internal slots of the antiseptic cap holder 402. These structures may prevent or resist the relative rotation of the antiseptic cap holder 402 with respect to the antiseptic cap 900. The term "ribs" referred to herein are structures that are raised or extend outward from a surface. The term "slots" refer to structures that extend below a surface or are positioned between two ribs and are at a lower level than the ribs.

In some embodiments, the antiseptic cap holder 402 may have a feature or structure that forms an interference fit with the external surface of the antiseptic cap 900. In some embodiments, an inner surface 412 of the antiseptic cap holder 402 may have a feature or structure to form an interference fit with a portion of the antiseptic cap 900. Additionally or alternatively, the antiseptic cap 900 may have one or more features to form an interference fit with the antiseptic cap holder 402.

As shown in FIGS. 5A and 5B, an antiseptic cap holder assembly 404 may incorporate circumferentially spaced ribs 420 for grasping by the hand of a user of the antiseptic cap holder assembly 404. The antiseptic cap holder assembly 404 can be used for the same purposes as described herein and may be used by hand.

The antiseptic caps and/or antiseptic cap holder assemblies disclosed herein may be distributed and/or packaged in various suitable methods. Suitable methods include, but are not limited to, individual packages, a pouch package containing a plurality of antiseptic caps and/or antiseptic cap holder assemblies (such as a dispensing bag discussed herein with reference to FIGS. 6-10), a dispensing device (discussed herein with reference to FIGS. 11A-11D), or a syringe assembly wherein the antiseptic caps and/or antiseptic cap holder assemblies may be attached to a syringe (discussed herein with reference to FIGS. 12A and 12B). It will be appreciated that the distribution and/or packaging method, as well as the relative sizes, of the antiseptic caps and/or antiseptic cap holder assembly disclosed herein are exemplary and non-limiting. Indeed, it will be understood, that the packaging can be modified for any suitable embodiment, and that relative methods can differ in various embodiments.

Dispensing Bag

FIGS. 6-10 are various views of a delivery system for medical articles in the form of examples of a dispensing bag 2000 for antiseptic cap assemblies 2004 and/or antiseptic cap holder assemblies, according to various embodiments.

Figure 6:
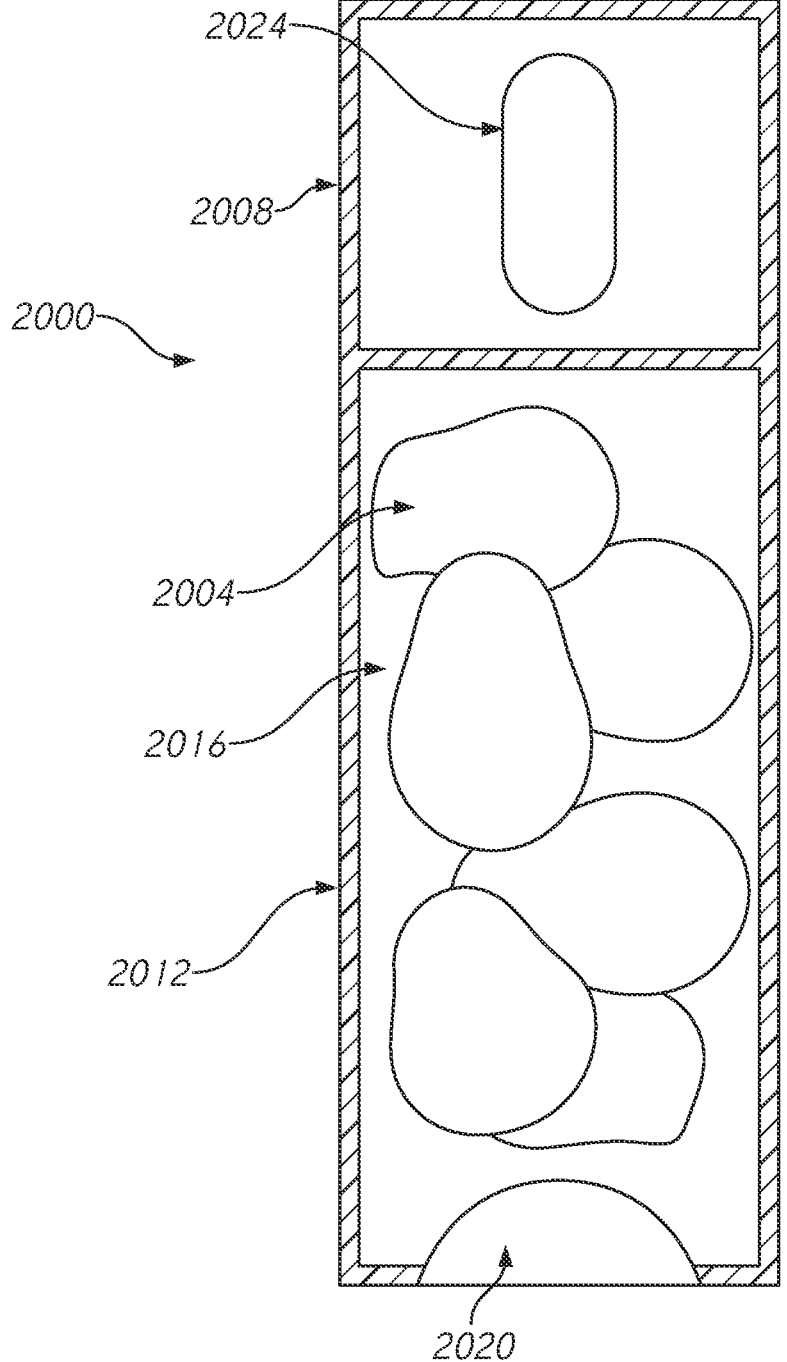
FIG. 6 is a front view of an embodiment of a dispensing bag for antiseptic cap holder assemblies.
Figure 7:
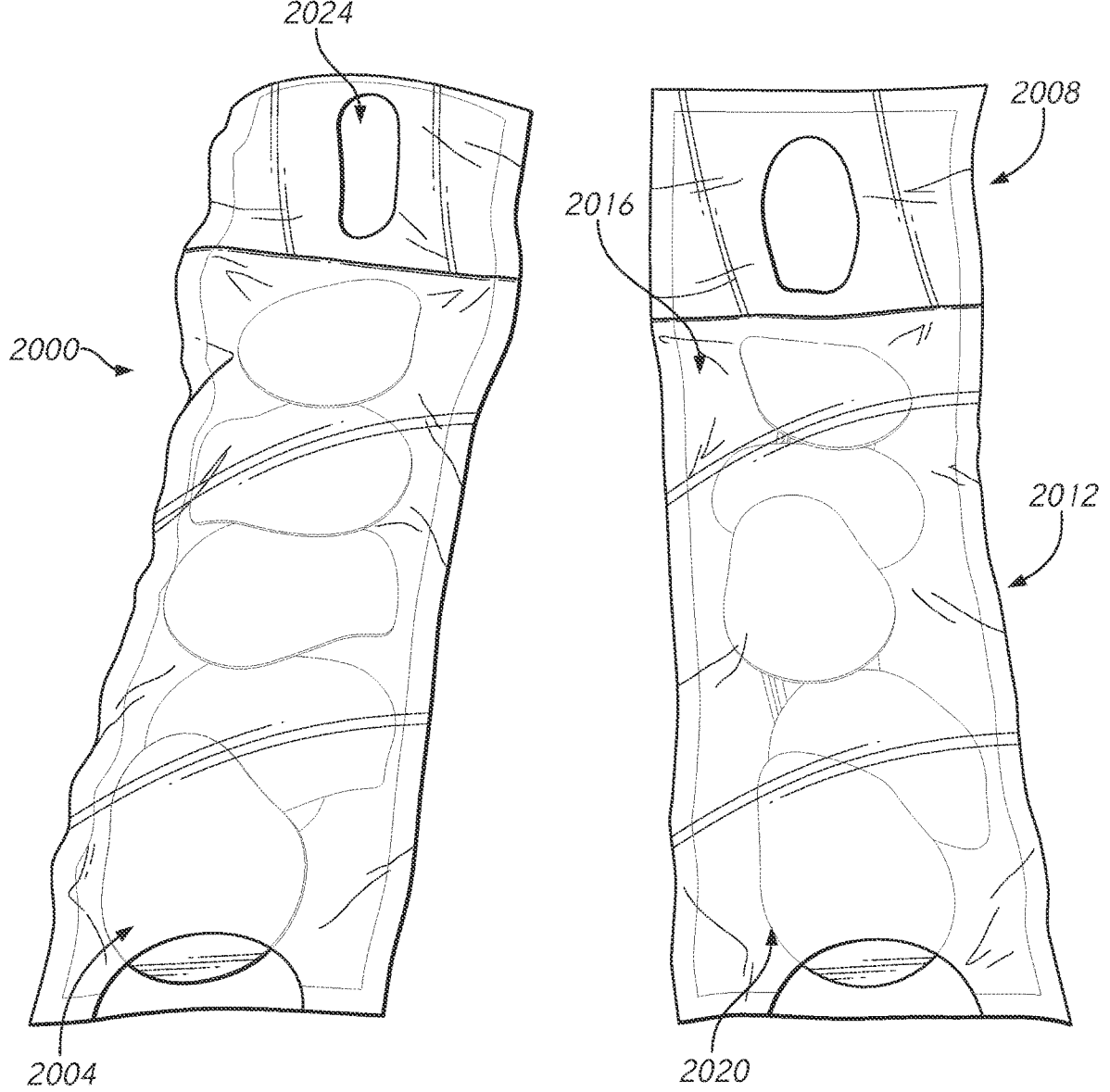
FIG. 7 is a front perspective view of multiple dispensing bags of FIG. 6.
Figure 8A:
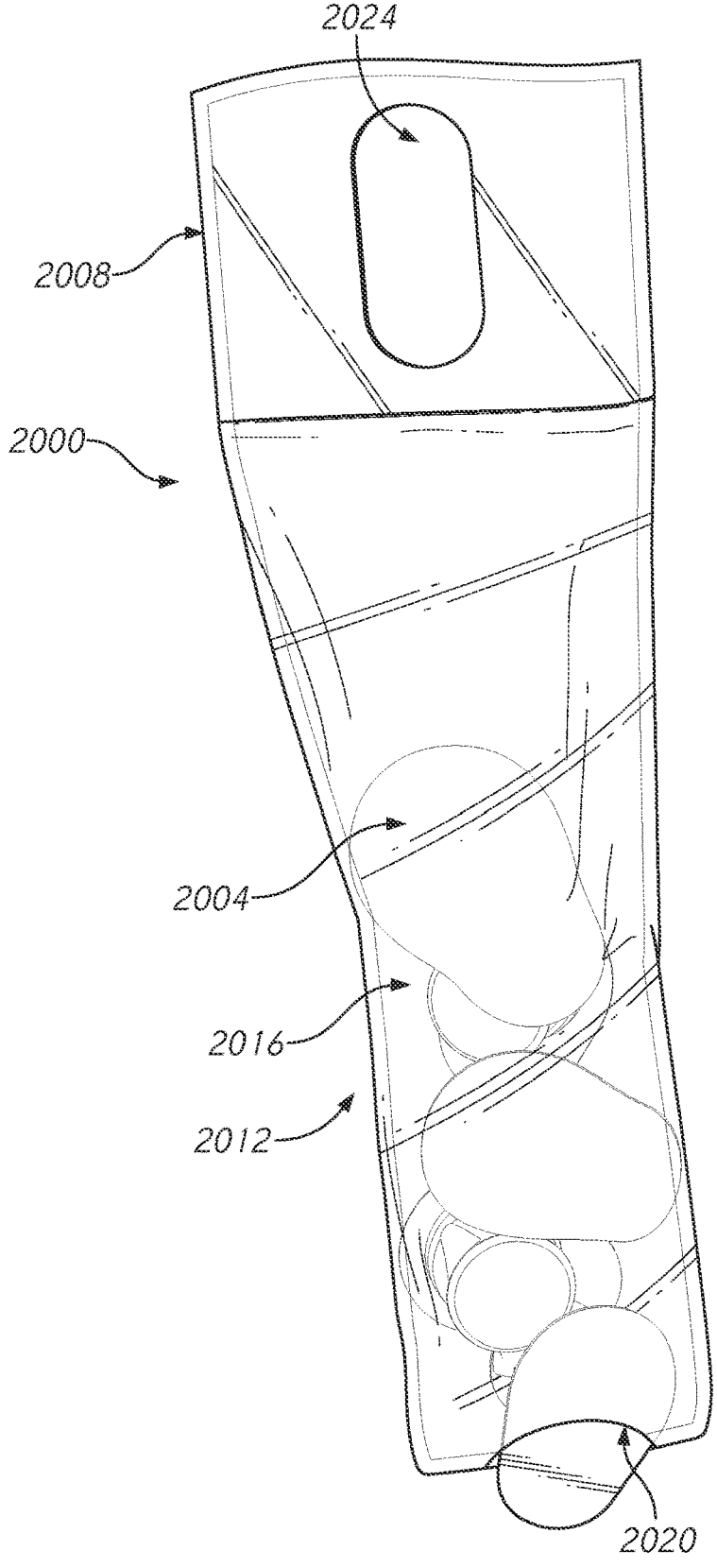
FIG. 8A is a front view of the dispensing bag of FIG. 6.
Figure 8B:
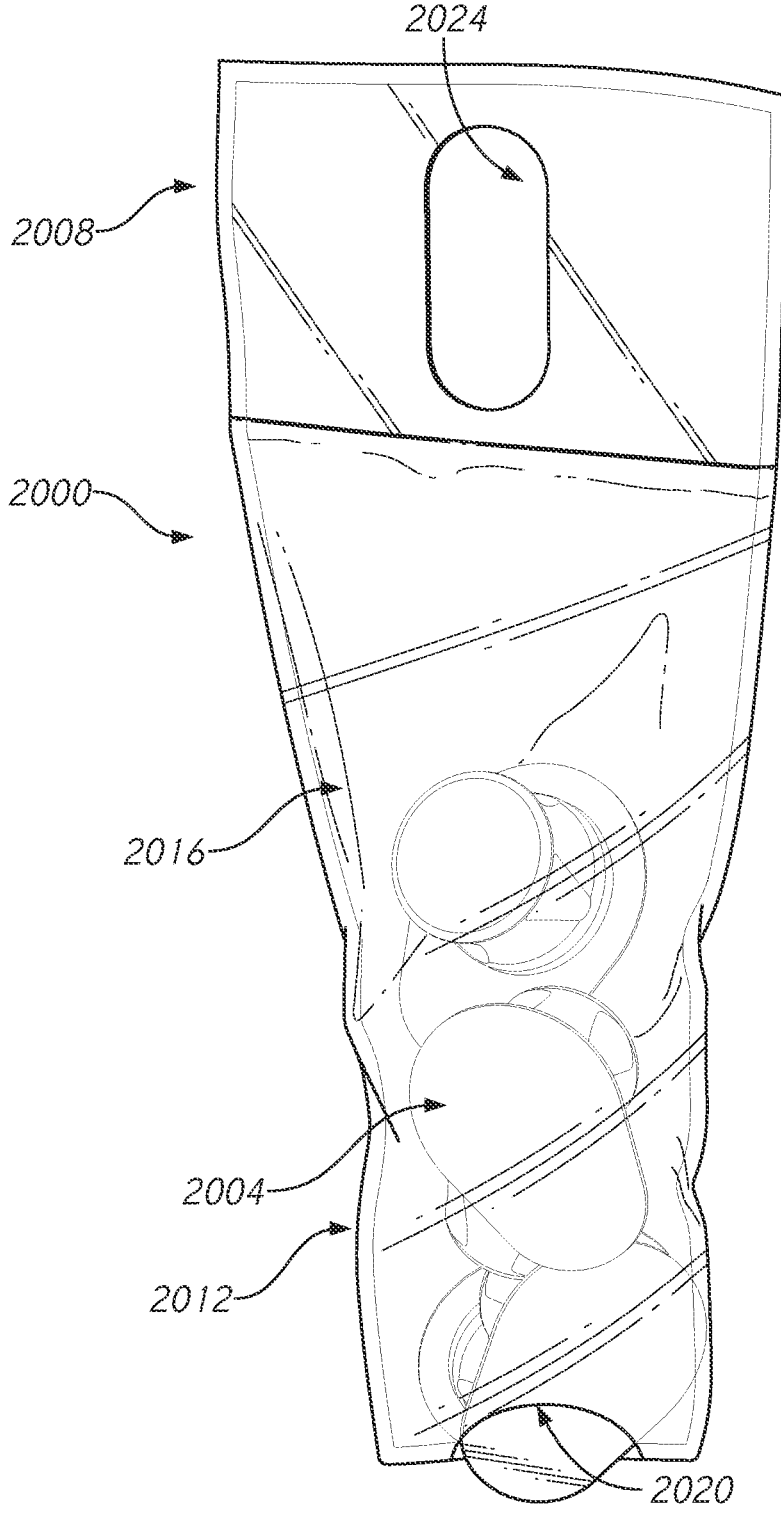
FIG. 8B is a rear view of the dispensing bag of FIG. 6.
Figure 10:
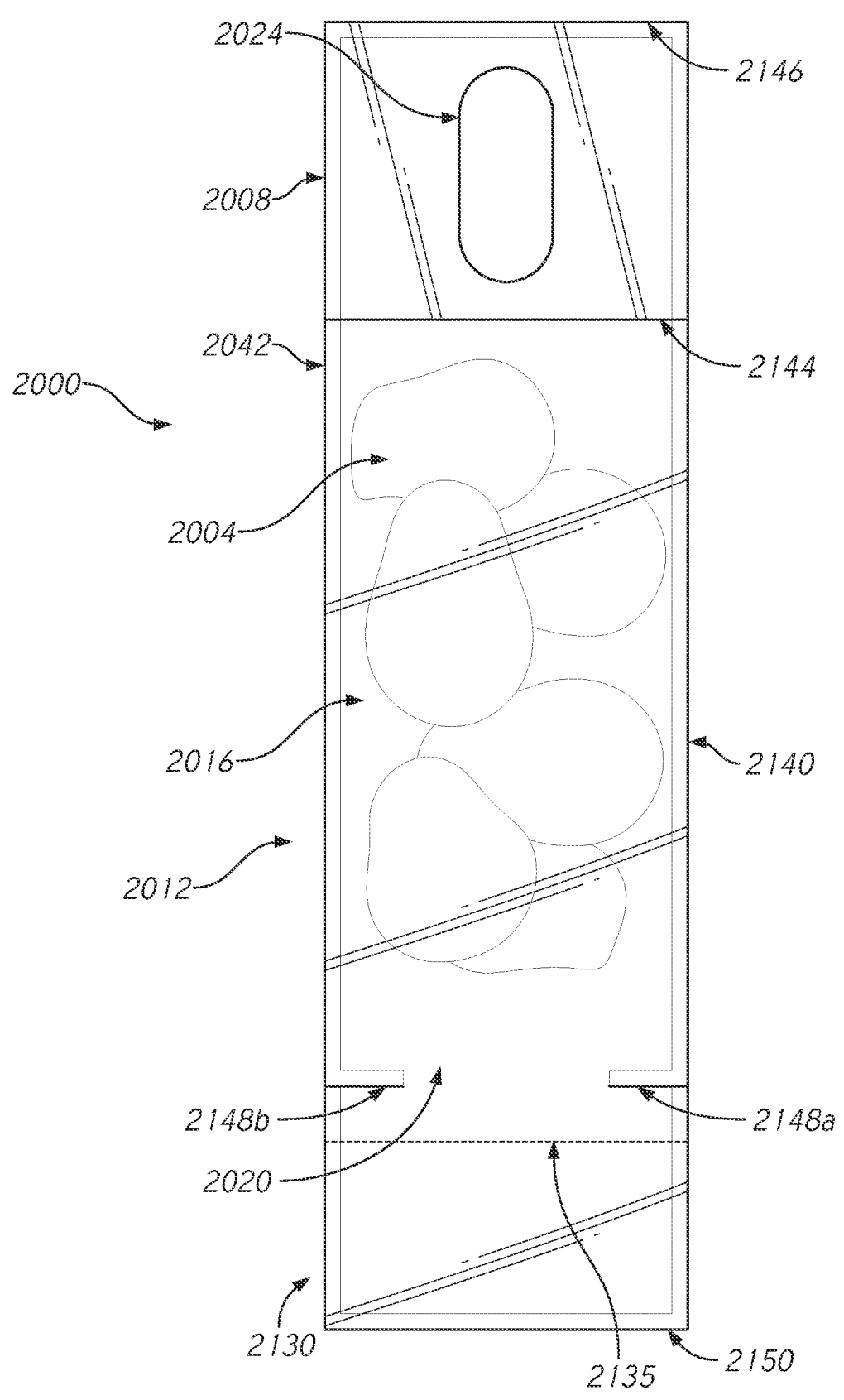
FIG. 10 is a front view of an embodiment of a dispensing bag for antiseptic cap holder assemblies.

In particular, FIG. 6 is a front view of a dispensing bag 2000 including one or more an antiseptic cap assemblies 2004, and FIGS. 7, 8A, and 8B are front perspective, front, and rear views of multiple dispensing bags 2000 of FIG. 6, respectively. FIGS. 9A-9C are front views of various embodiments of dispensing bags 2000a-2000c for antiseptic caps and/or antiseptic cap assemblies 2004. FIG. 10 is a front view of a dispensing bag 2100 for antiseptic caps and/or antiseptic cap assemblies 2004. Unless otherwise noted, reference numerals in FIGS. 6-10 refer to components that are the same as or generally similar to the components in the remaining figures discussed herein. While the antiseptic cap assembly 2004 shown in FIGS. 6-10 are similar to antiseptic cap holder assembly 404 shown in FIGS. 5A and 5B without the addition of the antiseptic cap holder 450, it will be understood that the features described with reference to the dispensing bag shown in FIGS. 6-10 can be used with any antiseptic cap and/or cap assembly embodiments described and/or contemplated herein. For example, any one of the antiseptic cap 900 of FIGS. 1A-2, antiseptic cap 900 of FIGS. 3A-4, antiseptic cap holder assembly 404 of FIGS. 5A-5B, and/or any additional caps disclosed herein can be modified to function with the dispensing bag, as shown and described with reference to FIGS. 6-10.

In any embodiments, as shown, a delivery system can comprise a generally elongate portion comprising a tube or sheath region with an interior cavity having an interior width or diameter that corresponds to the outer width or diameter of each of a plurality of medical articles to be contained within and dispensed from the delivery system. For example, the interior width or diameter of the elongate portion of the delivery system can be about the same as or slightly larger than the outer width or diameter of each of the plurality of medical articles to permit the plurality of medical articles to be contained loosely within the elongate portion, thereby enabling the plurality of medical articles to shift and/or move within the tube or sheath without being affixed or engaged with each other or with the tube or sheath. For example, in some embodiments, the interior of the elongate portion is shaped and composed such that the plurality of medical articles can automatically form a single vertical column of medical articles in the elongate portion as individual units of the medical articles are inserted or loaded into a proximal opening of the delivery system. The loose containment can permit a column of medical articles positioned within the tube or sheath to move toward a dispensing region of the delivery system (e.g., a constriction or a reduced-width region) as medical articles are removed through a distal dispensing region in multiples or singly (one at a time).

The interior width or diameter of the elongate portion of the delivery system can be sufficiently small so that it does not permit more than one full medical article to occupy the same level (e.g., a vertical level) within the elongate portion of the delivery system at the same time, thereby resisting clogging or other obstruction of the elongate portion by interference among the contained medical articles. The interior wall or walls of the elongate portion can have a coefficient of friction that is sufficiently low (or slippery) to permit reliable and consistent migration of the loose medical articles through the delivery system during use (such as when being pushed or pulled by a user through the delivery system), and/or that is sufficiently high (or slide resistant) to create an inertial position for each medical article during containment within the elongate portion to resist free-sliding and bunching up of the medical articles contained in the delivery system. The wall or walls of the elongate portion can be flexible and/or collapsible such that an irregular, non-smooth surface topography is produced along the interior wall or walls (e.g., comprising wrinkles or creases) in normal use when the elongate portion contains medical articles, in order to produce a low-level of resistance to rapid sliding of the medical articles through the tube or sheath when not being pushed or pulled out of the delivery system by a user.

The dispensing bag 2000, as shown in FIGS. 6-8B, may function as a delivery system to contain one or more disinfectant devices, or at least a portion of one or more disinfectant devices, such as, for example, antiseptic cap 900, antiseptic cap assembly 2004, or antiseptic cap holder assembly 404. Any reference in this specification to the use or containment of an antiseptic cap 900 and/or an antiseptic cap assembly 2004 of any type should also be interpreted to include the use, in addition or in the alternative, of an antiseptic cap and/or an antiseptic cap holder. In some embodiments, the dispensing bag 2000 facilitates access to an antiseptic cap assembly 2004 by advantageously allowing for removal of a single antiseptic cap assembly 2004 at a time, while maintaining one or more other antiseptic cap assemblies 2004 within the dispensing bag 2000.

Each of the cap assemblies 2004 may include any antiseptic cap described herein. While the figures illustrate the dispensing bag 2000 housing five antiseptic cap assemblies 2004, it will be understood that any number of disinfectant filled devices can be packaged within a dispensing bag 2000. It will also be understood that any of the embodiments of the dispensing bag 2000 described and/or contemplated herein can be modified to be used with any antiseptic cap described and/or contemplated herein.

In some embodiments, as shown in FIGS. 6-8B, the dispensing bag 2000 has a proximal portion 2008 and a distal portion 2012. The distal portion 2012 may comprise a chamber 2016 sized and configured to contain one or more antiseptic cap assemblies 2004. For example, in some embodiments, the distal portion 2012 comprises one more sealed edges extending along the perimeter of the distal portion 2012 to form an interior surface of the chamber 2016. In some embodiments, the interior surface can have any suitable surface texture, such as, for example, smooth and/or rough.

The chamber 2016 can comprise any suitable shape and/or configuration capable of receiving at least a portion an antiseptic cap assembly 2004. For example, as shown in FIGS. 6-8B, the chamber 2016 can comprise a generally cylindrical shape, although it will be appreciated that the chambers 2016 can comprise any suitable wall structure (e.g., straight and/or curved) and have any suitable shape (e.g., cylindrical, tapered, conical).

A width of the chamber 2016, as shown in FIG. 6-8B, may be larger than a width of the outer surface of the antiseptic cap assembly 2004 to facilitate containing the antiseptic cap assembly 2004. In some embodiments, the width of the chamber 2016 may remain constant throughout the chamber 2016. In some embodiments, the width of the chamber 2016 may vary along the length of the chamber. For example, the chamber 2016 can comprise a portion having a narrowed width as the chamber 2016. In some embodiments, the narrowed width may be located adjacent to a distal end of the dispensing bag 2000 to facilitate the removal of a single antiseptic cap assembly 2004 at a time.

A length of the chamber 2016 may be sufficiently long to house a plurality of antiseptic cap assemblies 2004 and/or antiseptic cap holder assemblies 404 and prevent accidental or incidental removal of the antiseptic cap assemblies 2004 and/or antiseptic cap holder assemblies 404 from the chamber 2016.

In some embodiments, the interior surface of the dispensing bag 2000 may be attached to one or more of the antiseptic cap assemblies 2004 contained within the chamber 2016. The attachment may utilize an adhesive bond or by a suitable mechanical or friction connection, such as a snap-fit.

In some embodiments, as illustrated in FIGS. 6-8B, the dispensing bag 2000 may comprise one or more openings 2020. The opening 2020 may allow a user to remove one or more antiseptic cap assemblies 2004 from the chamber 2016. For example, the opening 2020 provides access to the antiseptic cap assembly 2004, while still allowing the dispensing bag 2000 to retain any remaining antiseptic cap assemblies 2004 within the chamber 2016.

As shown in FIGS. 8A and 8B, in some embodiments, the opening 2020 may be located at a distal end of the dispensing bag 2000. The opening 2020 may form a constriction such as by extending across only a portion of the distal end. For example, as shown in FIGS. 6-8B, the opening 2020 may not extend along the entire length of the distal end of the dispensing bag 2000 (for example, as shown in FIG. 9B discussed herein). In some embodiments, the width of the opening 2020 can be smaller than the outer width or diameter of the medical article, such as the antiseptic cap assembly 2004 or cap, that is contained within the delivery system to resist freely dropping out medical articles through the opening 2020 when not being pushed or pulled by a user. In some embodiments, the width of the opening 2020 can be smaller than the outer width or diameter of the medical article, but sufficient largely that it can temporarily resiliently or flexibly increase in size to permit the medical article to pass through the opening 2020 without tearing or irreversibly stretching or otherwise damaging the material of which the opening 2020 is made. Placement of the opening 2020 at the distal end advantageously allows for the antiseptic cap assembly 2004 to naturally be placed adjacent to, or partially extending through, the opening 2020 when the dispensing bag 2000 is hung (as described in further detail below). In this manner, the location of the opening 2020 may facilitate access to the antiseptic cap assembly 2004. However, it will be understood, that the location can be modified for any suitable embodiment.

The opening 2020 can comprise any suitable shape and/or configuration capable of permitting access to, while resisting accidental removal of, an antiseptic cap assembly 2004 from within the chamber 2016. For example, FIGS. 9A-9C show partial front views of various embodiments of dispensing bags 2000a-2000c for antiseptic caps and/or antiseptic cap assemblies 2004.

As shown in FIG. 9A, in some embodiments, an opening can comprise one or more slits 2020a. The dispensing bag 2000c may comprise a completely sealed distal edge 2030a and the slit 2020a may formed along a sidewall and extend into the chamber 2016 of the dispensing bag 2000a. A user may utilize the slit 2020a to gain access to one or more antiseptic cap assemblies 2004 within the chamber 2016. In some embodiments, the slit 2020a may be predisposed in a closed position to prevent the unintended removal of the antiseptic cap assembly 2004 from the dispensing bag 2000a.

FIG. 9B shows that, in some embodiments, an opening 2020b can comprise a diameter smaller than a diameter of the outer surface of the antiseptic cap assembly 2004 to prevent the unintended removal of the antiseptic cap assembly 2004 from the delivery system or to permit only a portion of the antiseptic cap assembly 2004 to extend outside of the chamber 2016 while the rest of the antiseptic cap assembly 2004 remains contained inside of the delivery system until it is intentionally removed. For example, the opening 2020*b* may include one or more sealed edges 2040 within the chamber 2016 and/or one or more sealed edges 2030*b* at a distal end of the dispensing bag 2000. The one or more sealed edges 2040, 2030*b* may taper towards the opening 2020*b*. The one or more sealed edges 2040, 2030*b* may advantageously permit only one antiseptic cap assembly 2004 to extend through the opening 2020*b*. The one or more sealed edges 2040, 2030*b* can comprise any suitable shape and/or configuration capable of receiving at least a portion an antiseptic cap assembly 2004. For example, as shown in FIG. 9B, the sealed edge 2040 can comprise a generally conical shape, although it will be appreciated that the sealed edge 2040 can comprise any suitable wall structure (e.g., straight and/or curved) and have any suitable shape (e.g., cylindrical, tapered).

As shown in FIG. 9C, in some embodiments, an opening 2020*c* may be located on along a side edge of the dispensing bag 2000. For example, a dispensing bag 2000*c* may comprise a completely sealed distal edge 2030*c*. The sealed distal edge 2030*c* may advantageously prevent the unintended removal of the antiseptic cap assembly 2004 from the delivery system caused by a downward gravitational force alone (e.g. when the dispensing bag is in a vertically hanging position).

In embodiments in which a portion of the antiseptic cap assembly 2004 protrudes beyond the opening 2020, a user may remove the antiseptic cap assembly 2004 from the dispensing bag 2000. In some embodiments, the opening 2020 may have a diameter the same size as or greater than the antiseptic cap assembly 2004. It will be appreciated that location of the opening 2020, as well as the relative size, indicated in FIGS. 6-10 is exemplary and non-limiting. Indeed, it will be understood, that the relative size can be modified for any suitable embodiment, and that the relative proportions of the opening 2020 in relation to the remainder of the dispensing bag 2000 can differ in various embodiments. In some embodiments, the dispensing bag 2000 may not incorporate one or more openings 2020.

To remove the antiseptic cap assembly 2004 from the dispensing bag 2000, a user may grasp a portion of the antiseptic cap assembly 2004 that is positioned within the bag 200, or that is protruding beyond the opening 2020, and apply a removal force, such as a downward force (if the dispensing bag 2000 is positioned in a vertically hanging orientation). In some embodiments, a user may push the antiseptic cap assembly 2004 out through the opening 2020 by grasping at least a portion of the dispensing bag 2000 and applying a pinching force or other force to the antiseptic cap assembly 2004 through the dispensing bag 200 to advance the antiseptic cap assembly 2004 through the opening 2020. In some embodiments, the dispensing bag 2000 may advantageously eliminate the need for direct contact with the antiseptic cap assembly 2004 during removal from the dispensing bag 2000. In some embodiments, the dispensing bag 2000 facilitates removal of the antiseptic cap assembly 2004 through an efficient process that only requires the use of a single hand.

The antiseptic cap assembly 2004 may be withdrawn from the dispensing bag 2000 such that the removal (e.g., downward) force required to withdraw the antiseptic cap assembly 2004 from the chamber 2016 is greater than the force of gravity on the leading (distalmost) antiseptic cap assembly

2004 located within or partially within the dispensing bag, such that the antiseptic cap assembly 2004 does not drop through the hole 2024 merely under the force of gravity.

To prevent accidental removal of the antiseptic cap assembly 2004 from the dispensing bag 2000, in some embodiments, the dispensing bag 2000 can comprise a semi-rigid or resilient or elastomeric material capable of deformation when a force is applied. As the antiseptic cap assembly 2004 is being removed from the chamber 2016, the opening 2020 can be configured to deform radially outward or in an opening direction that is generally perpendicular to the longitudinal axis of the dispensing bag 200 in one or more locations where the antiseptic cap assembly 2004 contacts or otherwise interacts with the opening 2020. In some embodiments, the opening 2020 can be configured to rebound radially inward in a closing direction, generally opposite from the opening direction, after the antiseptic cap assembly 2004 is removed from the dispensing bag 2000 through the opening 2020. This may advantageously allow the opening 2020 of the dispensing bag 2000 to temporarily and/or permanently deform when the opening 2020 interacts with one or more features of the antiseptic cap assembly 2004. In some embodiments, the ability of the opening 2020 to deform can permit the antiseptic cap assembly 2004 to be removably contained within the chamber 2016. In some embodiments, the distal opening 2020 is smaller than a proximal opening in the dispensing bag, which can permit the rapid loading of multiple antiseptic cap assemblies 2004 through the proximal opening in quick succession during manufacturing, while resisting the unintentionally unloading of the contained antiseptic cap assemblies 2004 out of the distal opening 2020.

The dispensing bag 2000, in some embodiments, may comprise one or more features configured to allow the user to create an opening 2020 and gain access to one or more antiseptic cap assemblies 2004 within the chamber 2016. FIG. 10 shows an embodiment of the dispensing bag 2000 having a sealing portion 2130 located distal to an opening 2020. In some embodiments, the sealing portion 2130 may include a sealed distal edge 2150 and at least a portion of a sealed side edge 2140. The sealed side edge 2140 may include at least a portion of the chamber 2016. The sealing portion 2130 may be removably detached from the dispensing bag 2000. In some embodiments, the dispensing bag 2000 may comprise contain notches and/or perforations and/or scores 2135 to allow a user to tear or open or otherwise remove the sealing portion 2130 of the dispensing bag 2000 and form or access the opening 2020. Upon removal of the sealing portion 2130, the dispensing bag 2000 may include one or more sealed distal edges 2148*a*, 2148*b* defining the opening 2020. The opening 2020 may include any features described herein.

In some embodiments, the dispensing bag 2000 may be manufactured utilizing one or more steps described herein. A plurality of sheets of material, such as two sheets, may be placed in alignment to provide the faces of the dispensing bag 2000. For example, a first sheet may be placed on top of a second sheet with both sheets being generally the same size and shape. In some embodiments, the sheets may be rectangular; however, the sheets may comprise any shape suitable to form the dispensing bag 2000. One or more edges or other regions of the sheets may be bonded or sealed to provide the chamber 2016 of the dispensing bag 2000. Any suitable method may be used to bond or seal the one or more edges or other regions. For example, in some embodiments, heat staking and/or thermal bonding may be used to melt and seal at least a portion of the sheets to each other and/or around a portion (e.g., an edge) of a perimeter of the chamber 2016. Thermal bonding may be performed using standard heat sealing technology, such as impulse, induction, conduction, radiant, or other heat sealing techniques. Additionally or alternatively, the edges may be sealed by utilizing sonic welding, an adhesive bond, or by any suitable mechanical or friction connection, such as a snap-fit. In some embodiments, an attachment agent, such as glue or solvent or adhesive, or any other suitable agent may be used. With reference to FIG. 10, for example, the side edges 2140, 2142 may be sealed along with one or more edges 2144, 2146 located in the proximal portion 2008. In some embodiments, the resulting assembly has an opening 2020 in the distal portion 2012 with a hollow chamber 2016 for retaining antiseptic cap assemblies 2004. The one or more antiseptic cap assemblies 2004 may be placed within the chamber 2016 through any suitable methods. The opening 2020 may be formed by forming edges 2148*a*, 2148*b* through any sealing method described herein. In some embodiments where the dispensing bag 2000 comprises the sealing portion 2130, the distal end 2150 can be sealed and the notches, perforations, and or scores 2135 may be formed along the width of the dispensing bag 2000.

The proximal portion 2008 of the dispensing bag 2000 can include one or more hanging holes 2024, in some embodiments. For example, the hole 2024 may include a die cut hole or holes. The hole 2024 can be sized and configured to allow the dispensing bag 2000 to be hung on a convenient hanger. For example, a user may utilize the one or more holes 2024 to hang the dispensing bag 2000 on an IV pole. The hole 2024 can comprise any suitable shape and/or configuration capable of allowing the dispensing bag 2000 to be hung on a hanger. The location of the hole 2024, as well as the relative size, indicated in FIGS. 6-8B are exemplary and non-limiting. Indeed, the location and relative size can be modified for any suitable embodiment, and the relative proportions of the hole 2024 in relation to the remainder of the dispensing bag 2000 can differ in various embodiments. In some embodiments, the dispensing bag 2000 may not incorporate one or more holes 2024.

The dispensing bag 2000 may be made of non-permeable or very low permeable material. In some embodiments, the material may be generally chemically inert and/or non-conductive. The dispensing bag 2000 can provide an extra barrier to keep the caps and the antiseptic cap assembly 2004 from being contaminated, which provides improved shelf life. The dispensing bag 2000 may provide protection against contamination of the antiseptic cap assemblies 2004 when being handled. The dispensing bag 2000 can be configured to function as a physical barrier that isolates at least a portion of the antiseptic cap assembly 2004 from the outside environment. For example, in some embodiments, the dispensing bag 2000 can be configured to inhibit contaminants from entering the chamber 2016.

In some embodiments, all or a portion of the dispensing bag 2000 may be made of a transparent material, thereby allowing a user to readily identify the bag as a holder of a particular type of medical devices (such as antiseptic caps), and/or to read information printed on the packaging of one or more types of medical devices within the bag, and/or to determine the quantity of antiseptic cap assemblies 2004 remaining within the dispensing bag 2000 (such as to determine when it will be necessary to replace the bag), from the outside of the bag and/or from any viewing angle. In some embodiments, the dispensing bag 2000 avoids some complications associated with hanging the dispensing bag

2000 backwards, as the dispensing bag may be viewed and/or accessed from the front and back side, as shown in FIGS. 38A and 38B.

As shown in FIG. 10, in an example of a method for producing a dispensing bag 2000, one or more (or any combination) of the following steps may be performed: (a) providing front and rear flexible transparent sheets; (b) generally positioning the front sheet over the rear sheet; (c) generally aligning the perimeters of the front and rear sheets; (d) sealing or bonding multiple edges of the sheets to each other, such as each of the respective lateral sides and top edges of the sheets, to form a container for the dispensing bag 2000; (e) temporarily leaving at least one of the respective edges (e.g., the bottom edges) or portions of such edges of the sheets unsealed or unbonded to each other to form a temporary opening in the container; (f) inserting multiple caps (e.g., individually or in cap holders 410) into the container of the dispensing bag 2000 through the temporary opening; (g) after inserting the caps into the container, sealing or bonding the previously unsealed or unbonded end through which the caps were inserted; (h) sealing or bonding a portion of the respective sheets to form a constriction at an end or in a dispensing region of the dispensing bag 2000; (i) creating a perforation or other mark or region to facilitate removing a portion of the dispensing bag 2000 to enable removal of the caps previously inserted into the dispensing bag 2000. Any of these steps can be omitted or modified and the ordering of any of the steps can be changed. Various features of the dispensing bag 2000 can comprise the various illustrated dimensions and proportions, which form part of this disclosure. It will be appreciated that these dimensions are exemplary and non-limiting. Indeed, it will be understood that the dimensions can be modified for any suitable embodiment, and that their relative proportions can differ in various embodiments.

Dispensing Device

Figure 11D:
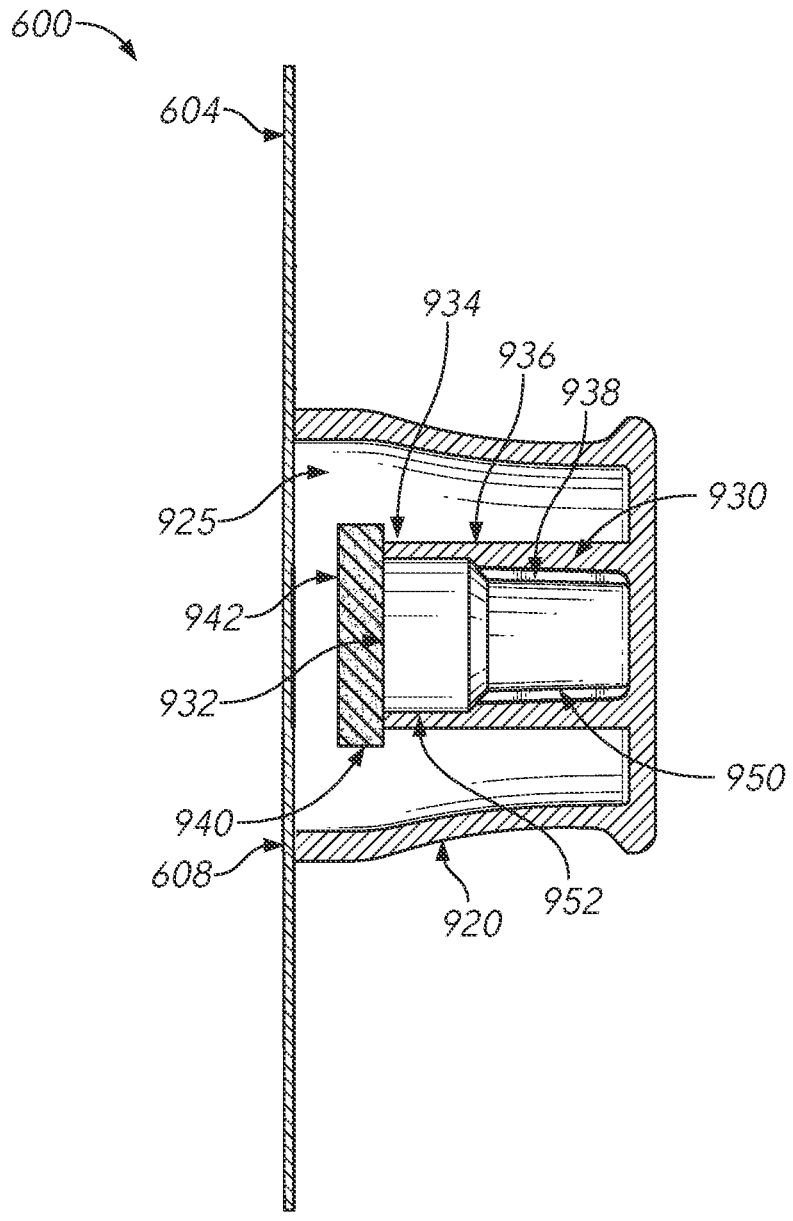
FIG. 11D is an exploded side cross-sectional view of the dispensing device of FIG. 11A.

FIGS. 11A-11D are various views of a delivery system for medical articles in the form of examples of a dispensing device 600 for antiseptic caps 900 and/or antiseptic cap holder assemblies 404, according to some embodiments. In particular, FIG. 11A is a top view of a dispensing device 600 including one or more an antiseptic caps 900, and FIGS. 11B, 11C, and 11D are side, side cross-sectional, and exploded partial side cross-sectional views of the dispensing device 600 of FIG. 11A, respectively. Unless otherwise noted, reference numerals in FIGS. 11A-11D refer to components that are the same as or generally similar to the components in the remaining figures discussed herein. While the antiseptic caps 900 shown in FIGS. 11A-11D are similar to the antiseptic cap 900 shown in FIGS. 3A-4, the features described with reference to the dispensing device shown in FIGS. 11A-11D can be used with any antiseptic cap and/or cap holder assembly embodiments described and/or contemplated herein. For example, any one of the antiseptic cap 900 of FIG. 2, antiseptic cap holder assembly 404 of FIGS. 5A-5B, and/or any additional caps disclosed herein can be modified to function with the dispensing device, as shown and described with reference to FIGS. 11A-11D.

FIGS. 11A-11D show a dispensing device 600. The dispensing device 600 may function as a delivery system to contain one or more disinfectant devices, or at least a portion of one or more disinfectant devices, such as, for example, as shown in FIGS. 11A-11D, an antiseptic cap 900 and/or an antiseptic cap holder assembly 404. Any reference in this specification to the use or containment of an antiseptic cap 900 of any type should also be interpreted to include the use, in addition or in the alternative, of an antiseptic cap holder assembly 404. In some embodiments, the dispensing device 600 facilitates access to an antiseptic cap 900 and/or an antiseptic cap holder assembly 404 by advantageously allowing for removal of a single antiseptic cap 900 and/or antiseptic cap holder assembly 404 at a time, while maintaining one or more other antiseptic caps 900 and/or antiseptic cap holder assemblies 404 attached to the dispensing device 600.

Each of the antiseptic caps 900 included in the dispensing device 600 may include any antiseptic cap holder and/or any antiseptic cap described herein. While FIGS. 11A-11D illustrate the dispensing device housing five antiseptic caps 900, any number of disinfectant filled devices can be attached to the dispensing device 600. Any of the embodiments of the dispensing device 600 described and/or contemplated herein can be modified to be used with any antiseptic cap described and/or contemplated herein.

As shown in the figures, the dispensing device 600 may include one or more antiseptic caps 900 attached to a cover, or dispensing surface 604. For example, as shown in FIGS. 11A-11D, a plurality of antiseptic caps 900 are attached to a single dispensing surface 604. Each of the antiseptic caps 900 can be any cap discussed herein.

The dispensing surface 604 has a width that is narrower than its length. A cap-storage device can comprise any other suitable shape and/or configuration capable of receiving at least a portion of an antiseptic cap 900 and/or an antiseptic cap holder assembly 404. A cap-storage device can comprise any suitable structure (e.g., straight and/or curved) and have any suitable shape (e.g., cylindrical, tapered).

A width of the dispensing surface 604, as shown in FIG. 11A-11D, may be larger than a width of the outer surface of the antiseptic cap 900 to facilitate attaching the antiseptic cap 900. In some embodiments, the width of the dispensing surface 604 may remain constant throughout the dispensing surface 604. In some embodiments, the width of the dispensing surface 604 may vary along the length of the dispensing surface 604. For example, the dispensing surface 604 can comprise a portion having a narrowed width. In some embodiments, the narrowed width may be located adjacent to a distal end of the dispensing device 600. In some embodiments, the width of the dispensing surface 604 may be sufficiently large to encompass two or more rows of antiseptic caps 900.

While FIGS. 11A-11D illustrate the dispensing device 600 as containing one row of five antiseptic caps 900, it is contemplated that the dispensing device 600 may contain any length or width sufficient to contain a plurality of antiseptic caps 900 and/or antiseptic cap holder assemblies 404. For example, the width and length of the dispensing surface 604 may be sufficiently large to encompass two or more rows of antiseptic caps 900, each row comprising two or more antiseptic caps 900. In some embodiments, the dispensing surface 604 may include notches, perforations, and/or scores between the plurality of antiseptic caps 900 and/or antiseptic cap holder assemblies 404. The notches may allow a user to tear off an individual unit, or any number of a plurality of units, for future use and still retain the individual sterile barrier of the unit(s).

As shown in FIGS. 11A-11D, the plurality of antiseptic cap assemblies 404 may be sealed with a dispensing surface 604. The dispensing surface 604 may permit each antiseptic cap 900 to remain sterile. The dispensing surface 604 may be configured to be sealed against one or more portions of the antiseptic cap 900. In some embodiments, the dispensing surface 604 can be sealed to the antiseptic cap 900, as identified by reference 608 in FIGS. 11A-11D. For example, the dispensing surface 604 may be attached to the antiseptic cap 900 by any suitable method such as by adhesives or by conductive or inductive heat sealing techniques discussed herein.

Attachment directly to the antiseptic cap 900 permits the dispensing surface 604 to seal the first chamber 925 and prevent the removal of any antiseptic material 940 and/or antiseptic fluid within the antiseptic cap 900. In some embodiments where the dispensing surface 604 is attached to one or more antiseptic cap holder assemblies 404 of FIGS. 5A and 5B, the dispensing surface 604 may form a double seal when the dispensing surface 604 is sealed against both the cap holder 402 and the antiseptic cap 900 within the cap holder 402. For example, a double seal may provide an extra barrier to prevent contamination of an antiseptic cap 900 and/or prevent an antiseptic material from escaping from the antiseptic cap 900. Providing a double seal may advantageously improve shelf life.

As shown in FIGS. 11A-11D, the dispensing device 600 can include one or more hanging holes 610. For example, the hole 610 may include a die cut hole or holes. The hole 610 can be sized and configured to allow the dispensing device 610 to be hung on a convenient hanger. For example, a user may utilize the one or more holes 610 to hang the dispensing device 600 on an IV pole. The hole 610 can comprise any suitable shape and/or configuration capable of allowing the dispensing device 600 to be hung on a hanger. It will be appreciated that location of the hole 610, as well as the relative size, indicated in FIGS. 11A-11D are exemplary and non-limiting. Indeed, it will be understood, that the location and relative size can be modified for any suitable embodiment, and that the relative proportions of the hole 610 in relation to the remainder of the dispensing device 600 can differ in various embodiments. In some embodiments, the dispensing device 600 may not incorporate one or more holes 610.

In some embodiments, the dispensing surface 604 may be thermally bonded to one or more of the antiseptic caps 900. Thermal bonding may occur using standard heat sealing technology, such as impulse, induction, conduction, radiant, or other heat sealing techniques. In some embodiments, the dispensing surface 604 could be attached to the antiseptic cap 900 by utilizing an adhesive bond or by a suitable mechanical or friction connection, such as a snap-fit.

To remove an antiseptic cap 900 from the dispensing device 600, a user may grasp a portion of the antiseptic cap holder assembly 404 that is extending from the dispensing surface 604 and apply a removal force, such as a downward force (if the dispensing device 600 is positioned in a vertically hanging orientation). In some embodiments, as discussed herein, a user may utilize a notch and/or perforation to remove at least a portion of the dispensing surface 604 when removing an antiseptic cap 900. This advantageously maintains at least one seal on the antiseptic cap 900 upon removal from the dispensing device 600. In some embodiments, the dispensing device 600 facilitates removal of the antiseptic cap 900 through an efficient process that only requires the use of a single hand.

In some embodiments, the inclusion of an antiseptic cap holder 402 on the dispensing device 600 may advantageously eliminate the need for direct contact with the antiseptic cap 900 during removal from the dispensing device 600. The antiseptic cap holder 402 may prevent contamination of an antiseptic cap 900 within the antiseptic cap holder 402. For example, a user may handle the antiseptic cap holder assembly 404 via one or more portions of the antiseptic cap holder 402, such as the flange 418 extending out from the antiseptic cap holder 402. The antiseptic cap holder 402 may act as a guard against contact of the antiseptic cap 900 by a user.

The antiseptic cap 900 may be withdrawn from the dispensing device 600 such that the removal (e.g., downward) force required to remove the antiseptic cap 900 from the dispensing surface 604 is lesser than the strength of the hole 610, such that the hole 610 does not tear and when the dispensing device 600 is in a vertically hanging position. For example, the peel force could generally be less than two pounds of force to start peeling, and less than one pound of force to continue peeling.

In some embodiments, the dispensing surface 604 could be made of any suitable material. For example, the dispensing surface 604 may comprise a foil, a plastic, a laminate, etc. In some instances, the dispensing surface 604 can be made of a foil material having a thickness of approximately 1 to 2 mil. The dispensing surface 604 can have a thick foil with a top coat of PET (polyethylene terephthalate), such as 48-gauge PET, then a polymer coat such as PDX which could be white, and a bottom coat of a peelable sealing layer, such as Allegro B, manufactured by Rollprint Packaging Products, Inc. The sealing layer can form an adhesive bond that can be peelable. The antiseptic caps 900 and/or antiseptic cap holder assemblies 404 may be attached to the dispensing surface 604 by induction heating of the foil, which melts the peelable sealing layer to adhere it to the antiseptic caps 900 and/or antiseptic cap holder assemblies 404.

In some embodiments, all or a portion of the dispensing device 600 may be made of a transparent material, thereby allowing a user to readily identify the dispensing device 600 as a holder of a particular type of medical devices (such as antiseptic caps and/or antiseptic cap holder assemblies), and/or to read information printed on the packaging of one or more types of medical devices within the bag, and/or to determine the quantity of antiseptic cap holder assemblies 404 remaining on the dispensing device 600 (such as to determine when it will be necessary to replace the dispensing device 600), from any viewing angle. In some embodiments, the dispensing device 600 avoids some complications associated with hanging the dispensing device 600 backwards, as the dispensing device 600 may be viewed and/or accessed from the front and back side.

Various features of the dispensing device 600 can comprise the various illustrated dimensions and proportions, which form part of this disclosure. It will be appreciated that these dimensions are exemplary and non-limiting. Indeed, it will be understood that the dimensions can be modified for any suitable embodiment, and that their relative proportions can differ in various embodiments.

Syringe Assembly

Figure 12A:
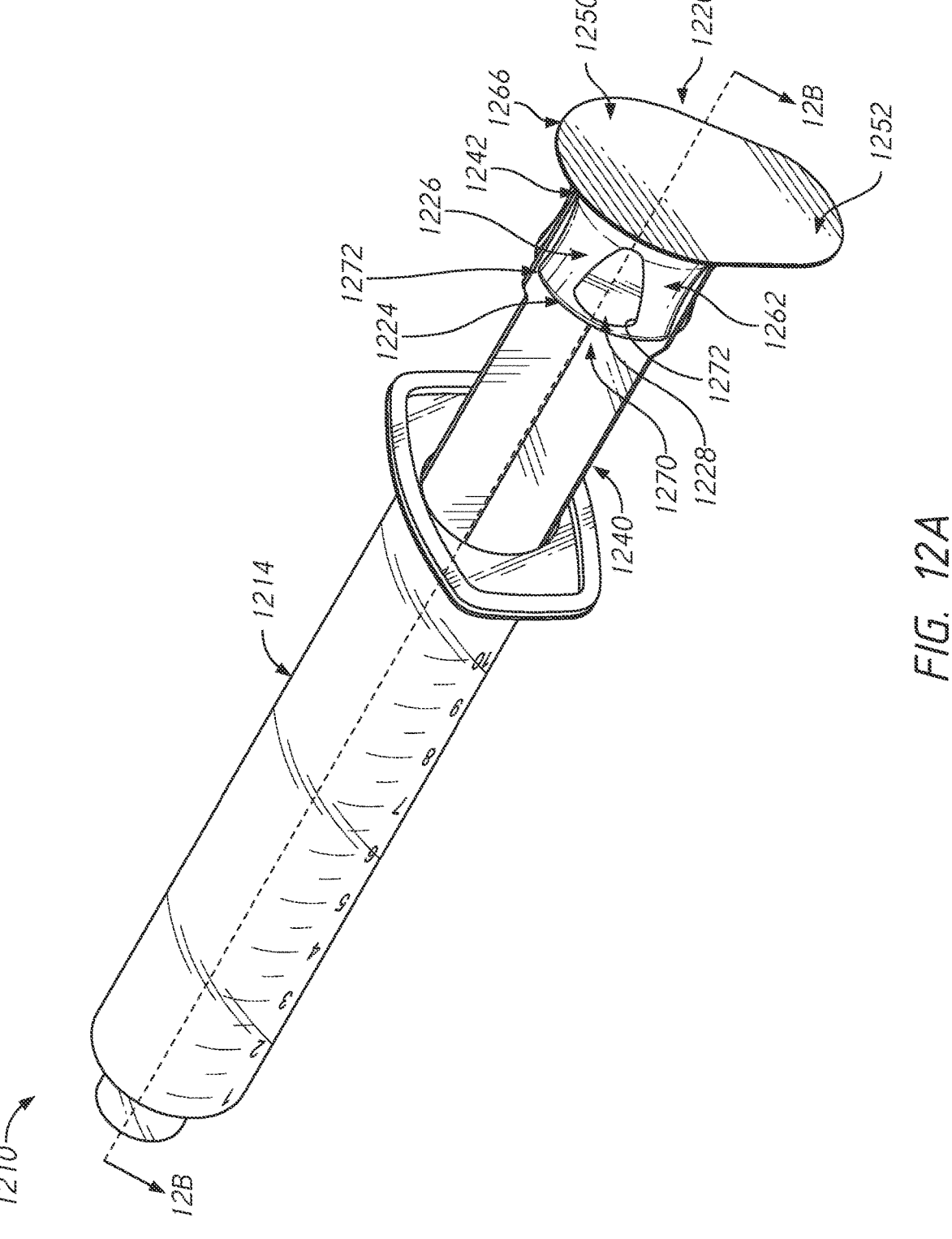
FIG. 12A is a front perspective view of an embodiment of a syringe assembly having an antiseptic cap holder assembly.
Figure 12B:
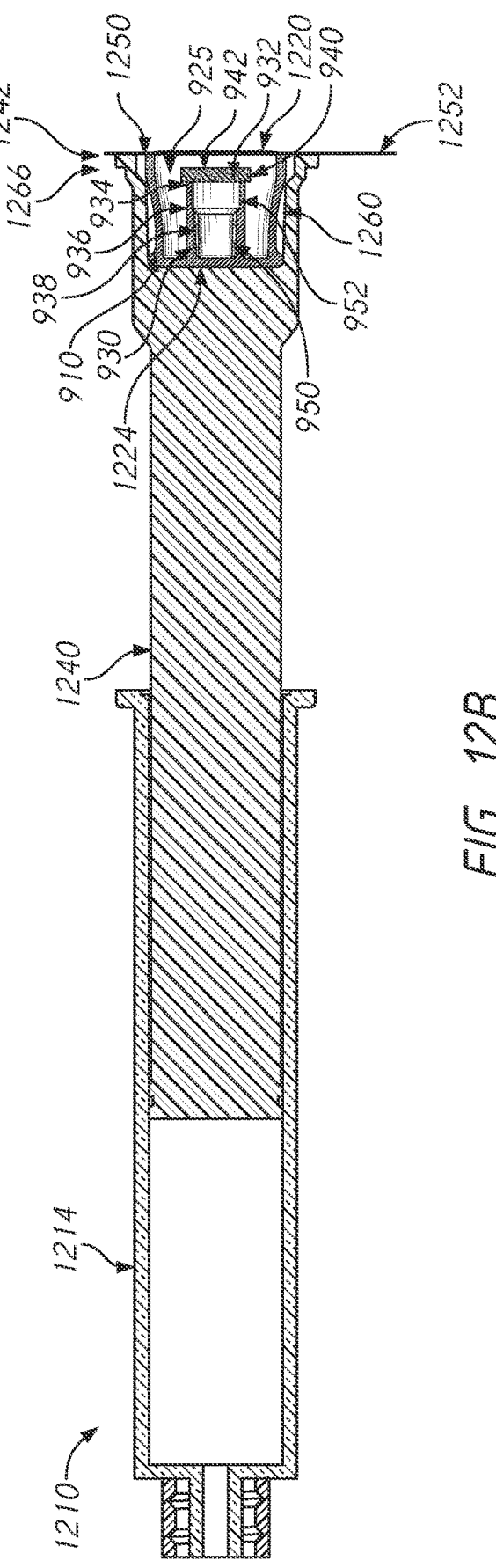
FIG. 12B is a cross-sectional view of the syringe assembly and the antiseptic cap holder assembly of FIG. 12A.

FIGS. 12A and 12B are various views of a syringe assembly 1210 including an antiseptic cap assembly 1220, according to some embodiments. In particular, FIG. 12A is a front perspective view of a syringe assembly 1210 including an antiseptic cap assembly 1220, and FIG. 12B is a side cross-sectional view of the syringe assembly 1210 of FIG. 12A. Unless otherwise noted, reference numerals in FIGS. 12A and 12B refer to components that are the same as or generally similar to the components in the remaining figures discussed herein. While the antiseptic cap assembly 1220 shown in FIGS. 12A and 12B are similar to antiseptic cap assembly 2004 shown in FIGS. 6-10, it will be understood that the features described with reference to syringe assembly 1210 shown in FIGS. 12A and 12B can be used with any antiseptic cap and/or cap holder assembly embodiments described and/or contemplated herein. For example, any one of the antiseptic cap 900 of FIGS. 1A-2, antiseptic cap 900 of FIGS. 3A-4, antiseptic cap holder assembly 404 of FIGS. 5A-5B, and/or any additional caps disclosed herein can be modified to function with the syringe assembly 1210, as shown and described with reference to FIGS. 12A and 12B.

FIGS. 12A and 12B show a syringe barrel assembly 1210 having an antiseptic cap equipped syringe assembly 1240 configured for removably receiving an antiseptic cap holder assembly 1220. The syringe assembly 1210 may include a syringe barrel 1214 and a plunger 1240. The barrel 1214 can include a side wall defining a chamber and a proximal opening in fluid communication with the chamber. In some embodiments, the chamber of the syringe assembly 1210 may be filled with a locking solution or a flush solution for use with an indwelling, central venous catheter. Some examples of suitable locking or flushing solutions are set forth below. The flush or locking solution is injected into a fluid access site of the catheter to clean and disinfect the catheter and can be withdrawn from the catheter or allowed to remain in an end portion of the catheter to serve as a barrier to the ingress of pathogens and contaminants.

The plunger 1240 may include an elongate shaft, a proximal end 1242, and a distal end (not shown in FIGS. 12A and 12B). The elongate shaft, in some embodiments, is generally cruciform in cross-sectional shape. A stopper or piston may be connected to the distal end of the plunger 1240. In some embodiments, the piston is dimensioned such that when inserted into the syringe barrel chamber, an outer circumferential surface of the piston is in fluid-tight engagement with an inner surface of the syringe barrel 1214. The piston assembly when moved proximally (or when being withdrawn) can draw fluid into the chamber and when moved distally (or when inserted into the syringe chamber) can drive fluid out of the chamber. FIGS. 12A and 12B show the piston assembly 1240 partially inserted into the syringe barrel 1214.

As shown in FIGS. 12A and 12B, in some embodiments, the proximal end 1242 of the plunger may include a chamber 1260, sized to receive and removably hold an antiseptic cap assembly 1220. Referring to FIG. 12B, the chamber 1260 can be comprise a bottom wall 1261 and an annular sidewall 1262 that has a peripheral proximal end 1266 that includes an opening 1268 through which the antiseptic cap assembly 1220 can be inserted into the chamber 1260. It will also be understood that any of the antiseptic caps and/or antiseptic cap holder assembly embodiments described and/or contemplated herein can be modified to be used with the syringe assembly shown in FIGS. 12A and 12B.

FIGS. 12A and 12B illustrate an antiseptic cap assembly 1220 within the chamber 1260 of the plunger assembly 1240. The antiseptic cap assembly 1220 can include any antiseptic cap holder assembly disclosed herein. For example, antiseptic cap assembly may comprise antiseptic cap holder assembly 404 disclosed in reference to FIGS. 5A and 5B. For example, as discussed herein, the cap assembly 1220 may comprises one or more of the following features: an antiseptic cap holder, an antiseptic cap 900, an antiseptic material 940, and a cover 1250. In some embodiments, a pull tab 1252 could be provided for facilitating removal of the film 1250 to provide access to the antiseptic cap 900. In some embodiments, the incorporation of separate plunger assembly 1240 and antiseptic cap assembly 1220 allows for the separate manufacture, assembly, and sterilization of the antiseptic cap assembly 1220 from the plunger assembly 1240 and the syringe barrel 1214.

In some embodiments, as illustrated in FIG. 12A, the sidewall 1262 of the plunger 1240 includes one or more apertures 1270 comprising edges 1272. The one or more apertures 1270 provide access to the chamber 1260 and facilitate removal of the cap assembly 1220 from the plunger 1240 as will be described hereinafter.

The cap assembly 1220 can be removed from the plunger 1240. In some embodiments, removal of the cap assembly 1220 from the plunger 1240 involves placing one's thumb or finger through the one or more apertures 1270 against a lower surface of the cap assembly 1220. A user may push against the cap assembly 1220 with a finger or thumb to urge the cap assembly 1220 out of the chamber 1260. Ultimately, the cap assembly 1220 is ejected from the chamber 1260. In this way, the antiseptic cap 900 could be conveniently used at a different time than the syringe 1210.

In some embodiments, the chamber 1260 of the plunger 1240 may include an interior surface comprising a plurality of circumferentially spaced ribs. The plurality of ribs may be configured to contact an antiseptic cap assembly 1220 and secure the antiseptic cap assembly 1220 within the chamber 1260. The ribs, in some instances, could each contain a slot shaped to receive a corresponding rib located on an outer surface of the antiseptic cap assembly 1220 to secure the cap holder assembly 1220 within the chamber 1260. The ribs of the chamber 1260 could also be tapered to facilitate the controlled removal of the antiseptic cap assembly 1220, and prevent the antiseptic cap assembly 1220 from ejecting too rapidly. The ribs can provide a decreasing amount of resistance against the cap 1222 as the antiseptic cap assembly 1220 is urged out of the chamber 1260. It will also be understood that any of the embodiments described and/or contemplated herein can be modified to be used with chamber 1260 shown in FIGS. 12A and 12B.

As partially shown in FIG. 12A, the plunger 1240 may include four support walls extending at 90 degree angles with respect to each other from a common point. Towards the proximal end 1242 of the plunger 1240, one or more support walls may have one or more recessed areas proximal the one or more apertures 1270 to facilitate removal of the cap assembly by providing more clearance for a user to place his or her thumb beneath the cap assembly. In some embodiments, an outermost edge of the recessed area is closer to the common point than the outermost edge of the rest of the sidewall. The recessed area can comprise a flat edge a, sloped edge, or both.

In some embodiments, the plunger 1240 may not include a chamber and an antiseptic cap holder and/or antiseptic cap assembly may be retrofitted to be attached to a distal end of the plunger 1240. The plunger 1204, in some instances, may comprise a button at the distal end and the cap and/or the antiseptic cap assembly may be configured to engage the button. For example, the cap and/or antiseptic cap assembly may include a proximal end that is removably or fixedly attached to a button of the plunger. The proximal end may include an opening dimensioned to fit about the button and can comprise a member for attaching to the button. In some embodiments, the attaching member includes a plurality of circumferentially spaced, and axially inwardly directed tabs extending from an inner wall surface. In some embodiments, the tabs engage a lower surface of the button to attach the cap holder and/or antiseptic cap assembly to the plunger.

The syringe assembly 1210 can be fabricated from any material suitable for its purpose and includes glass and polymeric material. Suitable polymeric materials include, but are not limited to, homopolymers, copolymers and terpolymers formed from monomers such as olefins, cyclic olefins, amides, esters, and ethers. The polymeric material may be a blend of more than one polymeric material and can be a monolayer structure or a multilayer structure. In some embodiments, the syringe barrel and the plunger are injection molded from a polypropylene material.

Antiseptic Material

Unless otherwise noted, the antiseptic material described below refers to components that are the same as or generally similar to the components discussed herein in the present application. It will be understood that the features described below can be used with any of the embodiments described and/or contemplated herein. For example, any one of the antiseptic caps disclosed herein can be modified to include any antiseptic material, as described below or anywhere else in this specification or otherwise.

An antiseptic material may include medical grade materials capable of storing and releasing an antiseptic liquid, or liquid having other medical purposes, and includes materials such as sponges, rupturable capsules and other materials or devices capable of serving this purpose. Suitable sponges can include any sponge suitable for use for medical purposes and can be naturally occurring or synthetic. The antiseptic material can be cut into suitable shapes or can be molded into the desired shape. It is desirable that the antiseptic material be attached to an antiseptic cap to prevent the antiseptic material from inadvertently falling out and/or off of the antiseptic cap. For example, the antiseptic material may be attached to an antiseptic cap by any suitable method such as ultrasonic or vibrational welding or other suitable technique.

The antiseptic material can comprise any material suitable for storing and/or releasing antiseptic liquid. In some embodiments, the antiseptic material can comprise any suitable polymer. In some embodiments, the polymer may include a polymer foam. For example, the antiseptic material may include a polyurethane, polyester, polycarbonate, and/or polyamid. The antiseptic material may comprise an open-cell foam. In some embodiments, the foam may comprise a density of at least about 0.8 and/or less than or equal to about 2.8 pounds per cubic foot.

In some embodiments, one or more portions of the any one of the antiseptic caps described herein may be coated and/or impregnated with an antiseptic fluid, an anticoagulant fluid, an antimicrobial fluid, and/or any other suitable therapeutic fluid. The one or more portions of the antiseptic cap that may be coated and/or impregnated include an inner surface of a cap wall, threads, an outer surface of the cap wall, an inner surface of the cap wall, and/or any additional features of the caps disclosed herein.

The antiseptic can comprise any substance suitable for its purpose. Suitable substances include, but are not limited to, isopropyl alcohol (IPA), Chlorhexidine, one or more metal ions (e.g., silver), citrate salt solution, etc. In some embodiments, the antiseptic agent can contain antibacterial agents such as those classified as aminoglycosides, beta lactams, quinolones or fluoroquinolones, macrolides, sulfonamides, sulfamethaxozoles, tetracyclines, treptogramins, oxazolidinones (such as linezolid), clindamycins, lincomycins, rifamycins, glycopeptides, polymxins, lipo-peptide antibiotics, as well as pharmacologically acceptable sodium salts, pharmacologically acceptable calcium salts, pharmacologically acceptable potassium salts, lipid formulations, derivatives and/or analogs of the above. In some embodiments, the antiseptic agent can contain antifungal agents. In some embodiments, the antiseptic agent can contain antiviral agents. The antiseptic may be a blend of more than one antiseptic material.

In some embodiments, a quantity of physiological, antimicrobial metal compound is added to the resin for direct molding of an article. Physiological, antimicrobial metals are meant to include the precious metals, such as silver, gold and platinum, and copper and zinc. Physiological, antimicrobial metal compounds used herein may include oxides and salts of silver and also gold, for example: silver acetate, silver benzoate, silver carbonate, silver citrate, silver chloride, silver iodide, silver nitrate, silver oxide, silver sulfa diazine, silver sulfate, gold chloride and gold oxide. Platinum compounds such as chloroplatinic acid or its salts (e.g., sodium and calcium chloroplatinate) may also be used. Also, compounds of copper and zinc may be used, for example: oxides and salts of copper and zinc such as those indicated above for silver. Single physiological, antimicrobial metal compounds or combinations of physiological, antimicrobial metal compounds may be used.

In some embodiments, physiological, antimicrobial metal compounds used may include silver acetate, silver oxide, silver sulfate, gold chloride and a combination of silver oxide and gold chloride. The particles of the silver compounds are sufficiently able to be extracted to form a zone of inhibition to prevent and kill bacteria growth.

In some embodiments, the devices herein are impregnated with triclosan and silver compounds or triclosan and chlorhexidine.

Further details regarding the embodiments disclosed herein, including an antiseptic cap, can be found in International Patent Application No. PCT/US2017/056407. It will be understood that any of the functions, materials, methods, systems, and devices described and/or contemplated within International Patent Application No. PCT/US2017/056407 can be modified to be used with the various functions, materials, methods, systems, and devices systems described herein. For example, the antiseptic cap may further comprise any embodiment described and/or contemplated within International Patent Application No. PCT/US2017/056407. Additionally, any of the functions, materials, methods, systems, and devices described and/or contemplated herein can be modified to be used with the various functions, materials, methods, systems, and devices systems described and/or contemplated within International Patent Application No. PCT/US2017/056407.

Other Variations

Although this invention has been disclosed in the context of certain embodiments and examples, the invention extends beyond the specifically disclosed embodiments to other alternative embodiments and/or uses of the invention and equivalents thereof. In addition, while several variations of the invention have been shown and described in detail, other modifications are within the scope of this invention. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the claims that follow. Moreover, language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result.

The following is claimed:

1. A sanitizing male luer cap comprising:
a housing comprising:
an outer wall,
a bottom wall, and
a first chamber being at least partially enclosed by the outer wall and the bottom wall;
an inner protrusion extending upwardly from the bottom wall of the housing, the inner protrusion comprising:
an inner surface, and
a second chamber being at least partially formed by the inner surface of the inner protrusion, at least a portion of the inner surface of the inner protrusion being tapered and configured to tightly receive at least a portion of a male luer of a medical connector;
an antiseptic material comprising an opening for receiving the male luer and an antiseptic liquid within the antiseptic material, the antiseptic material being attached to an upper end of the inner protrusion and extending across an opening to the second chamber such that the antiseptic material is configured to wipe and to apply the antiseptic liquid to a distal end face and a side wall of the male luer as the male luer is advanced into the second chamber; and
a lid being configured to enclose the first chamber and resist escape of the antiseptic liquid from the first chamber before use;
wherein an interior surface of the outer wall of the housing does not contact the medical connector when the sanitizing male luer cap is attached to the medical connector such that a gap is formed between the interior surface of the outer wall of the housing and the medical connector.

2. The sanitizing male luer cap of claim 1, wherein a portion of the antiseptic material is configured to move into the second chamber as the sanitizing male luer cap is advanced onto the male luer of the medical connector.

3. The sanitizing male luer cap of claim 1, wherein an upper diameter of the inner protrusion is smaller than a width of the antiseptic material.

4. The sanitizing male luer cap of claim 1, wherein a length of a perforation in the antiseptic material is less than or equal to a largest diameter of the portion of the male luer of the medical connector that is insertable into the inner protrusion, such that the antiseptic material is configured to form a tight fit around the male luer when the sanitizing male luer cap is attached to the medical connector.

5. A combination of the sanitizing male luer cap of claim 1 and the medical connector referenced in claim 1.

6. A sanitizing luer cap comprising:
an antiseptic material being configured to sanitize a male luer end of a medical connector when the sanitizing luer cap is attached to the medical connector by wiping and applying an antiseptic liquid to a distal end face and a side wall of the male luer end; and
a housing having an interior surface forming a chamber;
a protrusion positioned within the chamber, the protrusion comprising:
an outer surface being coupled to the antiseptic material,
an opening being configured to receive the male luer end of the medical connector,
a distal portion comprising a first inner cross-sectional width, the distal portion of the protrusion being configured to receive at least a portion of the antiseptic material when the sanitizing luer cap receives the medical connector, and a proximal portion comprising a second inner cross-sectional width being different than the first inner cross-sectional width, the proximal portion of the protrusion being configured to couple to the portion of the male luer end when the sanitizing luer cap attaches to the medical connector and to hold the sanitizing luer cap on the medical connector.

7. The luer cap of claim 6, wherein the first inner cross-sectional width is greater than the second inner cross-sectional width.

8. The luer cap of claim 6, wherein the first inner cross-sectional width is sized such that the distal portion is configured to receive at least a portion of the antiseptic material and the male luer.

9. The luer cap of claim 6, wherein the antiseptic material includes an opening configured to accept the male luer end of the medical connector.

10. The luer cap of claim 6, wherein the antiseptic material comprises a diameter, and wherein the diameter is greater than the first inner cross-sectional width and the second cross-sectional width.

11. The luer cap of claim 6, wherein the antiseptic material is configured to sanitize at least an end face of the male luer end.

12. The luer cap of claim 6, wherein the antiseptic material comprises one or more perforations configured to facilitate passage of at least a portion of the male luer end through the antiseptic material.

13. The luer cap of claim 12, wherein the one or more perforations comprises a length, and wherein the length is less than an outer width of at least the portion of the male luer end.

14. The luer cap of claim 13, wherein the length of the one or more perforations is configured to inhibit passage of fluid between the antiseptic material and the male luer end.

15. The luer cap of claim 6, wherein the antiseptic material comprises one or more flap portions.

16. The luer cap of claim 15, wherein the one or more flap portions are configured to be at least partially positioned within the distal portion of the protrusion when the sanitizing luer cap is attached to the male luer end.

17. The luer cap of claim 16, wherein the one or more flap portions comprises a compressible material to compress between the distal portion of the protrusion and at least a portion of the male luer end.

18. The luer cap of claim 16, wherein the one or more flap portions are configured to facilitate attachment of the sanitizing luer cap to the male luer end.

19. A combination of the sanitizing luer cap of claim 6 and the medical connector referenced in claim 6.

20. An antiseptic cap assembly comprising:

one or more sanitizing luer caps of claim 6; and an elongate tubular body or sleeve configured to contain the one or more sanitizing luer caps.

21. An antiseptic cap assembly comprising:

a sanitizing luer cap of claim 6;

a cap holder configured to receive the sanitizing luer cap; and a lid.

\* \* \* \* \*